(12) United States Patent
Eilers et al.

(10) Patent No.: US 6,265,562 B1
(45) Date of Patent: Jul. 24, 2001

(54) NUCLEIC ACID CONSTRUCTS WHOSE ACTIVITY IS AFFECTED BY INHIBITORS OF CYCLIN-DEPENDENT KINASES AND USES THEREOF

(75) Inventors: Martin Eilers; Andrea Buergin; Hans-Harald Sedlacek, all of Marburg (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 0 days.

(21) Appl. No.: 09/215,221

(22) Filed: Dec. 18, 1998

(30) Foreign Application Priority Data

Dec. 20, 1997 (DE) .............................. 197 56 975

(51) Int. Cl.[7] .................... C07H 21/04; C07H 21/02
(52) U.S. Cl. .................... 536/23.4; 536/23.1; 536/23.5
(58) Field of Search .................... 536/23.1, 23.4, 536/23.5; 514/44

(56) References Cited

U.S. PATENT DOCUMENTS

| 5,464,758 | 11/1995 | Gossen et al. | 435/69.1 |
|---|---|---|---|
| 5,830,880 | 11/1998 | Sedlacek et al. | 514/44 |
| 5,854,019 | 12/1998 | Sedlacek et al. | 435/69.1 |
| 5,885,833 | 3/1999 | Mueller et al. | 435/372 |
| 5,916,803 | 6/1999 | Sedlacek et al. | 435/320.1 |

FOREIGN PATENT DOCUMENTS

| 0 455 424 A2 | 11/1991 | (EP) . |
| 0 922 768 A2 | 6/1999 | (EP) . |
| 96/01313 | 1/1996 | (WO) . |

OTHER PUBLICATIONS

Zerfass–Thome et al., *Oncogene* 13:2323–2330 (1996).
Rivera et al., *Nature Medicine* 2:1028–1032 (Sep. 1996).
Kirchhoff et al., *Nucleic Acids Research* 21:2881–2889 (1993).
Wang et al., *Proc. Natl. Acad. Sci. USA* 91:8180–8184 (Aug. 1994).
Neckers et al.; "Antisense Inhibition of Oncogene Expression"; Crit. Rev. Oncogen 3; (1992); pp. 175–231.

*Primary Examiner*—Karen M. Hauda
*Assistant Examiner*—Joseph T. Woitach

(57) ABSTRACT

The present application discloses nucleic acid constructs comprising nucleic acids which encode a protein which inhibits the cellular protein p27 and thereby relieves the inhibition of the proliferation of the cell which is brought about by p27, fragments and variants thereof, some of which possess a dominant interfering character.

28 Claims, 25 Drawing Sheets

Component:

| a) | b1) | b2) | b3) | c) | d) |
|---|---|---|---|---|---|
| Activation Sequence (promoter I) | Activation domain of a transcription factor | p163- or p27-binding protein | DNA-binding domain of a transcription factor | Activation Sequence (Promoter II) | Effector gene |

Figure 1:

| DNA-binding domain (Gal4) | Partner molecule I | Partner molecule II | Activation domain (VP16) | Galacto-sidase activity |
|---|---|---|---|---|
| + | p27 (1-198) | - | - | - |
| + | p27 (1-198) | - | + | - |
| + | p27 (1-198) | p163 | + | +++ |
| + | - | - | - | - |
| - | - | p163 | + | - |
| + | Myc 262-439 | p163 | + | - |
| + | Max | p163 | + | - |
| + | Prothymosin | p163 | + | - |
| + | LAZ3/Bcl6 | p163 | + | - |
| + | p27 (1-178) | p163 | + | +++ |
| + | p27 (1-94) | p163 | + | + |
| + | p27 (69-198) | p163 | + | +++ |
| + | p27 (69-94) | p163 | + | n.d. |
| + | p27 (1-198) | p163 (121-252) | + | +++ |

Figure 2

| Column loading | Binding to affinity chromatography column coated with | |
| --- | --- | --- |
| | Glutathione transferase - p163 fusion protein | Glutathione transferase |
| Recombinant ($^{35}$S-labeled) p27 | +++ | + |
| Cell extract (RAT1-Myc ER), containing p27 | (+) | - |
| Cell extract (RAT1-Myc ER), containing p27 (heated at 95°C for 2 min) | +++ | - |
| cdk-2 (cell extract) | - | - |
| cdk-4 (cell extract) | - | - |

FIGURE 3A

```
TCGAATTGGG TACCGGGCCC CCCCTCGAGG TCGACGGTAT CGATAAGCTT GATATCGAAT    60
TCGCGGCCGC TCGAGTTACA AGATGGCGGC CCGGGCGCT  CTCTTCACCG TTCTGTAGCA   120
GCTTCGGGCT GAGCGGATGT CTCTTCTTGT CCTCAGTGTC GGACTCAGAG ACACACGGCT   180
CCCGAGTTCT GCTGATCACG AAGTTCCCGG AGGCGCTCGA CGCACCGGAA TCTCCCAGCG   240
GCCGCGACCG CCGCCTCGGC CCTGCTCGCC GCGGCGCCGG GACTCCAGCG TGATCGGCGG   300
CGGCAGTCAA GGTTCACAAA AATGGCGAAG AGAGTTGCGG AGAAGGAGTT GACTGACAGG   360
AACTGGGATG AGGAAGACGA AGTTGAAGAG ATGGGAACAT TCTCAGTGGC CAGTGAGGAA   420
GTCATGAAGA ACAGAGCCGT AAAGAAGGCA AAGCGCAGAA ACGTTGGATT TGAATCTGAT   480
AGCGGAGGAG CCTTTAAAGG TTTCAAAGGT TTGGTTGTGC CTTCTGGAGG AGGAGGGTTT   540
TCTGGATTTG GTGGCTCTGG AGGAAAGCCT CTGGAAGGAC TGACAAATGG AAACAGCACA   600
GACAATGCCA CGCCCTTCTC CAATGTAAAG ACAGCAGCAG AGCCCAAGGC AGCCTTTGGT   660
TCTTTTGCTG TGAATGGCCC TACTACCTTG GTGGATAAAG TTTCAAATCC AAAAACTAAT   720
GGGGACAGCA ATCAGCCGCC CTCCTCCGGC CCTGCTTCCA GTACCGCCTG CCCTGGGAAT   780
GCCTATCACA AGCAGCTGGC TGGCTTGAAC TGCTCCGTCC GCGATTGGAT AGTGAAGCAC   840
GTGAACACAA ACCCGCTTTG TGACCTGACT CCCATTTTTA AAGACTATGA GAGATACTTG   900
GCGACGATCG AGAAGCAGCT TGAGAATGGA GGCGGCAGCA GTTCTGAGAG CCAGACAGAC   960
AGGGCGACGG CTGGAATGGA GCCTCCTTCC CTTTTTGGTT CAACAAAACT ACAGCAAGAG  1020
TCACCATTTT CATTTCATGG CAACAAAGCG GAGGACACAT CTGAAAAGGT GGAGTTTACA  1080
GCAGAAAAGA AATCGGACGC AGCACAAGGA GCAACAAGTG CCTCGTTTAG TTTCGGCAAG  1140
AAAATTGAGA GCTCGGCTTT GGGCTCGTTA AGCTCTGGCT CCCTAACTGG GTTTTCATTC  1200
TCTGCTGGAA GCTCCAGCTT GTTTGGTAAA GATGCTGCCC AGAGTAAAGC AGCCTCTTCG  1260
CTGTTCTCTG CTAAAGCATC CGAGAGTCCG GCAGGAGGCG GCAGCAGCGA GTGCAGAGAT  1320
GGTGAAGAAG AGGAGAATGA CGAGCCACCC AAGGTAGTGG TGACCGAAGT AAAGGAAGAG  1380
GATGCTTTCT ACTCCAAAAA ATGTAAACTA TTTTACAAGA AAGACAACGA ATTTAAAGAG  1440
AAGGGTGTGG GGACCCTGCA TTTAAAACCC ACAGCAACTC AGAAGACCCA GCTCTTGGTG  1500
CGGGCAGACA CCAACCTAGG CAACATACTG CTGAATGTTC TGATCGCCCC CAACATGCCG  1560
TGCACCCGGA CAGGAAAGAA CAACGTCCTT ATCGTCTGTG TCCCCAACCC CCCACTCGAT  1620
GAGAAGCAGC CCACTCTCCC GGCCACCATG CTGATCCGGG TGAAGACGAG CGAGGATGCC  1680
```

FIGURE 3B

```
GATGAATTGC ACAAGATTTT ACTGGAGAAA AAGGATGCCT GAGCACTGAG GCTGACCAAG    1740

GCATGTTGCC ACGTTGCTGC TTCCCCTCCG TCCCTAACTT AGTCACATTC TTTCCTCTTC    1800

TACTGTGACA TTCTGAGAAC TTCTAGGTAA CTTGAACTTT TGTGAGGAAG ATTAAGGCCA    1860

ATAAATCCTT TCAGTGGCGG CCGCGAATTC CTGCAGCCCG GGGATCCAC TAGTTCTAGA     1920

GCGGCCGCCA CCGCGGTGGA GCTCCAGCTT TTGGGAGA                            1958
```

Figure 4:

| | | | | |
|---|---|---|---|---|
| p163: | 1 | MAKRVAEKELTDRNWDEEDEVEEM 24 | | [SEQ ID NO.: 10] |
| | | MAKRVA+ ++ +D + +++ | | |
| YNup2: | 1 | MAKRVADAQIQRETYDSNESDDDV 24 | | [SEQ ID NO.: 11] |

| | | |
|---|---|---|
| P163: | 137 | NQPPSSGPASSTACPGNAYHKQLAGLNCS |
| | | N+ +G A P + +L LN |
| YNup2: | 71 | NRADGTGEAQVDNSPTTESNSRLKALNLQ |

| | | | |
|---|---|---|---|
| | | VRDWIVKHVNTNPLCDLTPIFKDYERYLATI 196 | [SEQ ID NO.: 12] |
| | | ++ + V PL DL P+F YE Y+ I | |
| | | FKAKVDDLVLGKPLADLRPLFTRYELYIKNI 130 | [SEQ ID NO.: 13] |

| | | |
|---|---|---|
| P163: | 215 | ATAGMEPPSLFGSTKLQQESPFSFHGNKAEDT |
| | | A + P ST + PF G++ |
| YNup2: | 535 | ANSSTSPAPSIPSTGFKFSLPFEQKGSQTTTN |

| | | | |
|---|---|---|---|
| | | SEKVEFTAEKKSDAAQGAT 265 | [SEQ ID NO.: 14] |
| | | K E T E + +Q AT | |
| | | DSKEESTTEATGNESQDAT 585 | [SEQ ID NO.: 15] |

| | | | |
|---|---|---|---|
| P163: | 239 | HGNKAEDTSEKVEFTAEKKSDAAQGATSASFSFG 272 | [SEQ ID NO.: 16] |
| | | +G++++D+ + +A + + AT +FSFG | |
| YNup2: | 444 | NGSESKDSDKPSLPSAVDGENDKKEATKPAFSFG 477 | [SEQ ID NO.: 17] |

| | | | |
|---|---|---|---|
| P163: | 399 | LGNILLNVLIAPNMPCTRTGKNNVLIVCVPNPPLDEKQPT 438 | [SEQ ID NO.: 18] |
| | | +GN+LLN + + N ++ P D K T | |
| YNup2: | 655 | MGNVLLNATVVDSFKYEPLAPGNDNLIKAPTVAADGKLVT 694 | [SEQ ID NO.: 19] |

Figure 5

```
RBP1  (mouse)        DSHADHDTST---ENADESTTHP--QFEPIVSVPE----
RBP1  (human)    5           DSHADHDTST---ENADESNHDP--QFEPIVSVPE----
NUP2p (yeast)  560           SQTTTNDSKE---ESTTEATGNESQDATKVDATPEESKP
p163  (mouse)  307           QSKAASSLFSAKASESPAGGGSSECRDGEEEENDEPPKV RBP1  (mouse)        QEIKTLEEDEEELFKMRAKLFRFASENDLPEWKEPRHGDVKLLKHK-
RBP1  (human)        QEIKTLEEDEEELFKMRAKLFRFASENDLPEWKERGTGDVKLLKHK-
NUP2p (yeast)        INLQNGEEDEVALFSQKAKLMTFNA--ETKSYDSRGVGEMKLLKKKD
p163  (mouse)        VVTEVK--EEDAFYSKKCKLFYKKDNEF----KEKGVTLHL-KPT- RBP1  (mouse)        EKGTIRLLMRRDKTLKI-CANHYITPMMELKP-NAGSDRAWVWNTHTD
RBP1  (human)        EKGTIRLLMRRDKTLKI-CANHYITPMMELKP-NAGSDRAWVWNTHTD
NUP2p (yeast)        DSPKVRLLCRSDGMGNV-LLNATVVDSFKYEPLAPGNDNLIKAPTVAA
p163  (mouse)        ATQKTQLLVRADTNLGNILLNVLIAPNMPCTRTGKNNVLIVCVPNP--

RBP1  (mouse)        FADECP--KPELLAIRFLNAENAQKFKTKFEECRKEI    [SEQ ID NO.: 20]
RBP1  (human)        FADECP--KPELLAIRFLNAENAQKFKTKFEECRKEI    [SEQ ID NO.: 21]
NUP2p (yeast)        DG-------KLVTYIVFKQKLEGRSFTKAIEDAKKEM    [SEQ ID NO.: 22]
p163  (mouse)        PLDEKQPTLPATMLIRVKTSEDADELHKILLEKKDAA    [SEQ ID NO.: 23]
```

Figure 6A p163 (Mouse)  [SEQ ID NO.: 24]

Met Ala Lys Arg Val Ala Glu Lys Glu Leu Thr Asp Arg Asn Trp Asp
1                5                10               15

Glu Glu Asp Glu Val Glu Glu Met Gly Thr Phe Ser Val Ala Ser Glu
           20               25                30

Glu Val Met Lys Asn Arg Ala Val Lys Lys Ala Lys Arg Arg Asn Val
         35               40               45

Gly Phe Glu Ser Asp Ser Gly Gly Ala Phe Lys Gly Phe Lys Gly Leu
       50              55                  60

Val Val Pro Ser Gly Gly Gly Phe Ser Gly Phe Gly Gly Ser Gly
65              70              75                    80

Gly Lys Pro Leu Glu Gly Leu Thr Asn Gly Asn Ser Thr Asp Asn Ala
               85                 90                  95

Thr Pro Phe Ser Asn Val Lys Thr Ala Ala Glu Pro Lys Ala Ala Phe
           100              105                110

Gly Ser Phe Ala Val Asn Gly Pro Thr Thr Leu Val Asp Lys Val Ser
           115              120              125

Asn Pro Lys Thr Asn Gly Asp Ser Asn Gln Pro Pro Ser Ser Gly Pro
       130              135              140

Ala Ser Ser Thr Ala Cys Pro Gly Asn Ala Tyr His Lys Gln Leu Ala
145              150              155                  160

Gly Leu Asn Cys Ser Val Arg Asp Trp Ile Val Lys His Val Asn Thr
               165              170              175

Asn Pro Leu Cys Asp Leu Thr Pro Ile Phe Lys Asp Tyr Glu Arg Tyr
           180              185              190

Leu Ala Thr Ile Glu Lys Gln Leu Glu Asn Gly Gly Gly Ser Ser Ser
           195              200              205

Glu Ser Gln Thr Asp Arg Ala Thr Ala Gly Met Glu Pro Pro Ser Leu
    210              215              220

Phe Gly Ser Thr Lys Leu Gln Gln Glu Ser Pro Phe Ser Phe His Gly
225              230              235                  240

Asn Lys Ala Glu Asp Thr Ser Glu Lys Val Glu Phe Thr Ala Glu Lys
               245              250              255

Lys Ser Asp Ala Ala Gln Gly Ala Thr Ser Ala Ser Phe Ser Phe Gly
           260              265              270

Lys Lys Ile Glu Ser Ser Ala Leu Gly Ser Leu Ser Ser Gly Ser Leu
       275              280              285

FIGURE 6B

Thr Gly Phe Ser Phe Ser Ala Gly Ser Ser Ser Leu Phe Gly Lys Asp
   290              295                  300

Ala Ala Gln Ser Lys Ala Ala Ser Ser Leu Phe Ser Ala Lys Ala Ser
305              310                  315                  320

Glu Ser Pro Ala Gly Gly Gly Ser Ser Glu Cys Arg Asp Gly Glu Glu
                325                  330                  335

Glu Glu Asn Asp Glu Pro Pro Lys Val Val Val Thr Glu Val Lys Glu
            340                  345                  350

Glu Asp Ala Phe Tyr Ser Lys Lys Cys Lys Leu Phe Tyr Lys Lys Asp
            355                  360                  365

Asn Glu Phe Lys Glu Lys Gly Val Gly Thr Leu His Leu Lys Pro Thr
    370                  375                  380

Ala Thr Gln Lys Thr Gln Leu Leu Val Arg Ala Asp Thr Asn Leu Gly
385                  390                  395                  400

Asn Ile Leu Leu Asn Val Leu Ile Ala Pro Asn Met Pro Cys Thr Arg
                405                  410                  415

Thr Gly Lys Asn Asn Val Leu Ile Val Cys Val Pro Asn Pro Pro Leu
            420                  425                  430

Asp Glu Lys Gln Pro Thr Leu Pro Ala Thr Met Leu Ile Arg Val Lys
        435                  440                  445

Thr Ser Glu Asp Ala Asp Glu Leu His Lys Ile Leu Leu Glu Lys Lys
    450                  455                  460

Asp Ala
465

NUP2 (Yeast)        [SEQ ID NO.: 25]

Met Ala Lys Arg Val Ala Asp Ala Gln Ile Gln Arg Glu Thr Tyr Asp
1            5                  10                  15

Ser Asn Glu Ser Asp Asp Asp Val Thr Pro Ser Thr Lys Val Ala Ser
            20                  25                  30

Ser Ala Val Met Asn Arg Arg Lys Ile Ala Met Pro Lys Arg Arg Met
        35                  40                  45

Ala Phe Lys Pro Phe Gly Ser Ala Lys Ser Asp Glu Thr Lys Gln Ala
    50                  55                  60

Ser Ser Phe Ser Phe Leu Asn Arg Ala Asp Gly Thr Gly Glu Ala Gln
65              70                  75                  80

Val Asp Asn Ser Pro Thr Thr Glu Ser Asn Ser Arg Leu Lys Ala Leu
            85                  90                  95

FIGURE 6C

```
Asn Leu Gln Phe Lys Ala Lys Val Asp Asp Leu Val Leu Gly Lys Pro
            100             105             110
Leu Ala Asp Leu Arg Pro Leu Phe Thr Arg Tyr Glu Leu Tyr Ile Lys
            115             120             125
Asn Ile Leu Glu Ala Pro Val Lys Phe Ile Glu Asn Pro Thr Gln Thr
            130             135             140
Lys Gly Asn Asp Ala Lys Pro Ala Lys Val Glu Asp Val Gln Lys Ser
145             150             155             160
Ser Asp Ser Ser Ser Glu Asp Glu Val Lys Val Glu Gly Pro Lys Phe
            165             170             175
Thr Ile Asp Ala Lys Pro Pro Ile Ser Asp Ser Val Phe Ser Phe Gly
            180             185             190
Pro Lys Lys Glu Asn Arg Lys Lys Asp Glu Ser Asp Ser Glu Asn Asp
            195             200             205
Ile Glu Ile Lys Gly Pro Glu Phe Lys Phe Ser Gly Thr Val Ser Ser
    210             215             220
Asp Val Phe Lys Leu Asn Pro Ser Thr Asp Lys Asn Glu Lys Lys Thr
225             230             235             240
Glu Thr Asn Ala Lys Pro Phe Ser Phe Ser Ser Ala Thr Ser Thr Thr
            245             250             255
Glu Gln Thr Lys Ser Lys Asn Pro Leu Ser Leu Thr Glu Ala Thr Lys
            260             265             270
Thr Asn Val Asp Asn Asn Ser Lys Ala Glu Ala Ser Phe Thr Phe Gly
            275             280             285
Thr Lys His Ala Ala Asp Ser Gln Asn Asn Lys Pro Ser Phe Val Phe
    290             295             300
Gly Gln Ala Ala Ala Lys Pro Ser Leu Glu Lys Ser Ser Phe Thr Phe
305             310             315             320
Gly Ser Thr Thr Ile Glu Lys Lys Asn Asp Glu Asn Ser Thr Ser Asn
            325             330             335
Ser Lys Pro Glu Lys Ser Ser Asp Ser Asn Asp Ser Asn Pro Ser Phe
            340             345             350
Ser Phe Ser Ile Pro Ser Lys Asn Thr Pro Asp Ala Ser Lys Pro Ser
            355             360             365
Phe Asn Phe Gly Val Pro Asn Ser Ser Lys Asn Glu Thr Ser Lys Pro
            370             375             380
Val Phe Ser Phe Gly Ala Ala Thr Pro Ser Ala Lys Glu Ala Ser Gln
385             390             395             400
```

FIGURE 6D

Glu Asp Asp Asn Asn Asn Val Glu Lys Pro Ser Ser Lys Pro Ala Phe
            405             410                 415

Asn Phe Ile Ser Asn Ala Gly Thr Glu Lys Glu Lys Ser Lys Lys
        420             425             430

Asp Ser Lys Pro Ala Phe Ser Phe Gly Ile Ser Asn Gly Ser Glu Ser
        435             440                 445

Lys Asp Ser Asp Lys Pro Ser Leu Pro Ser Ala Val Asp Gly Glu Asn
    450             455             460

Asp Lys Lys Glu Ala Thr Lys Pro Ala Phe Phe Gly Ile Asn Thr Asn
465             470             475                     480

Thr Thr Lys Thr Ala Asp Thr Lys Ala Pro Thr Phe Thr Phe Gly Ser
            485             490             495

Ser Ala Leu Ala Asp Asn Lys Glu Asp Val Lys Lys Pro Phe Ser Phe
            500             505             510

Gly Thr Ser Gln Pro Asn Asn Thr Pro Ser Phe Ser Phe Gly Lys Thr
        515             520             525

Thr Ala Asn Leu Pro Ala Asn Ser Ser Thr Ser Pro Ala Pro Ser Ile
    530             535             540

Pro Ser Thr Gly Phe Lys Phe Ser Leu Pro Phe Glu Gln Lys Gly Ser
545             550             555             560

Gln Thr Thr Thr Asn Asp Ser Lys Glu Glu Ser Thr Thr Glu Ala Thr
            565             570             575

Gly Asn Glu Ser Gln Asp Ala Thr Lys Val Asp Ala Thr Pro Glu Glu
            580             585             590

Ser Lys Pro Ile Asn Leu Gln Asn Gly Glu Glu Asp Glu Val Ala Leu
        595             600             605

Phe Ser Lys Ala Lys Leu Met Thr Phe Asn Ala Glu Thr Lys Ser Tyr
    610             615             620

Asp Ser Arg Gly Val Gly Glu Met Lys Leu Leu Lys Lys Lys Asp Asp
625             630             635             640

Pro Ser Lys Val Arg Leu Leu Cys Arg Ser Asp Gly Met Gly Asn Val
            645             650             655

Leu Leu Asn Ala Thr Val Val Asp Ser Phe Lys Tyr Glu Pro Leu Ala
            660             665             670

Pro Gly Asn Asp Asn Leu Ile Lys Ala Pro Thr Val Ala Ala Asp Gly
            675             680             685

Lys Thr Tyr Ile Val Lys Phe Lys Gln Lys Glu Glu Gly Arg Ser Phe
    690             695             700

FIGURE 6E

```
Thr Lys Ala Ile Glu Asp Ala Lys Lys Glu Lys
705             710                 715
```

Figure 7

Detection of associations between p27 and p163 in HeLa cells

Precipitation of the total protein of

HeLa cells transfected with

| Precipitation with | CMV-p27 | CMV-p27 + CMV-Nap | CMV-Nap2 | - |
|---|---|---|---|---|
| Nap2-specific antibody | - | + | + | - |
| p27-specific antibody | + | + + | - | - |

FIGURE 8A

Met Ala Lys Arg Val Ala Glu Lys Glu Leu Thr Asp Arg Asn Trp Asp
1           5                   10                  15

Glu Glu Asp Glu Val Glu Glu Met Gly Thr Phe Ser Val Ala Ser Glu
            20                  25                  30

Glu Val Met Lys Asn Arg Ala Val Lys Lys Ala Lys Arg Arg Asn Val
        35                  40                  45

Gly Phe Glu Ser Asp Ser Gly Gly Ala Phe Lys Gly Phe Lys Gly Leu
        50                  55                  60

Val Val Pro Ser Gly Gly Gly Phe Ser Gly Phe Gly Gly Ser Gly
65                  70                  75                  80

Gly Lys Pro Leu Glu Gly Leu Thr Asn Gly Asn Ser Thr Asp Asn Ala
                85                  90                  95

Thr Pro Phe Ser Asn Val Lys Thr Ala Ala Glu Pro Lys Ala Ala Phe
            100                 105                 110

Gly Ser Phe Ala Val Asn Gly Pro Phe Thr Ala Glu Lys Lys Ser Asp
        115                 120                 125

Ala Ala Gln Gly Ala Thr Ser Ala Ser Phe Ser Phe Gly Lys Lys Ile
        130                 135                 140

Glu Ser Ser Ala Leu Gly Ser Leu Ser Ser Gly Ser Leu Thr Gly Phe
145                 150                 155                 160

Ser Phe Ser Ala Gly Ser Ser Ser Leu Phe Gly Lys Asp Ala Ala Gln
                165                 170                 175

Ser Lys Ala Ala Ser Ser Leu Phe Ser Ala Lys Ala Ser Glu Ser Pro
                180                 185                 190

Ala Gly Gly Gly Ser Ser Glu Cys Arg Asp Gly Glu Glu Glu Glu Asn
        195                 200                 205

Asp Glu Pro Pro Lys Val Val Thr Glu Val Lys Glu Glu Asp Ala
    210                 215                 220

Phe Tyr Ser Lys Lys Cys Lys Leu Phe Tyr Lys Lys Asp Asn Glu Phe
225                 230                 235                 240

Lys Glu Lys Gly Val Gly Thr Leu His Leu Lys Pro Thr Ala Thr Gln
                245                 250                 255

Lys Thr Gln Leu Leu Val Arg Ala Asp Thr Asn Leu Gly Asn Ile Leu
            260                 265                 270

Leu Asn Val Leu Ile Ala Pro Asn Met Pro Cys Thr Arg Thr Gly Lys
        275                 280                 285

Asn Asn Val Leu Ile Val Cys Val Pro Asn Pro Pro Leu Asp Glu Lys

FIGURE 8B

```
     290                    295                         300
Gln Pro Thr Leu Pro Ala Thr Met Leu Ile Arg Val Lys Thr Ser Glu
305                 310                 315                 320

Asp Ala Asp Glu Leu His Lys Ile Leu Leu Glu Lys Lys Asp Ala
                    325             330                 335
```

FIGURE 9A

| | | | | | | | | | | | | | |
|---|---|---|---|---|---|---|---|---|---|---|---|---|---|
| Met 1 | Ala | Lys | Arg | Val 5 | Ala | Glu | Lys | Glu | Leu 10 | Thr | Asp | Arg | Asn | Trp 15 | Asp |

```
Met Ala Lys Arg Val Ala Glu Lys Glu Leu Thr Asp Arg Asn Trp Asp
1             5                 10                  15

Glu Glu Asp Glu Val Glu Glu Met Gly Thr Phe Ser Val Ala Ser Glu
            20              25              30

Glu Val Met Lys Asn Arg Ala Val Lys Lys Ala Lys Arg Arg Asn Val
        35              40              45

Gly Phe Glu Ser Asp Ser Gly Gly Ala Phe Lys Gly Phe Lys Gly Leu
    50              55              60

Val Val Pro Ser Gly Gly Gly Phe Ser Gly Phe Gly Gly Ser Gly
65              70              75              80

Gly Lys Pro Leu Glu Gly Leu Thr Asn Gly Asn Ser Thr Asp Asn Ala
            85              90              95

Thr Pro Phe Ser Asn Val Lys Thr Ala Ala Glu Pro Lys Ala Ala Phe
            100             105             110

Gly Ser Phe Ala Val Asn Gly Pro Thr Thr Leu Val Asp Lys Val Ser
        115             120             125

Asn Pro Lys Thr Asn Gly Asp Ser Asn Gln Pro Pro Ser Ser Gly Pro
        130             135             140

Ala Ser Ser Thr Ala Cys Pro Gly Asn Ala Tyr His Lys Gln Leu Ala
145             150             155             160

Gly Leu Asn Cys Ser Val Arg Asp Trp Ile Val Lys His Val Asn Ile
            165             170             175

Asn Pro Leu Cys Asp Leu Thr Pro Ile Phe Lys Asp Tyr Glu Arg Tyr
            180             185             190

Leu Ala Thr Ile Glu Lys Gln Leu Glu Asn Gly Gly Gly Ser Ser Ser
        195             200             205

Glu Ser Gln Thr Asp Arg Ala Thr Ala Gly Met Glu Pro Pro Ser Leu
    210             215             220

Phe Gly Ser Thr Lys Leu Gln Gln Glu Ser Pro Phe Ser Phe His Gly
225             230             235             240

Asn Lys Ala Glu Asp Thr Ser Glu Lys Val Glu Phe Thr Ala Glu Lys
            245             250             255

Lys Ser Asp Ala Ala Gln Gly Ala Thr Ser Ala Ser Phe Ser Phe Gly
            260             265             270

Lys Lys Ile Glu Ser Ser Ala Leu Gly Ser Leu Ser Ser Gly Ser Leu
        275             280             285

Thr Gly Phe Ser Phe Ser Ala Gly Ser Ser Ser Leu Phe Gly Lys Asp
    290             295             300
```

FIGURE 9B

```
Ala Ala Glu Lys Glu Leu
305                   310
```

Figure 10: [SEQ ID NO.: 28]

```
Thr Thr Leu Val Asp Lys Val Ser Asn Pro Lys Thr Asn Gly Asp Ser
1           5               10              15

Asn Gln Pro Pro Ser Ser Gly Pro Ala Ser Ser Thr Ala Cys Pro Gly
            20              25              30

Asn Ala Tyr His Lys Gln Leu Ala Gly Leu Asn Cys Ser Val Arg Asp
        35              40              45

Trp Ile Val Lys His Val Asn Thr Asn Pro Leu Cys Asp Leu Thr Pro
    50              55              60

Ile Phe Lys Asp Tyr Glu Arg Tyr Leu Ala Thr Ile Glu Lys Gln Leu
65          70              75                          80

Glu Asn Gly Gly Gly Ser Ser Ser Glu Ser Gln Thr Asp Arg Ala Thr
            85              90              95

Ala Gly Met Glu Pro Pro Ser Leu Phe Gly Ser Thr Lys Leu Gln Gln
            100             105             110

Glu Ser Pro Phe Ser Phe His Gly Asn Lys Ala Glu Asp Thr Ser Glu
        115             120             125

Lys Val Glu Phe
        130
```

Figure 11:

GUC sequences in p163

Nucleotide position       Sequence

| 422-424 | GGAA | GTC | ATGA | |
|---------|------|-----|------|---|
| 818-820 | CTCC | GTC | CGCG | |
| 1021-1023 | AAGA | GTC | ACCA | |
| 1287-1289 | GAGA | GTC | CGGC | |
| 1586-1588 | CAAC | GTC | CTTA | |
| 1595-1597 | TATC | GTC | TGTG | |
| 1601-1603 | CTGT | GTC | CCCA | | in EST 62312 (human)

Nucleotide position       Sequence
Amino acid

| 212-214 | GACT | GTC | GAAT | 87 |
|---------|------|-----|------|----|
| 358-360 | GACA | GTC | AGCA | 136 |
| 402-404 | TTGT | GTC | GGAA | 150 |

The interacting domain comprises amino acids 121-252 of the mouse sequence, to which the numbering relates. This corresponds to nucleotides 685-1078 of the mouse sequence.

Figure 12a:

5 selected primer pairs

| Score | Length | GC% | Locus | Name | 5` 3` |
|---|---|---|---|---|---|
| 5.8 | 108 | 43.5 | 122..143 | above: | AGAAAGCAAAGCGCAGAAATGT [SEQ ID NO.: 29] |
| | | | 229..209 | below: | CAAATCCAGAAAAGCGTCCTC [SEQ ID NO.: 30] |
| 6.7 | 119 | 42.0 | 104..127 | above: | TGAAGAATAGAGCCATAAAGAAAG [SEQ ID NO.: 31] |
| | | | 240..220 | below: | AGAAAAGCGTCCTCCTCCAGA [SEQ ID NO.: 32] |
| 23.3 | 137 | 43.8 | 104..127 | above: | TGAAGAATAGAGCCATAAAGAAAG [SEQ ID NO.: 33] |
| | | | 204..220 | below: | AGCGCCACTAACCAAATCCAGA [SEQ ID NO.: 34] |
| 25.7 | 100 | 44.0 | 122..143 | above: | AGAAAGCAAAGCGCAGAAATGT [SEQ ID NO.: 35] |
| | | | 221..200 | below: | GAAAAGCGTCCTCCTCCAGAAG [SEQ ID NO.: 36] |
| 48.7 | 122 | 46.7 | 123..144 | above: | GAAAGCAAAGCGCAGAAATGTT [SEQ ID NO.: 37] |
| | | | 244..224 | below: | CTCCAGCGCCACTACCAAATC [SEQ ID NO.: 38] |

Figure 12b:

One selected primer pair

| Score | Length | GC% | Locus | Name | 5` | 3` |
|---|---|---|---|---|---|---|
| 51.3 | 193 | 52.8 | 34..53 | above: | CCCGCACGGAGCAGTTCAAG [SEQ ID NO.: 39] | |
| | | | 226..205 | below: | GCAGCGGCAGATCCCAAGGTAG [SEQ ID NO.: 40] | |

Figure 12c:

One selected primer pair

| Score | Length | GC% | Locus | Name | 5` | 3` |
|---|---|---|---|---|---|---|
| 2.4 | 136 | 45.6 | 4. .20 | above: | GGCATCCTTTTTCTCCA | [SEQ ID NO.: 41] |
| | | | 139. .120 | below: | CGTTCTTATCGTCTCTGTGTTC | [SEQ ID NO.: 42] |
| 2.5 | 120 | 45.0 | 5. .23 | above: | GCATCCTTTTTCTCCAGTA | [SEQ ID NO.: 43] |
| | | | 139. .119 | below: | TGTTCCAAATCCACCAAT | [SEQ ID NO.: 44] |
| 2.7 | 100 | 48.0 | 40. .58 | above: | GTCTGCATCCTCGCTGGTT | [SEQ ID NO.: 45] |
| | | | 139. .119 | below: | CGTTCTTATCGTCTGTGTTCC | [SEQ ID NO.: 46] |
| 50.0 | 105 | 44.8 | 57. .75 | above: | TTTTACCCGAATCAACAT | [SEQ ID NO.: 47] |
| | | | 161. .141 | below: | GTACGCGAACAGGGAAGAATA | [SEQ ID NO.: 48] |

Figure 13: Summary of the growth experiments

|  | Cyclin D1 | | Nup2 | |
|---|---|---|---|---|
|  | non-selective | selective | non-selectiv | selective |
| wt p27 | + + + | + + + | + + + | + + + |
| Mut 106 | + + + | + + + | + + + | + + + |
| Mut 152 | + + + | + | + + + | + |
| Mut 294 | + + + | + + + | + + + | - |
| Mut 660 | + + + | + + + | + + + | - |
| Mut 687 | + + + | - | + + + | - |
| Mut 826 | + + + | + + + | + + + | + + + |
| Mut 850 | + + + | + + + | + + + | - |

FIGURE 14A

```
         - - - - R V S N G S P S L E R M D A R Q A D H P K P S A C R N L F G P V N H G E         Majority
                       10                  20                  30                  40
  1      - - - - - - - - - - - - - M D A R Q A D H P K P S A C R N L F G P V N H G E             Clone#106 Protein
  1      - - - R V S N G S P S L R M D A R Q A D H P K P S A C R N L F G P V N H G E             Clone#152 Protein
  1      - - - - R V S N G S P S L E R M D A R Q A D H P K P S A C R N L F G P V N H G E         Clone#294 Protein
  1      - - - - - V S N G S P S L E R M D A R Q A D H P K P S A C R N L F G P V N H G E         Clone#660 Protein
  1      - - N V R V S N G S P S L E R M D A R Q A D H P - P S A C R N L F G P V N H G           Clone#687 Protein
  1      - - - - - - - - - - - - - M D A R Q A D H P K P S A C R N L F G P V N H G E             Clone#826 Protein
  1      - - - - - - - - - - - - - M D A R Q A D H P K P S A C R N L F G P V N H G E             Clone#850 Protein
  1      M S N V R V S N G S P S L E R M D A R Q A D H P K P S A C R N L F G P V N H E E         Mouse p27 AS L T R D L E K H C R D M E E A S Q R K W N F D F Q N H K P L E G R Y E W Q E V E         Majority
                       50                  60                  70                  80
 26      L T R D L E K H C R D M E E A S Q R K W N F D F Q N H K P L E G R Y E W Q E V E         Clone#106 Protein
 37      L T R D L E K H C R D M E E A S Q H K W N F D F Q N H R L E G R Y E W Q E V E           Clone#152 Protein
 37      L T R D L E K H C R D M E E A S Q R K W N F D F Q N H K P L E G R Y E W Q E V E         Clone#294 Protein
 36      L T R D L E K H C R D M E E A S Q R K W N F D F Q N H K P L E G R Y E W Q E V E         Clone#660 Protein
 38      E L T R D L E K H C R D M E A S Q R K W N F D F Q N H K P L E G R Y E W Q E V           Clone#687 Protein
 26      L T R D L E K H C Q M E E A S Q R K W N F D F Q N H K P L E G R Y E W Q E V E           Clone#826 Protein
 26      L T R D L E K H C R D M E E A S Q R K W N F D F Q N H K P L E G R Y E W Q E V E         Clone#850 Protein
 41      L T R D L E K H C R D M E E A S Q R K W N F D F Q N H K P L E G R Y E W Q E V E         Mouse p27 AS R G S L P E F Y Y R P P R P P P K S A C K V L A Q E S Q D V S G S R Q A V P L I G       Majority
                       90                  100                 110                 120
 66      R G S L P E F Y Y R P P C P P K S A C K V L A Q E S Q D V S G S R Q A V P L I G         Clone#106 Protein
 77      R G S L P E F Y Y R P P R P P K S A C K V L A Q E S Q D V S G S R Q A V P L I G         Clone#152 Protein
 77      R G S L P E F Y Y G P P R P P K S A C K V L A Q E S Q D V G G S R Q A V P L I G         Clone#294 Protein
 76      R G S L P E F Y Y G P P R P P K S A C K V L A Q E S Q D V S G S R Q A V P L I G         Clone#660 Protein
 78      R G S L P E F Y Y R P P R P P K S A C K V P A Q E S Q D V S G S R Q A V P L I           Clone#687 Protein
 66      R G S L P E F Y Y R P P R P P K S A C K V L A Q E S Q D V S G S R Q A V P L I G         Clone#826 Protein
 66      R G S L P E F Y Y G P P R P P K S A C K V L A Q E S Q D V S G S R Q A V P L I G         Clone#850 Protein
 81      R G S L P E F Y Y R P P R P P K S A C K V L A Q E S Q D V S G S R Q A V P L I G         Mouse p27 AS S Q A N S E D R H L V D Q M P D S S D N Q A G L A E Q C P G M R K R P A A E D S         Majority
                       130                 140                 150                 160
106      S Q A N S E D R H L V D Q M P D S S D N Q A G L A E Q C P G M R K R P A A E D S         Clone#106 Protein
117      S Q A N S E D R H L V D Q M P D S S D N Q A G L A E Q C P G M R K R P A A E D S         Clone#152 Protein
117      S Q A N S E D R H L V D Q M P D S S D N Q A G L A E Q C P G M R K R P A A E D S         Clone#294 Protein
116      S Q A N S E D R H L V D Q M P D S S D N Q A G L A E Q C P G M R K R P A A E D S         Clone#660 Protein
118      G S Q A N S E D R H L V D Q M P D S S D N Q A G L A E Q C P G M R K R P A A E D         Clone#687 Protein
106      S Q A N S E D R H L V D Q M P D S S D N Q A G L A E Q C P G M R K R P A A E D S         Clone#826 Protein
106      S Q A N S E D R H L V D Q M P D S S D S Q A G L A E Q C P - - - - - - - - - -           Clone#850 Protein
121      S Q A N S E D R H L V D Q M P D S S D N Q A G L A E Q C P G M R K R P A A E D S         Mouse p27 AS S S Q I K R A N R T E E N V S D G S P N A G T V E Q T P K K P G L R R Q T R - -         Majority
                       170                 180                 190
146      S S Q I K R A N R T E E N V S D G S P N A G T V E Q T P K K P G L R - - - R -           Clone#106 Protein
157      S S Q I K R A N R T E E N V S D G S P N A G T V E Q T P K K P G P R Q T R - .           Clone#152 Protein
157      S S Q I K R A N R T E E N V S D G S P N A G T V E Q T P K K P G L R R Q T R - .         Clone#294 Protein
156      S S Q I K R A N R T E E N V S D G S P N A G T V E Q T P K K P G L R R Q T R - .         Clone#660 Protein
158      S S Q I K R A N R T E N V S D G S P N A G T V E Q T P K K G L R R Q T - R             Clone#687 Protein
146      S S Q I K R A N R T E E N V S D G S P N A G T V E Q T P K K P G L R - - - R -           Clone#826 Protein
135      - - - - - - - - - - - - - - - - - - - - - - - - - - - - - - - - - - - - G -           Clone#850 Protein
161      S S Q N K R A N R T E E N V S D G S P N A G T V E Q T P K K P G L R R Q T               Mouse p27 AS V D L Q P - S - F R A N - F L - F M I F - - I - - - - - - K - - -                       Majority
```

FIGURE 14B

| Sequence | SEQ ID NO.: |
|---|---|
| Majority | 49 |
| Clone # 106 | 50 |
| Clone # 152 | 51 |
| Clone # 294 | 52 |
| Clone # 660 | 53 |
| Clone # 687 | 54 |
| Clone # 826 | 55 |
| Clone # 850 | 56 |
| p27 (Mouse) | 57 |

(12) United States Patent US 6,265,562 B1

NUCLEIC ACID CONSTRUCTS WHOSE ACTIVITY IS AFFECTED BY INHIBITORS OF CYCLIN-DEPENDENT KINASES AND USES THEREOF

INFORMATION ON RELATED APPLICATIONS

The present application claims the priority benefit, under 35 U.S.C. §119, of Federal Republic of Germany Application No. 19756975.7, filed Dec. 20, 1997.

BACKGROUND OF THE INVENTION

The cell cycle of eukaryotic cells is controlled by cyclin-dependent kinases (cdks); these are kinases which require a regulatory subunit ("cyclin") in order to be active. Different processes in the cell cycle (such as replication and entry into mitosis) are controlled by different cdks (Morgan, Nature 374, 131 (1995)). In association with this, the activity of cyclin-dependent kinases is subject to a high degree of regulation. In this context, internal control mechanisms exist which, for example, prevent entry into mitosis until the DNA has completed its replication. Control by external factors, such as growth factors, only occurs before DNA replication begins; replication is initiated by active cyclin E/cdk2 complexes.

In addition to the quantity of cyclin in the kinase subunit, the activity of cyclin-dependent kinases is also regulated by small inhibitor proteins (Sherr and Roberts, Gene Dev. 9, 1149 (1995)). For example, two inhibitors, which are designated p21 and p27 in accordance with their size, are crucial for cyclin E/cdk2.

The cyclin E/cdk2 kinase is normally inactive in cells which are expressing high quantities of p27, and the entry into DNA replication is blocked.

While positive cell cycle regulators are overexpressed or at least expressed constitutively in many human tumors (Sherr, Science 274, 1672 (1996)), negative regulators are frequently mutated or only weakly expressed (Fero et al., Cell 85, 733 (1996)). Specific correlations exist: for example, the cyclin D1 gene is found to be overexpressed in many neck tumors. The hope therefore exists that cyclin-dependent kinases, and their function, might be target structures in the search for novel, selective substances which have an antiproliferative effect.

The gene for the p27 protein has been known for some years (K. Polyak et al. Cell 78, 59–66 (1994)) and is available in Genbank [murine p27; accession number K 09968; human p27: K 10906]. Despite intensive searching, mutations in the p27 gene have not so far been found in human tumors. This is all the more surprising since mice in which the gene for p27 has been inactivated exhibit a phenotype with multiple dysplasias and an increased incidence of tumors (Fero et al., Cell 85, 733 (1996), Kiyokawa et al., Cell 85, 721 (1996)). Instead of this, the function of p27 is evidently in the main regulated posttranscriptionally.

Thus, p27 is degraded by proteolysis; this also occurs at the beginning of DNA replication in normal cells. The ability to degrade p27 proteolytically is markedly increased in many tumors, as compared with the normal tissue, and this appears to correlate directly with an unfavorable prognosis (Loda et al., Nature Med. 3, 231 (1997)).

However, there must also be other mechanisms as well which are able to lead to p27 inactivation. For example, after cells have been transformed with the Myc oncogene, p27 is first of all inactivated functionally (i.e. it no longer binds to cyclin/cdk complexes) and is only degraded at a much later stage. It has not so far been possible to understand why large quantities of p27 proteins are expressed in a number of breast tumors, for example, and these tumors nevertheless grow very rapidly. The mechanisms which inactivate p27 in these tumors are so far unknown (Fredersdorf et al., Proc. Natl. Acad. Sci. USA 94, 6380 (1997)).

There is consequently a great interest among experts in finding mechanisms or substances which are responsible for inactivating p27 in tumors. The present invention has solved this problem. The protein p163, which is described in the application, can bind p27, can inhibit the function of p27 and can lead p27 to proteolysis in the cytoplasm.

SUMMARY OF THE INVENTION

The present invention relates to nucleic acid constructs comprising (a) a first activation sequence; (b) a transcription factor gene, the transcription of which is induced by activation of the first activation sequence, comprising (1) an activation domain, (2) a sequence for binding an inhibitor, and (3) a DNA-binding domain; (c) a second activation sequence that is activated by binding the expression product of the transcription factor gene; and (d) an effector gene, the transcription of which is induced by the activation of the second activation sequence. In one embodiment of the invention, the first activation sequence and the second activation sequence are the same.

The first activation sequence may be activated non-specifically, cell-specifically, metabolically specifically, virus--specifically and/or cell cycle-specifically. Examples of first activation sequence include promoters which are activated in endothelial cells, peritoneal cells, pleural cells, epithelial cells of the skin, epithelial cells of the lung, epithelial cells of the gastrointestinal tract, epithelial cells of the kidney, epithelial cells of the urinary tracts, muscle cells, connective tissue cells, hematopoietic cells, macrophages, lymphocytes, leukemia cells, tumor cells or glia cells; promoter sequences of viruses; promoter or enhancer sequences which are activated by hypoxia or cell cycle-specific activation sequences of the genes for cdc25C, cyclin A, cdc2, E2F-1, B-myb, or DHFR; and sequences for binding transcription factors which appear or are activated in a cell proliferation-dependent manner.

According to one aspect of the present invention, the activation domain of the transcriptional factor gene may be at least one of the activation domains of Oct-2, Sp1, NFY, ITF-2, VP-16, c-Myc or CTF. According to another aspect of the invention, the sequence for binding an inhibitor encodes an inhibitor of protein p27. In one embodiment, the inhibitor of protein p27 is protein p163 protein or a homologue, derivative, or part thereof. Derivatives of the include those comprising a deletion or mutation in the p27- or Ran-binding domain. In one embodiment, the inhibitor of protein p27 is the p27-binding domain of protein p163. In another embodiment, the inhibitor is a human p163 protein or a homologue, derivative or part thereof. In still another embodiment, the inhibitor is an antibody or antibody fragment that binds to p163 protein.

In another aspect of the present invention, the second activation sequence comprises at least one DNA sequence for binding the transcription factor.

In yet another aspect of the present invention, the effector gene encodes an active compound selected from the group consisting of cytokines, chemokines, growth factors, receptors for cytokines, chemokines or growth factors, proteins having an antiproliferative or cytostatic or apoptotic effect, antibodies, antibody fragments, angiogenesis inhibitors, peptide hormones, coagulation factors, coagulation inhibitors, fibrinolytic proteins, peptides or proteins having an effect on the blood circulation, blood plasma proteins and antigens of infectious pathogens or of cells or of tumors, with the selected antigen bringing about an immune reaction. In one embodiment, the effector gene encodes an enzyme which converts a precursor of a drug into a drug. In another embodiment, the effector gene encodes a ligand-active compound fusion protein or a ligand-enzyme fusion protein, wherein the ligand is selected from the group consisting of cytokines, growth factors, antibodies, antibody fragments, peptide hormones, mediators, and cell adhesion molecules.

The present invention also relates to vectors and isolated cells comprising the nucleic acid constructs The present invention further relates to methods of treating or preventing a disease, comprising administering to a patient a nucleic acid construct or isolated cell according to present invention. The disease treated or prevented can be, for example, infections, tumors, leukemias, autoimmune diseases, allergies, arthritides, inflammations, organ rejections, graft versus host reactions, blood coagulation diseases, circulatory diseases, anemia, hormonal diseases and damage to the CNS. The nucleic acid construct can be administered externally, perorally, intravesicularly, nasally, intrabronchially or into the gastrointestinal tract, or injected into an organ, into a body cavity, into the musculature, subcutaneously or into the blood circulation. The isolated cell can be administered externally, intravesicularly, nasally, intrabronchially, orally or into the gastrointestinal tract, or injected into an organ, into a body cavity, into the musculature, subcutaneously or into the blood circulation.

The present invention further relates to a method of making a nucleic acid construct, comprising ligating the elements of the construct together stepwise.

BRIEF DESCRIPTION OF THE FIGURES

FIG. 1: FIG. 1 summarizes the interaction of p163 in yeast specifically with p27, and not with other proteins such as Myc, Max, Bc1-6 or prothymosin-α. FIG. 1 also shows a first delimitation of the domains of p27 in which the interaction with p163 takes place. These data indicate that p163 binds to the same domains in p27 as do cyclin-dependent kinases (Russo et al., Nature 382, 325 (1996)).

FIG. 2: FIG. 2 summarizes experimental results indicating that recombinant, in-vitro synthesized $^{35}$S-labeled p27 binds selectively to a column which is loaded with a chimeric GST-p163 fusion protein but not to a column which is loaded with the same quantity of GST. FIG. 2 also shows that p27 from a cell extract binds inefficiently to GST-p163; in this extract, p27 is bound to complexes of cyclin-dependent kinases.

FIG. 3: FIGS. 3A and 3B depict the nucleic sequence (SEQ ID NO: 9) according to the invention, which encodes the murine p163 protein.

FIG. 4: FIG. 4 is a comparison of certain domains of p163 (SEQ ID NOS 10, 12, 14, 16 & 18) and Ynup2 (SEQ ID NOS 11, 13, 15, 17 & 19). FIG. 4 shows that several functional domains are conserved, although, taken as a whole, the homology is not high.

FIG. 5: FIG. 5 is a comparison of the sites for binding a regulatory protein (Ran, a GTP-binding protein) which regulates nuclear transport. FIG. 5 show the biding site conservation between Ran-binding protein (RBP-1) (SEQ ID NOS 20 and 21), NuP-2 (SEQ ID NO: 22) 5and p163 (SEQ ID NO: 23).

FIG. 6: FIGS. 6A–6B show amino acid sequences from mouse p163 (SEQ ID NO: 24) and Yeast Nup2 (SEQ ID NO: 25).

FIG. 7: FIG. 7 demonstrates the association between p27 and Nup2 using in each case a polyclonal antibody against Nup2 and a polyclonal antibody against murine p27. The p27 protein was only precipitated satisfactorily when p163 was expressed.

FIG. 8: FIGS. 8A and 8B show an example of a dominant negative mutant of p163 (SEQ ID NO: 26) in which the p27-binding domain is deleted.

Figure 9B:
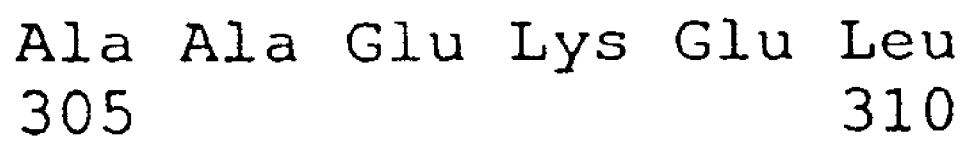

FIG. 9: FIGS. 9A and 9B show an example of a dominant negative mutant of p163 (SEQ ID NO: 27) in which p163 which lacks the Ran-binding domain.

FIG. 10: FIG. 10 depicts the p27 binding domain of p163 (SEQ ID NO: 28).

FIG. 11: FIG. 11 lists examples of nucleotide sequences of the p163 protein which can be cleaved by ribozymes.

FIG. 12: FIGS. 12a (SEQ ID NOS 29–38, respectively, in order of appearance), 12b, (SEQ ID NOS 39 & 40, respectively, in order of appearance), and 12c (SEQ ID NOS 41–48, respectively, in order of appearance) depict PCR primer pairs according to the present invention.

FIG. 13: FIG. 13 shows a range of phenotypes for p27 mutants created.

FIG. 14: FIGS. 14A and B show the sequences (SEQ ID NOS, 49–57 respectively, in order of appearance) of mutated p27 proteins as compared with the wild type.

FIG. 15 represents a nucleic acid construct according to the invention.

DETAILED DESCRIPTION OF THE INVENTION

Figure 15:
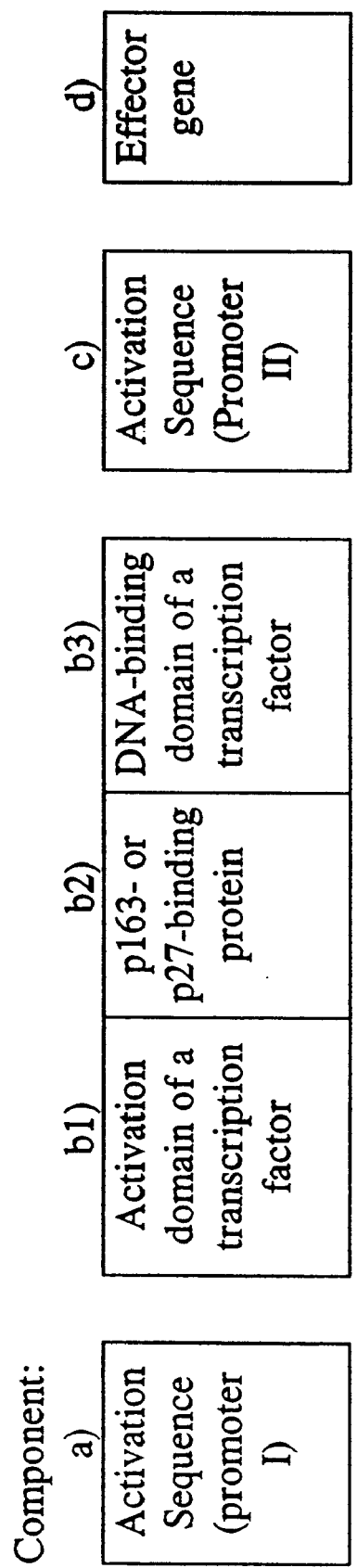
FIG. 15.

The term "isolated" as used herein refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid.

"Variants," according to the invention, include DNA and/or protein molecules that resemble, structurally and/or functionally, those set forth in herein. Variants may be isolated from natural sources, may be entirely synthetic or may be based in part on both natural and synthetic approaches. Variants include analogs, homologues, derivatives, and mutants of the nucleotide and amino acid sequences disclosed herein.

One type of variant according to the present invention is a homologue. A homologue is a variant that is isolated from natural sources. Examples of homologues according to the present invention include proteins and nucleotide sequences encoding proteins that possess the ability to bind to and inhibit the function of p27 isolated from a mammal, such as a human.

Another aspect of the present invention provides "degenerate variants" of the nucleic acid fragments of the present invention. A "degenerate variant" is a nucleotide fragment which differs from a disclosed nucleotide sequence, but due to the degeneracy of the genetic code, encodes an identical polypeptide sequence.

Given the known relationship between DNA sequences and the proteins they encode, degenerate variants typically are described by reference to this relationship. It is well known that the degeneracy of the genetic code results in many possible DNA sequences which encode a particular protein. Indeed, of the three bases which comprise an amino acid-encoding triplet, the third position, and often the second, almost always may vary. This fact alone allows for a class of variant DNA molecules which encode protein sequences identical to those disclosed herein, yet have about 30% sequence variation. In other words, the variant DNA molecules are about 70% identical to the inventive DNAs, having no additional or deleted sequences. Thus, one aspect of the invention provides degenerate variant DNA molecules encoding the inventive protein sequences.

In one embodiment, these variants have at least about 70% sequence identity with the DNA molecules described herein. In a preferred embodiment, these variants have at least about 80% sequence identity with the DNA molecules described herein. In a more preferred embodiment these variants have at least about 90% sequence identity with the DNA molecules described herein.

Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved. These variants are termed conservative amino acid variants.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)–(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Other DNA variants within the invention also may be described by reference to their physical properties in hybridization. One skilled in the field will recognize that DNA can be used to identify its complement and, since DNA is double stranded, its equivalent or homologue, using nucleic acid hybridization techniques. It will also be recognized that hybridization can occur with less than 100% complementarity. However, given appropriate choice of conditions, hybridization techniques can be used to differentiate among DNA sequences based on their structural relatedness to a particular probe. For guidance regarding such conditions see, for example, Sambrook et al., 1989, MOLECULAR CLONING, A LABORATORY MANUAL, Cold Spring Harbor Press, N.Y.; and Ausubel et al., 1989, CURRENT PROTOCOLS IN MOLECULAR BIOLOGY, Green Publishing Associates and Wiley Interscience, N.Y.

Structural relatedness between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding.

Hybridization usually is done in two stages. First, in the "binding" stage, the probe is bound to the target under conditions favoring hybridization. Stringency is usually controlled at this stage by altering the temperature. For high stringency, the temperature is usually between 65° C. and 700° C., unless short (<20 NT) oligonucleotide probes are used. A representative hybridization solution comprises 6×SSC, 0.5% SDS, 5×Denhardt's solution and 100μg of non-specific carrier DNA. See Ausubel et al., supra, section 2.9, supplement 27 (1994). Of course many different, yet functionally equivalent, buffer conditions are known. Where the degree of relatedness is lower, a lower temperature may be chosen. Low stringency binding temperatures are between about 250° C. and 400° C. Medium stringency is between at least about 40° C. to less than about 65° C. High stringency is at least about 650° C.

Second, the excess probe is removed by washing. It is at this stage that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 600° C.

In a general sense, the preferred DNA variants of the invention are those that retain the closest relationship, as described by "sequence identity" to the DNA molecules described herein. According to another aspect of the invention, therefore, substitutions, insertions, additions and deletions of defined properties are contemplated. It will be recognized that sequence identity between two polynucleotide sequences, as defined herein, generally is determined with reference to the protein coding region of the sequences. Thus, this definition does not at all limit the amount of DNA, such as vector DNA, that may be attached to the molecules described herein. Preferred DNA sequence variants include molecules encoding proteins sharing some or all of the biological activity of the native molecule.

"Substitutions" generally refer to alterations in the DNA sequence which do not change its overall length, but only alter one or more nucleotide positions, substituting one for another in the common sense of the word. One class of preferred substitutions, "degenerate substitutions," are those that do not alter the encoded amino acid sequence. Preferred substitutions retain at least about 70% identity, more preferably at least 70% identity, with the DNAs described herein. Some more preferred molecules have at least about 80% identity, more preferably at least 80% identity. Particularly preferred DNAs share at least about 90% identity, more preferably at least 90% identity,.

"Insertions," unlike substitutions, alter the overall length of the DNA molecule, and thus sometimes the encoded protein. Insertions add extra nucleotides to the interior (not the 5' or 3' ends) of the subject DNAs. Preferred insertions are made with reference to the protein sequence encoded by the DNA. Thus, it is most preferred to provide an insertion in the DNA at a location that corresponds to an area of the encoded protein which lacks structure. For instance, it typically would not be beneficial, if the preservation of biological activity is desired, to provide an insertion within an alpha-helical region or a beta-pleated sheet. Accordingly, non-structural areas, such as those containing helix-breaking glycines and proline residues, are most preferred sites of insertion. Other preferred sites of insertion are the splice sites, which are indicated above in the description of the inventive DNA molecules.

While the optimal size of insertions will vary depending upon the site of insertion and its effect on the overall conformation of the encoded protein, some general guides are useful. Generally, the total insertions (irrespective of their number) should not add more than about 30% (or preferably not more than 30%) to the overall size of the encoded protein. More preferably, the insertion adds less than about 10–20% (yet more preferably 10–20%) in size, with less than about 10% being most preferred. The number of insertions is limited only by the number of suitable insertions sites, and secondarily by the foregoing size preferences.

"Additions," like insertions, also add to the overall size of the DNA molecule, and usually the encoded protein. However, instead of being made within the molecule, they are made on the 5' or 3' end, usually corresponding to the N- or C-terminus of the encoded protein. Unlike deletions, additions are not very size-dependent. Indeed, additions may be of virtually any size. Preferred additions, however, do not exceed about 100% of the size of the native molecule. More preferably, they add less than about 60 to 30% to the overall size, with less than about 30% being most preferred.

"Deletions" diminish the overall size of the DNA and, therefore, also reduce the size of the protein encoded by that DNA. Deletions may be made from either end of the molecule or internal to it. Typical preferred deletions remove discrete structural features of the encoded protein. For example, some deletions will comprise the deletion of one or more exons, described above, which may define a structural feature.

Another type of variant according to the present invention are mutants of the disclosed nucleotides or proteins. Site-specific and region-directed mutagenesis techniques can be employed to effect changes in the peptides employed according to the invention. See CURRENT PROTOCOLS IN MOLECULAR BIOLOGY vol. 1, ch. 8 (Ausubel et al. Eds., J. Wiley & Sons 1989 & supp. 1990–93); PROTEIN ENGINEERING (Oxener & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra.

Yet another type of variant according to the present invention are derivatives of the disclosed nucleotides and proteins. "Derivative" as used herein connotes a degree of similarity that is sufficient to indicate the original nucleotide or protein from which the derived nucleotide or protein, or portions thereof, where obtained. Typically, the nucleotide or protein that is "derived" is obtained from or based upon a naturally-occurring nucleotide or protein or other source nucleotide or protein, such as mutants of naturally-occurring nucleotides and proteins and nucleotide and polypeptide sequences modeled upon rules developed through analyses of families of nucleotides or proteins, as well as the characteristics of individual amino acids.

The present invention also contemplates fragments of the nucleotides and proteins disclosed herein. A fragment, as used herein, refers to portions of an amino acid sequence or nucleotide sequence. A protein or peptide fragment can be generated directly from the peptides themselves by chemical cleavage, by proteolytic enzyme digestion, or by combinations thereof. Additionally, such fragments can be created by recombinant techniques employing genomic or cDNA cloning methods. Furthermore, methods of synthesizing polypeptides directly from amino acid residues also exist. Preferably, the protein fragment retains the biological activity of the protein from which it is derived. Thus, a fragment according to the present invention will retain the ability to bind to and inhibit the function of p27.

As used herein, "sequence identity" between two polypeptide sequences indicates the percentage of amino acids that are identical between the sequences. "Sequence similarity" indicates the percentage of amino acids that either are identical or that represent conservative amino acid substitutions.

A. General Description of the Invention

The present application relates to a protein which inhibits the cellular protein p27 and thereby relieves the inhibition of the proliferation of the cell which is brought about by p27, to mutants thereof, some of which have a dominant interfering character, to the corresponding nucleic acids which encode these proteins, and to the use of protein and nucleic acids for the prophylaxis and therapy of diseases. The nucleic acid constructs of the present invention can be used in screening for antiproliferative drugs, for example inhibitors of p27/p163 interaction. In addition, the nucleic acid constructs of the present invention can be used for the expression of p163 deletion mutants that can be used as dominant negative mutants of naturally occurring p163. Furthermore, nucleic acid constructs of the present invention can be used for the gene therapy of diseases and thus for the prophylaxis and therapy of diseases.

1. Protein p163 and its Nucleic Acid Sequence

The invention relates to a novel protein, termed p163, which binds p27 and thereby inhibits its function and leads it to proteolysis in the cytoplasm. The amino acid sequence of this protein has been determined.

Protein p163 binds specifically to p27 and not to other proteins such as Myc, Max, Bc1-6 or prothymosin-α.

The invention furthermore relates to a nucleotide sequence which encodes protein p163. This nucleotide sequence has been determined in the case of the mouse p163 protein and, by sequence comparison, also in the case of the human p163 protein.

2. Dominant Negative p163 Analogs

This invention furthermore relates to nucleotide sequences which encode constituent peptides of p163 and/or encode proteins which are analogs of p163 and which exert a dominant negative effect, i.e. which inhibit the binding of the natural p163 protein to protein p27 without substantially impairing the binding of the p27 protein to cyclin E/cdk2 and the inhibition of cyclin E/cdk2 which is thereby brought about.

The invention furthermore relates to the use of nucleic acid sequences which encode dominant negative mutants of the p163 protein, or constituent sequences thereof, with the use comprising the introduction of these nucleic acid sequences into a target cell and the inhibition of the binding between the target cell-specific p163 protein and the target cell-specific p27 protein, such that the proliferation of the target cell is inhibited by the target cell-specific p27 protein which is thereby released.

3. Peptides Which Inhibit p163

However, this invention also relates to nucleotide sequences which encode proteins or peptides which inhibit the function of p163. These include proteins or peptides which bind to the site in the p163 protein for binding the p27 protein or which bind to the site in the p163 protein for binding Ran (Loeb et al. Mol. Cell. Biol. 4, 209–222 (1993)) and thereby inhibit the p163 protein which is internal to the cell.

These proteins include peptides which correspond to the site in the p27 protein or the site in the Ran protein for binding the p163 protein. These proteins furthermore include antibodies or antibody cleavage products, such as $F(ab)_2$, Fab, Fv and scFv, which possess specificity against protein p163, in particular against its site for binding the p27 protein.

The invention furthermore relates to the use of nucleic acid sequences which encode such inhibitory proteins or peptides, with the use comprising the introduction of these nucleic acid sequences into a target cell and the inhibition of the binding between the target cell-specific p163 protein and the target cell-specific p27 protein or the target cell-specific Ran protein, such that the proliferation of the target cell is inhibited by the target cell-specific p27 protein which is thereby released.

4. Use of p163 for Stimulating Cell Division

This invention furthermore relates to the use of the nucleotide sequence which encodes the p163 protein, or the p163 protein itself, for inhibiting the p27 protein which is internal to the cell and thus for stimulating the cell division of a target cell.

5. Inhibition of Transcription and Translation of p163

However, the invention also relates to nucleic acid sequences which inhibit the transcription and/or translation of the target cell-specific nucleic acid sequence which encodes the p163 protein and thereby lead to the p27 protein being released and consequently to inhibition of the proliferation of the target cell. Such nucleic acid sequences according to the invention can, for example, be antisense (triple) DNA, antisense RNA and/or ribozymes.

6. Test systems for Finding p163 Inhibitors

The invention furthermore relates to the use of the nucleic acid sequence which encodes the p163 protein, or of constituent sequences thereof, for test systems which search for inhibitors of the binding between the p163 protein and the p27 protein or the Ran protein, and to the use of the inhibitors of the p163 protein which are found in these test systems for inhibiting the proliferation of a target cell.

7. Detecting p163 for Diagnosing a Disease

The invention furthermore relates to the use of nucleic acid constructs which encode the p163 protein, or which encode constituent sequences of the p163 protein, or of nucleic acid sequences or protein sequences which bind to these nucleic acid sequences for the p163 protein, or of proteins which bind to the p163 protein, for detecting nucleic acids which encode p163 or for detecting the p163 protein in a cell or a tissue or a body fluid for the purpose of ascertaining the proliferation state of a cell or of a tissue, or of diagnosing a disease state.

8. Expression Systems Which Comprise Sequences for Binding p27 or p163/p27 Protein Complexes The invention furthermore relates to an expression system which comprises a nucleic acid sequence whose expression is controlled by the p27 protein and which, in the simplest case, contains the following components:

Component a)
    at least one activation sequence (promoter No. I)

Component b)
    at least one gene for a transcription factor which is composed of a fusion protein which contains
        Component $b_1$)
            at least one activation domain of a transcription factor
        Component $b_2$)
            1) at least one sequence or at least one constituent sequence of the p163 protein to which the p27 protein binds, or
            2) at least one antibody or at least one antibody fragment, such as Fab, Fv or scFv, which binds to the site in the p27 protein for binding the p163 protein, or
            3) at least one antibody or at least one antibody fragment, such as Fab, Fv or scFv, which binds to the site in the p163 protein for binding the p27 protein, or
            4) at least one antibody or at least one antibody fragment, such as Fab, Fv or scFv, which binds to the complex composed of p163 and p27.
        Component $b_3$)
            at least one DNA-binding domain of a transcription factor Component c)
    at least one activation sequence (promoter No. II) which is activated by binding the transcription factor which is encoded by component b)

Component d)
    at least one effector gene.

The arrangement of the individual components is depicted, by way of example, in FIG. 1. A prerequisite for the functional capability, according to the invention, of the expression system is that component $b_2$1), $b_2$2) or $b_2$3) is placed between, or added onto, components $b_1$) and $b_3$) such that the binding of the p27 protein or of the p163 protein to the expression product of component $b_2$) inhibits the functional capability of the activation domain [component $b_2$)] and/or of the DNA-binding domain [component $b_3$)]. In cells in which there is free p27 or free p163, this inhibition leads to inhibition of the expression of the effector gene. In cells in which the p27 protein and/or the p163 protein is/are complexed, so that it can no longer interact with component $b_2$), or is no longer present or is only present to a small extent, this inhibition is lacking, which means that the transcription factor [component b)] can activate the activation sequence [component c)] in an unimpeded manner and thereby begin transcription of the effector gene.

Component $b_24$) constitutes a distinctive feature. The binding of p163/p27 complexes to component $b_24$) in dividing cells inhibits the transcription factor [component b)]; by contrast, the transcription factor [component b)] is free and fully functional in resting cells (i.e. when p27 is present in the free state).

Transcription of the effector gene is initiated by activation of the activation sequence [component a)], which results in the gene for the transcription factor component b) being expressed. The transcription factor [component b)] in turn binds to the activation sequence [component c)], which induces expression of the effector gene [component d)].

In one particular embodiment of this invention, component a) is identical to component c). In this particular embodiment, a slight activation of the activation sequence [promoter I, component a)] leads to expression of the transcription factor [component b)], which activates both the activation sequence [promoter I, component a)] and the activation sequence [promoter II, component c)] and thereby both induces expression of the gene for the effector gene [component d)] and enhances expression of the transcription factor [component b)], thereby in turn enhancing expression of the effector gene [component d)].

This expression system can be extended:
 by stringing together several identical or different sequences for effector genes [components d), d'), d")], which are in each case linked to each other by means of identical or different IRES sequences or by activation sequences [components c') and c")].
 by stringing together several identical or different genes for transcription factors [component b)], which are in each case linked to each other by identical or different IRES sequences or activation sequences [component a) or component c)].

When genes for different transcription factors are strung together, the activation sequences are to be selected such that they contain nucleotide sequences to which the transcription factor [component b)] is able to bind.

Depending on the choice of the activation sequence [component a) or c)], the nucleic acid constructs according to the invention can be used to express an effector gene [component d)] non-specifically, cell-specifically or virus-specifically, or under particular metabolic conditions or else cell cycle-specifically. The effector gene is a gene which, for its part, encodes a pharmacologically active compound or else an enzyme which cleaves an inactive precursor of a drug into an active drug.

For example, the effector gene can be selected such that this active compound or this enzyme is expressed together with a ligand as a fusion protein and this ligand binds to the surface of cells, for example endothelial cells or tumor cells or leucocytes.

The nucleic acid constructs according to the invention which have been cited are preferably composed of DNA. The term "nucleic acid constructs" is understood as meaning artificial nucleic acid structures which can be transcribed in the target cells. They are preferably inserted into a vector, with particular preference being given to plasmid vectors or viral vectors.

The nucleic acid construct, where appropriate inserted into a vector, is administered to a patient for the prophylaxis or therapy of a disease. The administration can be effected perorally, locally or by means of injection or infusion.

Viral and nonviral vectors may be used. For example, viral vectors could be derived from RTV, AV, AAV, or HSV (Jolly, Cancer Gene Ther. 1, 51 (1994)) or could be plasmids complexed with cationic lipids or cationic polymers (Ledley, Human Gene Ther. 6, 1129 (1995)). Such vectors might be loved in physiologic salt solutions containing 1%–30% human albumin (preferable 5%).

$1\times10^5$–$1\times10^{10}$ PFU of viral vectors (preferable $1\times10^8$ PFU) or 0.01 mg –50 mg of plasmids (preferable 1 mg) are suspended in 1 ml of such a medium and applied to the patient. Application may be done by injection (i.v., i.a., s.c., i.m.) into a cavity (pleura, peritoneum, subarachnoidal, into a joint) or into an organ or by local application (intrabronchial, intranasal, dermal, onto conjunctiva, intravaginal, into the bladder).

The present invention also relates to mammalian cells which harbor a nucleic acid construct according to the invention. In a particularly preferred embodiment, the nucleic acid constructs are introduced into cell lines which can then be used, after transfection, as carriers of the expression system according to the invention for expressing the effector gene. Such cells can be used for providing a drug for patients. Alternatively, the cells or cell lines, such as tumor cells, immune cells or endothelial cells, into which the nucleic acid constructs according to the invention have been introduced, can be administered to patients locally or injected into patients parenterally, for example intravenously, intraarterially, into a body cavity, into an organ, or subcutaneously.

Examples of suitable cell or cell lines and their administration are tumor cells transduced in vitro and injected intradermally or subcutaneously for immunization of patients or CD4-positive T-cells transduced to express a new receptor for redirection of its cytotoxicity or muscle cells transduced in vitro to express F IX and reinjected for treatment of defective F IX production A preferred use of the nucleic acid construct according to the invention consequently consists in the prophylaxis or treatment of a disease, with the invention comprising the in-vitro introduction of a nucleic acid construct into a target cell, the non-specific, virus-specific or target cell-specific, metabolically specific and/or cell cycle-specific expression of the drug in the target cell, and the local or parenteral administration of the target cell to the patient, or else the local or parenteral administration of the nucleic acid construct to the patient for in-vivo introduction of a nucleic acid construct into the target cell.

The nucleic acid constructs according to the invention do not occur in this form in nature, i.e. the effector gene for the active compound or for an enzyme or for a ligand-active compound or ligand-enzyme fusion protein is not naturally combined with nucleic acid sequences as are contained in the nucleic acid construct according to the invention.

Preferred effector genes [component d)], which are incorporated into an expression system according to the invention, encode a pharmacologically active compound. Such pharmacologically active compounds are proteins and glycoproteins which are selected from the group consisting of cytokines, growth factors, receptors for cytokines or growth factors, antibodies or antibody fragments, proteins which have an antiproliferative or cytostatic effect, proteins which have an apoptotic or antiapoptotic effect, tumour antigens, angiogenesis inhibitors, thrombosis-inducing proteins, coagulation inhibitors, proteins which have a fibrinolytic effect, blood plasma proteins, complement-activating proteins, envelope substances of viruses and bacteria, hormones, peptides which act on the circulation, neuropeptides, enzymes, mediators, naturally occurring, unaltered regulatory proteins and ribozymes, or (antisense) nucleotide sequences which have an inhibitory effect on gene expression.

Preferably, the transgene is an effector gene which encodes a ribozyme which inactivates the mRNA which encodes a protein which is selected from the group consisting of cell cycle control proteins, in particular cyclin A, cyclin B, cyclin D1, cyclin E, E2F1-5, cdc2, cdc25C, p163 or DP1, or virus proteins or cytokines or growth factors or their receptors.

In another embodiment, the effector gene can encode a ligand-active compound fusion protein, with it being possible for the ligand to be an antibody, an antibody fragment, a cytokine, a growth factor, an adhesion molecule or a peptide hormone, and the active compound to be a pharmacologically active compound as described above or an enzyme. For example, the effector gene can encode a ligand-enzyme fusion protein, with the enzyme cleaving a precursor of a drug into a drug and the ligand binding to a cell surface, preferably to endothelial cells or tumor cells.

B. Detailed Description of the Features of the Invention

1. Characterization of the p163 Protein and the Nucleic Acid Sequence Which Encodes the p163 Protein The "two-hybrid technology" (Fields and Song, Nature 340, 245 (1989)) was used to discover the p163 protein as a new partner protein of p27. For this, PCR was used to clone the entire coding sequence for the murine p27 protein into the yeast vector pGBT10 (Clontech) in-frame with the DNA-binding domain of the transcription factor GAL4. The yeast strain Hf7c (from Clontech Heidelberg, Matchmaker Two Hybrid, K 1605-1) was transformed with this vector, after which tryptophan-auxotrophic colonies were isolated and expression of the correct fusion proteins was detected in Western blots using specific antibodies against GAL4 and p27.

This strain was transformed, in a second transformation, with a VP16-tagged cDNA library from mouse embryos (Vojtek et al., Cell 74, 205 (1993)). 400 colonies, which were histidine-auxotrophic in the presence of 15 nM aminotriazole, were subjected to further analysis. 70 of these clones were sequenced; they all encoded different D-type cyclins; these are known to be interaction partners of p27. Southern blotting was used to show that 390 of the 400 resistant clones encoded D cyclins. Two of the remaining clones ("Number 163") encoded the same protein: they were completely sequenced.

Several clones from a λZAP cDNA library, which was prepared from Balb/c-3T3 cells, were identified as being homologous with p163. Sequence analysis indicates an open reading frame; this is also used in the VP16 chimera from the cDNA library. Both the original clones encode amino acids 121 to 252 of this reading frame. The clone p163 was characterized in more detail in yeast using β-galactosidase as the reporter gene:

As shown in FIG. 1, the encoded protein interacts in yeast specifically with p27, and not with other proteins such as Myc, Max, Bcl-6 or prothymosin-α. FIG. 1 also shows a first delimitation of the domains of p27 in which the interaction with p163 takes place. These data indicate that p163 binds to the same domains in p27 as do cyclin-dependent kinases (Russo et al., Nature 382, 325 (1996)). This is an indication that p163 and cyclin-dependent kinases compete for binding to p27. In the second place, it was possible to delimit the p163 domain which interacts with p27 to amino acids 121 to 252.

In order to confirm these results from this yeast test system, recombinantly expressed 163 [expressed together with glutathione transferase (GST) as a fusion protein] was bound to a column and an attempt was then made to purify $^{35}$S-labeled p27 protein by means of affinity chromatography on this column. The use of the fusion protein comprising p163 together with a glutathione transferase (GST) made it possible to employ a uniform matrix for these experiments (so-called GST pulldowns; Hateboer et al., Proc. Natl. Acad. Sci. USA 90, 8489 (1993)).

For these investigations, the reading frame from the yeast clone was transferred into a pGEX vector (Pharmacia, Freiburg pGEX-2T; Cat. No. 27-4801-01) which encodes a chimeric protein with glutathione-S-transferase (GST) under the control of the IPTG-inducible TAC promoter in E. coli (Smith and Johnson, Gene 67: 31, 1988). Chimeric proteins were purified from induced E. coli cultures by means of affinity chromatography on glutathione-agarose (Smith and Johnson, 1988) and then dialyzed against 100 mM Tris-HCl, pH 7.5, 100 mM KCl, 20 mM EDTA, 10% glycerol, 0.1 mM PMSF. As a control, glutathione-S-transferase was purified in accordance with the same protocol and then dialyzed; the purified proteins were stored at −80° C.

10 μg of the two proteins were then in each case incubated with 10 μg of BSA and 20 mg of swollen GST-agarose at 4° C. for two hours; after that, the agarose was centrifuged off and washed twice with dialysis buffer. An aliquot of the agarose was boiled directly in sample buffer as a control for the binding of the proteins, and the bound proteins were detected after SDS gel electrophoresis. $^{35}$S-Methionine-labeled p27 was prepared by in-vitro translation (in accordance with the instructions of the manufacturer: Promega, Mannheim; TNT coupled retc. lys. systems; L 4610) and incubated with loaded agarose, at 4° C. for two hours, in a total volume of 200 μl in dialysis buffer containing 0.1% NP-40. The agarose was washed four times with dialysis buffer/0.1% NP-40 and then boiled in SDS sample buffer. Bound proteins were detected by means of SDS gel electrophoresis and fluorography.

The results of these experiments are given in FIG. 2. They show that recombinant, in-vitro synthesized $^{35}$S-labeled p27 binds selectively to a column which is loaded with a chimeric GST-p163 fusion protein but not to a column which is loaded with the same quantity of GST. FIG. 2 also shows that p27 from a cell extract binds inefficiently to GST-p163; in this extract, p27 is bound to complexes of cyclin-dependent kinases. A brief heat treatment liberates p27 from these complexes and then allows it to bind to p163. This shows that p163 and cyclin-dependent kinases compete for binding to p27.

The nucleic sequence according to the invention, which encodes the murine p163 protein, is depicted in FIG. 3. This sequence has a homologue in the database; this is the yeast nucleoprotein (Nup)2 gene. Nup2 is a protein of the nuclear membrane which is involved in the formation of nuclear protein and in the transport of proteins in and out of the nucleus. In yeast, Nup2 is probably especially involved in export.

Several functional domains are conserved, although, taken as a whole, the homology is not high (FIG. 4). For example, the site for binding a regulatory protein (Ran, a GTP-binding protein) which regulates nuclear transport is conserved between Ran-binding protein (RBP-1), NuP-2 and p163 (FIG. 5), as are also short pentapeptide sequences to which structural function is ascribed (FIG. 6).

In order to demonstrate beyond doubt that p163 is a nucleoporin, a polyclonal antiserum was generated against the protein [histidine-p163 (aa 121-252)] and then affinity-purified; this antiserum without question recognizes a nucleoporin, as can be seen from the typical nuclear pore staining (dots on surface and the periphery of the nucleus is stained) under immunofluorescence.

In order to demonstrate that p163 or Nup2 and p27 associate intracellularly, the two proteins were expressed transiently in HeLa cells using CMV expression vectors; 48 hours later, the cells were lysed and examined by means of immunoprecipitation/Western blotting for a possible interaction of the two proteins (Peukert et al., EMBO J. 16, 5672 (1997)). The association between p27 and Nup2 was demonstrated in each case a polyclonal antibody against Nup2 and a polyclonal antibody against murine p27. The p27 protein was only precipitated satisfactorily when p163 was expressed (see FIG. 7). This is proof that Nup2 and p27 are able to associate with each other in HeLa cells in vivo.

The nucleic acid sequence for the human p163 protein was identified by carrying out sequence comparisons and data searches using human ESTs. In the case of the Ran-binding domain, they are located in positions 173>575 in the sequence AA161285, in the case of the p27-binding domain, they are located in positions 318>486 in the sequence R62312, and in the case of other constituent segments of p163, they are located in positions 348>489 in the sequence THC199124.

In order to define more precisely the p27 amino acids with which Nup2-p163 interact, a search was carried out in yeast for mutants which no longer interact with p163. For this, the cDNA which encoded p27 was subjected to an error-inducing PCR reaction (PCR conditions as described in "PCR-technology, Principles and Applications for DNA amplifications"; H. A. Erlich, Stockton press, NY 1989), and the resulting clones, which contain random errors, were tested for interaction with Nup2 and, as a control, with cyclin D1. The conditions (which differed from the standard conditions) of this PCR were: 40 cycles in the presence of 1U of GIBCO Taq polymerase and 0.1 mM $MnCl_2$.

The resulting cDNA fragment was cotransformed, together with a pGBT10 vector, which had been linearized with BamHI and EcoRI and then purified, into the yeast strain HF7c-p163/Nup2. Transformed colonies were selected by selection from -Leu-Trp deficient medium. 960 individual clones were isolated and plated out on selective medium (-Leu-His-Trp). A β-galactoside test, as a second interaction test, was carried out on clones which did not grow on this selective medium. Negative clones were identified, and the pGBT10-p27 plasmid was isolated from them. The plasmids which were obtained were firstly retransformed together with a yeast expression plasmid which expresses p163/Nup2 as a chimera containing a transactivating domain and, secondly, as a control, together with a plasmid which expresses cyclin D1 as a chimera containing a transactivating domain. This resulted in three clones which no longer interact selectively with Nup2 but do so with cyclin D1. These plasmids were sequenced together with a few controls.

A range of the resulting phenotypes is summarized in FIG. 13. In these experiments, an interaction manifests itself as growth in the absence of histidine (-Trp-Leu-His, "selective"), whereas the control (-Trp-Leu; "non-selective") shows that both proteins were expressed in yeast. 3 clones out of 1000 were found which no longer interact specifically with p163-Nup2 but do so with cyclin D1. The sequences are shown in FIG. 14. All three clones, but not a series of control clones, carry the same mutation in the amino acid arginine 90 (mutated to glycine). The sequences also show that the clones were formed independently since they carry additional, different mutations. This clearly identifies arginine 90 as being the central amino acid in the interaction of p27 with Nup2. The mutants are available for validating the biological relevance of this interaction.

2. Nucleotide Sequences for Dominant Negative Analogs of the p163 Protein

The above-described functional analyses reveal two domains of the p163 protein which are crucial for its function. One of these domains is the domain (amino acids 121–252) for binding to p27. The other is the domain (amino acids 307–467) for binding to Ran, which is a GTP-binding protein which regulates transport functions.

The invention consequently relates to nucleic acid sequences for protein p163, or for parts or fragments of this protein, with these nucleic acid sequences exhibiting mutations in the p27-binding domain and/or the Ran-binding domain, such that the binding of the expressed mutated protein either to p27 or to Ran is drastically reduced. When introduced into a cell, these analogs of p163 inhibit the functional cell-specific p163. This gives rise to free p27, leading to inhibition of cell division. Examples of such dominant negative mutants of p163 are depicted in FIGS. 8 and 9. FIG. 8 shows p163 in which the p27-binding domain is deleted, while FIG. 9 shows p163 which lacks the Ran-binding domain.

The invention consequently relates to the introduction of nucleic acid constructs encoding dominant negative p163 analogs into a cell with the aim of inhibiting the proliferation of this cell. This introduction into the cell can take place either in vitro or in vivo.

In order to ensure that the expression of the nucleic acid construct according to the invention is the best possible, and/or is subject to control, this construct is preferably linked to an activation sequence. Examples of such activation sequences are listed in Section 8.3. In order to ensure that the nucleic acid sequence encoding p163 becomes located in the nucleus, a nuclear localization signal (NLS) has to be added to it. Such NLSs are known to the skilled person.

The nucleic acid construct is introduced into the cell as naked DNA or with the aid of a non-viral vector or with the aid of, and inserted into, a viral vector, using methods which are known to the skilled person.

3. Nucleotide Sequences for Proteins or Peptides Which Bind to the p163 Binding Domain The investigations which have been presented enabled the p27-binding domain of the p163 protein to be established as being amino acids 121–252 and the Ran-binding domain to be established as being amino acids 307–467.

The invention consequently relates to nucleic acid constructs which encode peptides which either bind to the p163 domain for binding p27, and thereby inhibit the binding of p163 to p27, or to the p163 domain for binding Ran, and thereby inhibit the binding of p163 to Ran. This inhibition results in the formation of free p27, which inhibits the cell proliferation by binding, for example, to cyclin E/cdk2. Examples of such inhibitory peptides are amino acid sequences which correspond to the p163-binding domain of the p27 protein (amino acids 69–178) or of Ran.

Antibodies or antibody fragments, such as $F(ab)_2$, Fab, Fv or s.c. Fv, which bind to p163, in particular to the p27-binding domain or to the Ran-binding site of p163, constitute another example. Such antibodies can be produced, for example, by immunizing animals with p163 or the p27- binding domain or the Ran-binding domain of p163. These domains are depicted in FIG. 5 (Ran-binding domain) and in FIG. 10 (p27-binding domain).

The invention consequently relates to the introduction, into a cell, of nucleic acid constructs which encode proteins which bind to p163, with the aim of inhibiting the proliferation of this cell. This introduction into the cell can take place either in vitro or in vivo.

In order to ensure that the expression of the nucleic acid construct according to the invention is the best possible and/or subject to control, this construct is preferably linked to an activation sequence. Examples of such activation sequences are listed in Section 8.3. In order to ensure that the nucleic acid sequence encoding the nucleic acid construct according to the invention becomes located in the nucleus, a nuclear localization signal (NLS) has to be added to it. Such NLSs are known to the skilled person.

The nucleic acid construct is introduced into the cell as naked DNA or with the aid of a non-viral vector or with the aid of, and inserted into, a viral vector, using methods which are known to the skilled person.

4. Nucleotide Sequences for p163 for Stimulating Cell Division

The introduction of the nucleotide sequence for p163, or of the p163 protein, into a cell leads to inhibition of the intracellular p27. This liberates cyclin E/cdk2 complexes (which are inhibited by p27), which complexes initiate cell division.

The invention consequently relates to the introduction of p163-encoding nucleic acid constructs into a cell with the aim of promoting the proliferation of the cell. This introduction into the cell can take place either in vitro or in vivo.

In order to ensure that the expression of the nucleic acid construct according to the invention is the best possible and/or is subject to control, this construct is preferably linked to an activation sequence. Examples of such activation sequences are listed in Section 8.3. In order to ensure that the nucleic acid sequence encoding p163 becomes located in the nucleus, a nuclear localization signal (NLS) has to be added to it. Such NLSs are known to the skilled person.

The nucleic acid construct is introduced into the cell as naked DNA or with the aid of a non-viral vector or with the aid of, and inserted into, a viral vector, using methods which are known to the skilled person.

The introduction of a p163-encoding nucleic acid construct can, for example, stimulate cells in cell culture or cells in vivo to proliferate when, for example, cell proliferation is deficient.

5. Nucleotide Sequences for Inhibiting Transcription and/or Translation of the p163 Protein Knowledge of the nucleic acid sequence of the p163 protein offers the possibility of preparing oligonucleotides which can be used for specifically inhibiting the transcription or translation of p163. These antisense nucleic acids include oligonucleotides, antisense (triplex) DNA, ribozymes and antisense RNA. The method for preparing triplex DNA oligonucleotides has been described in detail by Frank-Kamenetskii and Mirkin, Ann. Rev. Biochem. 64, 65 (1995) and the method for preparing antisense RNA oligonucleotides has been described in detail by Neckers et al., Crit. Rev. Oncogen. 3, 175 (1992); Carter and Lemoine, Br. J. Cancer 67, 869 (1993); Mukhdopadhyay and Roth, Crit. Rev. Oncogen. 7, 151 (1996) and Mercola and Cohen, Cancer Gene Ther. 2, 47 (1995).

Preference is given, within the meaning of the invention, to using triplex DNA or antisense RNA oligonucleotides which hybridize with p163 nucleotide sequences which encode constituent regions of the domain (total region, amino acids 121–252) for binding the p27 protein or constituent regions of the domain (total region, amino acids 307–467) for binding the Ran protein.

The nucleotide sequences which inhibit the transcription and/or translation of p163 furthermore include ribozymes which are specific for nucleotide sequence regions of the p163 protein.

The method for preparing ribozymes has been described in detail by Burke, Nucl. Acids Mol. Biol. 8, 105 (1994), Christoffersen and Marr, J. Med. Chem. 38, 2023 (1995) and Scott et al., Science 274, 2065 (1996). Within the meaning of the invention, preference is given to ribozymes which hybridize with p163 nucleotide sequences which are located in the region of the nucleotide sequence for the domain (amino acids 121–252) for binding the p27 protein or for the domain (amino acids 307–467) for binding the Ran protein.

Examples of nucleotide sequences of the p163 protein which can be cleaved by ribozymes are listed in FIG. 11.

Triplex DNA, antisense RNA or ribozymes are either added to the target cells in vitro, or administered in vivo by injection or local application, as oligonucleotides [prepared, and protected against degradation by DNases or RNases, using methods which are known to the skilled person (see the above-cited literature)].

However, the invention also relates to the introduction of nucleic acid constructs into a cell with the aim of forming in the cell, by transcription, the antisense RNA or ribozymes corresponding to the oligonucleotides according to the invention in order to inhibit the proliferation of this cell. The introduction into the cell can either be effected in vitro or in vivo.

In order to ensure that the expression of the nucleic acid construct according to the invention is the best possible and/or is subject to control, this construct is preferably linked to an activation sequence. Examples of such activation sequences are listed in Section 8.3.

The nucleic acid construct is introduced into the cell as naked DNA or with the aid of a non-viral vector or with the aid of, and inserted into, a viral vector using the methods known to the skilled person.

6. Test Systems for Finding Inhibitors of p163 Function

The discovery of the p163 protein and its interaction with the p27 protein makes it possible to search for inhibitors of this interaction. This requires test systems in which the binding between the p27 protein and the p163 protein is inhibited and the occurrence of this inhibition is shown by an indicator.

A large number of methods are known. One example of this method is the two-hybrid screen assay (in this regard, see Section C.1. and FIG. 1).

Alternatively, however, an affinity system can also, for example, be used for the screening, in which system p163 [preferably the p27-binding domain (amino acid 121–252)] is bound to a solid phase and incubated with the test substance, and the binding of the test substance is ascertained by inhibition of the binding of a labeled binding partner for the p27-binding domain of the p163 protein. This labeled binding partner can be p27 or an antibody which binds specifically to the p27-binding domain of the p163 protein.

Test systems for inhibitors of the binding between p163 and Ran can be constructed, and used for the screening, in the same way as for inhibitors of the binding between p163 and p27. The invention consequently relates to the use of nucleic acid sequences which encode p163, or constituent proteins of p163, or to the use of the p163 protein, or constituent proteins thereof, for searching for inhibitors of p163.

7. Use of the Nucleic Acid Sequence for p163 or of the Protein Sequence p163 for Diagnosing the Stage of Proliferation of a Cell or a Disease State As explained in the introduction Section A), a number of tumors are characterized by an increased intracellular concentration of p27. Because these tumors proliferate, it is to be assumed that the function of this increased p27 is inhibited. According to this invention, p163 is the specific inhibitor of p27. The detection of this inhibitor in a cell makes it possible to draw a conclusion about the proliferation state of the cell. This conclusion can, for example, be of great importance for assessing the malignancy of a tumor cell or of a tumor tissue. The p163 protein is released by cell death. The detection of p163 in a body fluid consequently enables conclusions to be drawn with regard to proliferative processes and/or processes which are accompanied by cell death, for example inflammatory processes, in a body. The p163 protein can be detected by specific binding to labeled substances. These specifically binding substances include the p27 protein, the Ran protein and antibodies, for example produced by immunizing animals with the p163 protein or with constituent sequences of this protein.

However, p163 mRNA may also be detected in a cell or a tissue by hybridizing the protein p163-encoding nucleic acid sequence with the corresponding mRNA. It is possible to use the polymerase chain reaction (PCR) technology, with which the skilled person is familiar and in which a few copies of a nucleic acid sequence to be detected can be multiplied using so-called primer pairs, to increase the sensitivity of this detection.

Examples of primer pairs for amplifying and detecting the p163-encoding nucleic acid sequence are depicted in FIGS. 12a, b and c.

However, it is also possible to detect the p163-encoding RNA by, for example, using fluorescence in situ hybridization as published by Gussoni et al., Nature Biotechnol. 14, 1012 (1996).

The invention consequently relates to the detection of a p163-encoding nucleic acid sequence or of the p163 protein for ascertaining the proliferation state of a cell or a tissue or for detecting proliferative changes, or changes which are accompanied by cell death, in a living mammal.

8. Distinctive Features of the Expression Systems Which are Controlled by p163, p27 or the p163/p27 Complex 8.1. Component b)

8.1.1. Binding Sequence for p163, p27 or the p163/p27 Protein Complex [Component $b_2$)]

In a preferred embodiment of the invention, the expression system contains, as its component $b_2$), at least one nucleic acid sequence for the p163 protein or for that part of the p163 protein which binds to the p27 protein.

In another preferred embodiment, the expression system contains, as its component $b_2$), at least one nucleic acid sequence for an antibody or a part of an antibody containing the binding sequences ($V_H$ and $V_L$)

for the site in the p27 protein which binds the p163 protein, or for the site in the p163 protein which binds the p27 protein.

In these embodiments, free p27 protein or free p163 protein which is present in the cell, for example, binds to the expression product of component $b_2$) and thereby inhibits the transcription factor encoded by component b) and consequently blocks the expression system. If, however, the p27 protein is complexed, for example, with the p163 protein in a cell, the expression product of component $b_2$), and consequently the transcription factor [component b)] remain free and the expression system is capable of functioning.

These expression systems according to the invention are consequently able to function in dividing cells (presence of p163/p27 complexes) and are inhibited in resting cells (free p27).

In another particular embodiment, the expression system contains, as its component $b_2$), at least one nucleic acid sequence for an antibody or a part of an antibody containing the binding sequences ($V_H$ and $V_L$) for the complex composed of p27 and p163. In this embodiment, complexes of p27 and p163 bind to the expression product of component $b_2$) and thereby block the expression system, whereas free p27 or p163 does not bind to the expression product of component $b_2$).

This expression system according to the invention is consequently blocked in dividing cells (presence of p163/p27 complexes) and able to function in resting cells (free p27).

When choosing an antibody for component $b_2$), preference is given to employing the epitope-binding parts of the antibody, i.e. $FV_L$ and $FV_H$, which are in humanized form if the antibody is of murine origin. The humanization is effected in the manner described by Winter et al. (Nature 349, 293 (1991) and Hoogenbooms et al. (Rev. Tr. Transfus. Hemobiol. 36, 19 (1993)). The antibody fragments are prepared in accordance with the state of the art, for example in the manner described by Winter et al., Nature 349, 293 (1991), Hoogenboom et al., Rev. Tr. Transfus. Hemobiol. 36, 19 (1993), Girol. Mol. Immunol. 28, 1379 (1991) or Huston et al., Int. Rev. Immunol. 10, 195 (1993). The preparation of antibodies, antibody fragments and recombinant antibody fragments was described in detail in Patent Application DE 96 49 645.4.

Recombinant antibody fragments are either prepared directly from existing hybridomas or are isolated from libraries of murine or human antibody fragments with the aid of phage-display technology (Winter et al., Annu. Rev. Immunol. 12, 433 (1994)). These antibody fragments are then employed directly at the genetic level for the coupling to components $b_1$) and $b_3$).

In order to prepare recombinant antibody fragments from hybridomas, the genetic information which encodes the antigen-binding domains ($V_H$, $V_L$) of the antibodies is obtained by isolating the mRNA, reverse-transcribing the RNA into cDNA and then amplifying by means of the polymerase chain reaction and using oligonucleotides which are complementary to the 5' and 3' ends, respectively, of the variable fragments. The resulting DNA fragments, which encode the $V_H$ and $V_L$ fragments, are then cloned into bacterial expression vectors; Fv fragments, single-chain Fv fragments (scFv) or Fab fragments can, for example, be expressed in this way.

New antibody fragments can also be isolated directly from antibody libraries (immune libraries or naive libraries) of murine or human origin using the phage-display technology. In the phage display of antibody fragments, the antigen-binding domains are cloned, in the form of scFV fragment genes or as Fab fragment genes, as fusion proteins with the gene for the g3P coat protein of filamentous bacteriophages, either into the phage genome or into phagemid vectors. Antigen-binding phages are selected on antigen-loaded plastic receptacles (panning), on antigen-conjugated paramagnetic beads or by binding to cell surfaces.

Immune libraries are prepared by PCR amplification of the genes for the variable antibody fragments from B lymphocytes of immunized animals or patients. Combinations of oligonucleotides which are specific for murine or human immunoglobulins or for the human immunoglobulin gene families are used for this purpose.

Naive libraries can be prepared by using nonimmunized donors as the source of the immunoglobulin genes. Alternatively, immunoglobulin germ line genes can be employed for preparing semisynthetic antibody repertoires, with the complementarity-determining region 3 of the variable fragments being amplified by PCR using degenerate primers. These so-called single-pot libraries enjoy the advantage, as compared with immune libraries, that antibody fragments against a large number of antigens can be isolated from one single library.

The affinity of antibody fragments can be further increased by means of the phage-display technology, with new libraries being prepared from already existing antibody fragments by means of random, codon-based or site-directed mutagenesis, by shuffling the chains of individual domains with fragments from naive repertoires or by using bacterial mutator strains, and antibody fragments possessing improved properties being isolated by means of reselection under stringent conditions. In addition, murine antibody fragments can be humanized by step wise replacement of one of the variable domains with a human repertoire and subsequent selection using the original antigen (guided selection). Alternatively, humanization of murine antibodies is effected by the purposeful replacement of the hypervariable regions of human antibodies with the corresponding regions of the original murine antibody.

8.1.2. The Activation Domain [Component $b_1$)] and the DNA-binding Domain [Component $b_3$)]

Within the meaning of the invention, all available genes for activation domains and DNA-binding domains of a transcription factor can be used for component b). Examples of these domains, whose description is not, however, intended to limit the invention, are:

Activation domains [component $b_1$)] at least one sequence
of the cDNA for the acid transactivation domain (TAD)
of HSV1-VP16 (amino acids 406 to 488; Triezenberg et al., Genes Developm. 2: 718 (1988); Triezenberg, Curr. Opin. Gen. Developm. 5: 190 (1995) or amino acids 413 to 490; Regier et al., Proc. Natl. Acad. Sci. USA 90, 883 (1993)) or
of the activation domain of Oct-2 (amino acids 438 to 479; Tanaka et al., Mol. Cell. Biol. 14: 6046 (1994) or amino acids 3 to 154; Das et al., Nature 374: 657 (1995)) or
of the activation domain of SP1 (amino acids 340 to 485; Courey and Tijan, Cell 55, 887 (1988)) or
of the activation domain of NFY (amino acids 1 to 233; Li et al., J. Biol. Chem. 267, 8984 (1992); van Hujisduijnen et al., EMBO J. 9, 3119 (1990); Sinha et al., J. Biol. Chem. 92, 1624 (1995); Coustry et al. J. Biol. Chem. 270, 468 (1995)) or
of the activation domain of ITF2 (amino acids 2 to 452; Seipel et al., EMBO J. 13, 4961 (1992)) or
of the activation domain of c-Myc (amino acids 1 to 262; Eilers et al.) or
of the activation domain of CTF (amino acids 399 to 499; Mermod et al., Cell 58, 741 (1989); Das and Herr, Nature 374, 657 (1995))

DNA-binding domains [component $b_3$)] at least one sequence
of the cDNA for the DNA-binding domain of the Gal4 protein (amino acids 1 to 147; Chasman and Kornberg, Mol. Cell. Biol. 10: 2916 (1990)) or of the LexA protein (amino acids 1 to 81; Kim et al., Science 255: 203 (1992) or the entire LexA protein (amino acids 1 to 202; Brent et al., Cell 43: 729 (1985)) or
of the lac repressor (lac I) protein (Brown et al., Cell 49: 603 (1987); Fuerst et al., PNAS USA 86: 2549 (1989)) or
of the tetracycline repressor (tet R) protein (Gossen et al., PNAS USA 89; 5547 (1992); Dingermann et al., EMBO J. 11: 1487 (1992)) or
of the ZFHD1 protein (Pomerantz et al., Science 267: 93 (1995)).

Within the meaning of the invention, a nuclear localization signal (NLS) is advantageously to be added to the 3' end of the DNA-binding domain.

8.2. The Promoter Unit II [Component c)] Activation Sequence Which can be Activated by Component b)

The choice of this activation sequence depends on the choice of the DNA-binding domain [component $b_3$)] in the gene for a transcription factor [component b)]. The following possibilities in turn exist, by way of example, for the examples of the DNA-binding domains listed under 8.1.2:

8.2.1. Possibility A)
an activation sequence
containing at least one sequence [nucleotide sequence: 5'-CGGACAACTGTTGACCG-3', SEQ ID NO.: 1] for binding the Gal4 protein (Chasman and Kornberg, Mol. Cell Biol. 10, 2916 (1990)) and (to whose 3' end) is added
the basal promoter of SV40 (nucleic acids 48 to 5191; Tooze (ed), DNA Tumor Viruses (Cold Spring Harbor New York, N.Y.; Cold Spring Harbor Laboratory) or
the promoter of c-fos (Das et al., Nature 374, 657 (1995)) or
the U2 sn RNA promoter or
the promoter of HSV TK (Papavassiliou et al., J. Biol. Chem. 265, 9402 (1990); Park et al., Molec. Endocrinol. 7, 319 (1993)).

8.2.2. Possibility B)
an activation sequence
containing at least one sequence [nucleotide sequence 5'-TACTGTATGTACATACAGTA-3', SEQ ID NO.: 2] for binding the LexA protein [LexA operator; Brent et al., Nature 612, 312 (1984)] and (to whose 3' end) is added
the basal promoter of SV40 (nucleic acids 48 to 5191; Tooze (ed), DNA Tumor Viruses (Cold Spring Harbor New York, N.Y.; Cold Spring Harbor Laboratory) or another promoter (see possibility A)

8.2.3. Possibility C)
an activation sequence
containing at least one Lac operator sequence (nucleotide sequence: 5'-GAATTGTGAGCGCTCACAATTC-3', SEQ ID NO.: 3) for binding the lac I repressor protein (Fuerst et al., PNAS USA 86, 2549 (1989); Simons et al., PNAS USA 81, 1624 (1984)) and (to whose 3' end) the basal promoter of SV40 (nucleic acids 48 to 5191; Tooze (ed) DNA Tumor Viruses (Cold Spring Harbor New York, N.Y., Cold Spring Harbor Laboratory) or another promoter (see possibility A)

8.2.4. Possibility D)
an activation sequence
containing at least one tetracycline operator (tet O) sequence (nucleotide sequence: 5'-TCGAGTTTACCACTCCCTATCAGT- GATAGAGAAAAGTGAAAG-3', SEQ ID NO.: 4) for binding the tetracycline repressor (tet R) protein and (to whose 3' end) is added the basal promoter of SV40 (nucleic acids 48 to 5191; Tooze (ed.) DNA Tumor Viruses (Cold Spring Harbor New York, N.Y., Cold Spring Harbor Laboratory) or another promoter (see possibility A).

8.2.5. Possibility E)

an activation sequence containing at least one sequence [nucleotide sequence 5'-TAATGATGGGCG-3', SEQ ID NO.: 5] for binding the ZFHD-1 protein (Pomerantz et al., Science 267, 93 (1995)) and (to whose 3' end) is added the basal promoter of SV40 (nucleic acids 48 to 5191; Tooze (ed.), DNA Tumor Viruses (Cold Spring Harbor New York, N.Y., Cold Spring Harbor Laboratory) or another promoter (see possibility A).

8.3. The activation sequence I [component a)]

Within the meaning of the invention, nucleotide sequences which, after binding transcription factors, activate the transcription of a gene which is located adjacently at the 3' end are to be used as activation sequences. The choice of the activation sequence depends on the disease to be treated and on the target cell to be transduced. Thus, the activation sequence [component a)] may be activatable in an unrestricted manner, target cell-specifically, under particular metabolic conditions, cell cycle-specifically or virus-specifically. These promoter sequences have already hi been described in detail in Patent Applications EP95930524.4, EP95931933.6, EP95931204.2, EP95931205.9, EP97101507.8, EP97102547.3, DE196.39103.2 and DE196.51443.6. Examples of the promoter sequences to be selected are:

8.3.1. Activator Sequences and Promoters Which can be Activated in an Unrestricted Manner, Such as the promoter of RNA polymerase III the promoter of RNA polymerase II the CMV promoter and enhancer the SV40 promoter 8.3.2. Viral Promoter and Activator Sequences, Such as

HBV

HCV

HSV

HPV

EBV

HTLV

HIV

When the HIV promoter is used, the entire LTR sequence, including the TAR sequence [position −453 to −80, Rosen et al., Cell 41, 813 (1985)] is to be employed as a virus-specific promoter.

8.3.3. Metabolically Activatable Promoter and Enhancer Sequences, Such as the Hypoxia-inducible Enhancer.

8.3.4. Promoters Which can be Activated Cell Cycle-specifically

Examples of these promoters are the promoter of the cdc25C gene, of the cyclin A gene, of the cdc2 gene, of the B-myb gene, of the DHFR gene, of the E2F-1 gene or of the cdc25B gene, or else sequences for binding transcription factors which appear or are activated during cell proliferation. These binding sequences include, for example, sequences for binding c-myc proteins. These binding sequences also include monomers or multimers of the nucleotide sequence [5'-GGAAGCAGACCACGTGGTCTGCTTCC-3', SEQ ID NO.: 6; Blackwood and Eisenmann, Science 251: 1211 (1991)] which is designated the Myc E box.

8.3.5. Promoters Which can be Activated by Tetracycline, Such as the Tetracycline Operator in Combination With a Corresponding Repressor.

8.3.6. Chimeric Promoters

A chimeric promoter is the combination of an upstream activator sequence which can be activated cell-specifically, metabolically or virus-specifically with a downstream promoter module which contains the nucleotide sequence CDE-CHR or E2FBS-CHR, to which suppressor proteins bind and are thereby able to inhibit the activation of the upstream activator sequence in the Go and G1 phase of the cell cycle (PCT/GB9417366.3; Lucibello et al., EMBO J. 14, 12 (1994)).

8.3.7. Promoters Which can be Activated Cell-specifically

These preferably include promoters or activator sequences composed of promoters or enhancers from those genes which encode proteins which are preferentially formed in selected cells.

For example, within the meaning of the invention, promoters for the following proteins are preferably to be used in the following cells:

8.3.7.1. Promoter and Activator Sequences Which are Activated in Endothelial Cells Brain-specific, endothelial glucose-1-transporter Endoglin VEGF receptor 1 (flt-1)

VEGF receptor 2 (flk-1, KDR)

tie-1 or tie-2

B61 receptor (Eck receptor)

B61

Endothelin, especially endothelin B or endothelin 1

Endothelin receptors, in particular the endothelin B receptor

Mannose 6-phosphate receptors von Willebrand factor

IL-1α and IL-1β

IL-1 receptor vascular cell adhesion molecule (VCAM-1)

synthetic activator sequences.

Synthetic activator sequences, which are composed of oligomerized sites for binding transcription factors which are preferentially or selectively active in endothelial cells can also be used as an alternative to natural endothelial cell-specific promoters. An example is the transcription factor GATA-2, whose binding site in the endothelin 1 gene is 5'-TTATCT-3' [Lee et al., Biol. Chem. 266, 16188 (1991), Dormann et al., J. Biol. Chem. 267, 1279 (1992) and Wilson et al., Mol. Cell Biol. 10, 4854 (1990)].

8.3.7.2. Promoters or Activator Sequences Which are Activated in Cells in the Vicinity of Activated Endothelial Cells

VEGF

The gene-regulatory sequences for the VEGF gene are the 5'-flanking region, the 3'-flanking region, the c-Src gene or the v-Src gene Steroid hormone receptors and their promoter elements (Truss and Beato, Endocr. Rev. 14, 459 (1993)), in particular the mouse mammary tumor virus promoter 8.3.7.3. Promoters or Activator Sequences Which are Activated in Muscle Cells, in Particular Smooth Muscle Cells Tropomyosin α-Actin α-Myosin Receptor for PDGF
Receptor for FGF
MRF-4
Phosphofructokinase A
Phosphoglycerate mutase
Troponin C
Myogenin
Receptors for endothelin A
Desmin
VEGF
  The gene-regulatory sequences for the VEGF gene have already been listed in the "promoters which are activated in cells in the vicinity of activated endothelial cells" section (see above)
"artificial" promoters
Factors of the helix-loop-helix (HLH) family (MyoD, Myf-5, Myogenin, MRF4) are described as muscle-specific transcription factors. The muscle-specific transcription factors also include the zinc finger protein GATA-4.

The HLH proteins and GATA-4 exhibit muscle-specific transcription not only with promoters of muscle-specific genes but also in the heterologous context, that is also with artificial promoters. Examples of artificial promoters of this nature are multiple copies of the (DNA) site for binding muscle-specific HLH proteins, such as the E box (Myo D) (e.g. 4×AGCAGGTGTTGGGAGGC, SEQ ID NO.: 7) or multiple copies of the DNA site for binding GATA-4 of the α-myosin heavy chain gene (e.g. 5'-GGCCGATGGGCAGATAGAGGGGGCCGATGGGCAGATAGAGG3', SEQ ID NO.: 8)

8.3.7.4. Promoters and Activator Sequences Which are Activated in Glia Cells

These include, in particular, the gene-regulatory sequences or elements from genes which encode, for example, the following proteins:
  the Schwann cell-specific protein periaxin
  glutamine synthetase
  the glia cell-specific protein (glial fibrillary acid protein= GFAP)
  the glia cell protein S100b
  IL-6 (CNTF)
  5-HT receptors
  TNFα
  IL-10
  insulin-like growth factor receptors I and II
  VEGF
    The gene-regulatory sequences for the VEGF gene have already been listed above.

8.3.7.5. Promoters and Activator Sequences Which are Activated in Hematopoietic Cells Gene-regulatory sequences of this nature include promoter sequences for genes for a cytokine or its receptor which are expressed in hematopoietic cells or in neighboring cells, such as the stroma.

These include promoter sequences for the following cytokines and their receptors, for example:
  stem cell factor receptor
  stem cell factor
  IL-1α
  IL-1 receptor
  IL-3
  IL-3 receptor (α-subunit)
  IL-3 receptor (β-subunit)
  IL-6
  IL-6 receptor
  GM-CSF
  GM-CSF receptor (α-chain)
  interferon regulatory factor 1 (IRF-1) The promoter of IRF-1 is activated equally well by IL-6 as by IFNγ or IFNβ
  erythropoietin
  erythropoietin receptor.

7.3.7.6. Promoters and Activator Sequences Which are Activated in Lymphocytes and/or Macrophages These include, for example, the promoter and activator sequences of the genes for cytokines, cytokine receptors and adhesion molecules and receptors for the Fc fragment of antibodies.

Examples are:
  IL-1 receptor
  IL-1α
  IL-1β
  IL-2
  IL-2 receptor
  IL-3
  IL-3 receptor (α-subunit)
  IL-3 receptor (β-subunit)
  IL-4
  IL-4 receptor
  IL-5
  IL-6
  IL-6 receptor
  interferon regulatory factor 1 (IRF-1) (The promoter of IRF-1 is activated equally well by IL-6 as by IFNγ or IFNβ).
  IFNγ-responsive promoter
  IL-7
  IL-8
  IL-10
  IL-11
  IFNγ
  GM-CSF
  GM-CSF receptor (α-chain)
  IL-13
  LIF
  Macrophage colony-stimulating factor (M-CSF) receptor
  Type I and II macrophage scavenger receptors
  MAC-1 (leucocyte function antigen)
  LFA-1 (leucocyte function antigen)
  p150,95 (leucocyte function antigen)

8.3.7.7. Promoter and Activator Sequences Which are Activated in Synovial Cells

These include the promoter sequences for matrix metalloproteinases (MMP), for example for:
  MMP-1 (interstitial collagenase)
  MMP-3 (stromelysin/transin)

They furthermore include the promoter sequences for tissue inhibitors of metalloproteinases (TIMP), for example
  TIMP-1
  TIMP-2
  TIMP-3

8.3.7.8. Promoters and Activator Sequences Which are Activated in Leukemia Cells These include, for example, promoters for c-myc

HSP-70 bcl-1/cyclin D-1 bcl-2

IL-6

IL-10

TNFα, TNFβ

HOX-11

BCR-Abl

E2A-PBX-1

PML-RARA (promyelocytic leukemia—retinoic acid receptor)

c-myc c-myc proteins bind to, and activate, multimers of the nucleotide sequence (5'-GGAAGCAGACCACGTGGTCTGCTTCC-3', SEQ ID NO.: 6) which is designated the Myc E box 8.3.7.9. Promoters or Activator Sequences Which are Activated in Tumor Cells A gene-regulatory nucleotide sequence with which transcription factors which are formed or are active in tumor cells interact is envisaged as the promoter or activator sequence.

Within the meaning of this invention, the preferred promoters or activator sequences include gene-regulatory sequences or elements from genes which encode proteins which are formed, in particular, in cancer cells or sarcoma cells. Thus, use is preferably made of the promoter of the N-CAM protein in the case of small-cell bronchial carcinomas, of the promoter of the "hepatitis growth factor" receptor or of L-plastin in the case of ovarian carcinomas, and of the promoter of L-plastin or of polymorphic epithelial mucin (PEM) in the case of pancreatic carcinomas.

8.4. The Effector Gene [Component d)]

Within the meaning of the invention, the effector genes [component d)] encode an active compound for the prophylaxis and/or therapy of a disease. Effector genes and promoter sequences are to be selected with regard to the nature of the therapy of the disease and taking into consideration the target cell to be transduced.

For example, the following combinations of promoter sequences and effector genes are to be selected in the case of the following diseases (a detailed description has already been given in Patent Applications EP95930524.4, EP95931933.6, EP95931204.2, EP95931205.9, EP97101507.8, D196.17851.7, D196.39103.2 and D196.51443.6, which are hereby incorporated by reference).

8.4.1. Therapy of Tumors 1.1. Target Cells:

proliferating endothelial cells or stroma cells and muscle cells which are adjacent to the endothelial cell, or tumor cells or leukemia cells 1.2. Promoters:

endothelial cell-specific and cell cycle-specific, or cell-nonspecific or muscle cell-specific and cell cycle-specific, or tumor cell-specific (solid tumors, leukemias) and cell cycle-specific 1.3. Effector Genes for Inhibitors of Cell Proliferation, for Example for the retinoblastoma protein (pRb=p110) or the related p107 and p130 proteins The retinoblastoma protein (pRb/p110) and the related p107 and p130 proteins are inactivated by phosphorylation. Preference is given to using those genes for these cell cycle inhibitors which exhibit mutations for the inactivation sites of the expressed proteins without the function of the latter thereby being impaired. Examples of these mutations have been described for p110.

The DNA sequence for the p107 protein or the p130 protein is mutated in an analogous manner.

the p53 protein

The p53 protein is inactivated in the cell either by binding to special proteins, such as MDM2, or by means of oligomerization of the p53 by way of the dephosphorylated C-terminal serine. Preference is consequently given to using a DNA sequence for a p53 protein which is truncated C-terminally by the serine 392 p21 (WAF-1)

the p16 protein other cdk inhibitors the GADD45 protein the bak protein a protein for binding a regulatory protein (see II.1.)

1.4. Effector Genes for Coagulation-inducing Factors and Angiogenesis Inhibitors, for Example:

plasminogen activator inhibitor 1 (PAI-1)

PAI-2

PAI-3 angiostatin interferons (IFNα, IFNβ or IFNγ)

platelet factor 4

TIMP-1

TIMP-2

TIMP-3 leukemia inhibitory factor (LIF)

tissue factor (TF) and its coagulation-active fragments 1.5. Effector Genes for Cytostatic and Cytotoxic Proteins, for Example for perforin granzyme

IL-2

IL4

IL-12 interferons, such as IFN-α, IFNβ or IFNγ

TNF, such as TNFα or TNFβ oncostatin M sphingomyelinase magainin and Magainin derivatives 1.6. Effector Genes for Cytostatic or Cytotoxic Antibodies and for Fusion Proteins Formed Between Antigen-binding Antibody Fragments and Cytostatic, Cytotoxic or Inflammatory Proteins or Enzymes The cytostatic or cytotoxic antibodies include those which are directed against membrane structures of endothelial cells, as have been described, for example, by Burrows et al. (Pharmac. Ther. 64, 155 (1994)), Hughes et al., (Cancer Res. 49, 6214 (1989)) and Maruyama et al., (PNAS USA 87, 5744 (1990)). They include, in particular, antibodies against the VEGF receptors.

They furthermore include cytostatic or cytotoxic antibodies which are directed against membrane structures on tumor cells. Antibodies of this nature have been reviewed, for example, by Sedlacek et al., Contrib. to Oncol. 32, Karger Verlag, Munich (1988) and Contrib. to Oncol. 43, Karger Verlag, Munich (1992). Other examples are antibodies against sialyl Lewis; against peptides on tumors which are recognized by T cells; against oncogene-expressed proteins; against gangliosides such as GD3, GD2, GM2, 9-0-acetyl GD3, fucosyl GM1; against blood group antigens and their precursors; against antigens on polymorphic epithelial mucin; against antigens on heat shock proteins.

They furthermore include antibodies which are directed against membrane structures of leukemia cells. A large number of monoclonal antibodies of this nature have already been described for diagnostic and therapeutic methods (reviews in Kristensen, Danish Medical Bulletin 41, 52 (1994); Schranz, Therapia Hungarica 38, 3 (1990); Drexler et al., Leuk. Res. 10, 279 (1986); Naeim, Dis. Markers 7, 1 (1989); Stickney et al., Curr. Opin. Oncol. 4, 847 (1992); Drexler et al., Blut 57, 327 (1988); Freedman et al., Cancer Invest. 9, 69 (1991)). Depending on the type of leukemia, monoclonal antibodies, or their antigen-binding antibody fragments, which are directed against the following membrane antigens are suitable, for example, for use as ligands:

| Cells | Membrane antigen |
|---|---|
| AML | CD13 |
| | CD15 |
| | CD33 |
| | CAMAL |
| | Sialosyl-Le |
| B-CLL | CD5 |
| | CD1c |
| | CD23 |
| | Idiotypes and isotypes of the membrane immunoglobulins |
| T-CLL | CD33 |
| | M38 |
| | IL-2 receptors |
| | T-cell receptors |
| ALL | CALLA |
| | CD19 |
| | Non-Hodgkin's lymphoma |

The humanization of murine antibodies and the preparation and optimization of the genes for Fab and rec. Fv fragments are carried out in accordance with the technique known to the skilled person (Winter et al., Nature 349, 293 (1991); Hoogenbooms et al., Rev. Tr. Transfus. Hemobiol. 36, 19 (1993); Girol. Mol. Immunol. 28, 1379 (1991) or Huston et al., Intern. Rev. Immunol. 10, 195 (1993)). The fusion of the rec. Fv fragments with genes for cytostatic, cytotoxic or inflammatory proteins or enzymes is likewise carried out in accordance with the state of the art known to the skilled person.

1.7. Effector Genes for Fusion Proteins Formed From Target Cell-binding Ligands and Cytostatic and Cytotoxic Proteins The ligands include all substances which bind to membrane structures or membrane receptors on endothelial cells. Examples of these ligands are Cytokines, such as IL-1, or growth factors, or their fragments or constituent sequences thereof, which bind to receptors which are expressed by endothelial cells, such as PDGF, bFGF, VEGF and TGF.

They furthermore include adhesion molecules which bind to activated and/or proliferating endothelial cells. These include, for example, SLex, LFA-1, MAC-1, LECAM-1, VLA-4 or vitronectin.

They furthermore include substances which bind to membrane structures or membrane receptors of tumor or leukemia cells. Examples of these are hormones or growth factors, or their fragments or constituent sequences thereof, which bind to receptors which are expressed by leukemia cells or tumor cells.

Growth factors of this nature have already been described (reviews in Cross et al., Cell 64, 271 (1991), Aulitzky et al., Drugs 48, 667 (1994), Moore, Clin. Cancer Res. 1, 3 (1995), Van Kooten et al., Leuk. Lymph. 12, 27 (1993)).

The fusion of the genes for these ligands which bind to the target cell with cytostatic, cytotoxic or inflammatory proteins or enzymes is effected in accordance with the state of the art using the methods which are known to the skilled person.

1.8. Effector Genes for Inflammation Inducers, for Example for

IL-1

IL-2

RANTES (MCP-2)

monocyte chemotactic and activating factor (MCAF)

IL-8 macrophage inflammatory protein-1 (MIP-1α, -β)

neutrophil activating protein-2 (NAP-2)

IL-3

IL-5 human leukemia inhibitory factor (LIF)

IL-7

IL-11

IL-13

GM-CSF

G-CSF

M-CSF cobra venom factor (CVF) or constituent sequences of CVF which correspond functionally to human complement factor C3b, i.e. which are able to bind to complement factor B and, after cleavage by factor D, constitute a C3 convertase human complement factor C3 or its constituent sequence C3b cleavage products of human complement factor C3 which resemble CVF functionally and structurally bacterial proteins which activate complement or trigger inflammations, such as Salmonella typhimurium porins, Staphylococcus aureus clumping factors, modulins, particularly from Gram-negative bacteria, major outer membrane protein from legionellas or from Haemophilus influenzae type B or from klebsiellas, or M molecules from group G streptococci.

1.9. Effector Genes for Enzymes for the Activation of Precursors of Cytostatic Agents, for Example for Enzymes Which Convert or Cleave Inactive Precursor Substances (Prodrugs) Into Active Cytostatic Agents (Drugs)

Substances of this nature, and the prodrugs and drugs which are in each case affiliated with them, have already been reviewed by Deonarain et al. (Br. J. Cancer 70, 786 (1994)), Mullen, Pharmac. Ther. 63, 199 (1994)) and Harris et al. (Gene Ther. 1, 170 (1994)). For example, use is to be made of the DNA sequence for one of the following enzymes:

herpes simplex virus thymidine kinase
varicella zoster virus thymidine kinase
bacterial nitroreductase
bacterial β-glucuronidase
plant β-glucuronidase from Secale cereale
human β-glucuronidase
human carboxypeptidase (CB), for example mast cell CB-A, pancreatic CB-B or bacterial carboxypeptidase
bacterial β-lactamase
bacterial cytosine deaminase
human catalase or peroxidase
phosphatase, in particular human alkaline phosphatase, human acid prostate phosphatase or type 5 acid phosphatase
oxidase, in particular human lysyl oxidase or human acid D-aminooxidase
peroxidase, in particular human glutathione peroxidase, human eosinophilic peroxidase or human thyroid peroxidase
galactosidase 8.4.2. Therapy of Autoimmune Diseases and Inflammations 2.1. Target Cells:
proliferating endothelial cells or
macrophages and/or lymphocytes or
synovial cells 2.2. Promoters:
endothelial cell-specific and cell cycle-specific or
macrophage-specific and/or lymphocyte-specific and/or cell cycle-specific or
synovial cell-specific and/or cell cycle-specific 2.3. Effector Genes for the Therapy of Allergies, for Example for
IFNβ
IFNγ
IL-10
antibodies or antibody fragments against IL-4
soluble IL-4 receptors
IL-12
TGFβ

2.4. Effector Genes for Preventing the Rejection of Transplanted Organs, for Example for
IL-10
TGFβ
soluble IL-1 receptors
soluble IL-2 receptors
IL-1 receptor antagonists
soluble IL-6 receptors
immunosuppressive antibodies or their $V_H$ and $V_L$-containing fragments, or their $V_H$ and $V_L$ fragments which are bonded by way of a linker.

Immunosuppressive antibodies are, for example, antibodies which are specific for the T-cell receptor or its CD3 complex, or antibodies against CD4 or CD8 and also against the IL-2 receptor, the IL-1 receptor or the IL-4 receptor, or against the adhesion molecules CD2, LFA-1, CD28 or CD40

2.5. Effector Genes for the Therapy of Antibody-mediated Autoimmune Diseases, for Example for
TGFβ
IFNα
IFNβ
IFNγ
IL-12
soluble IL-4 receptors
soluble IL-6 receptors
immunosuppressive antibodies or their $V_H$ and $V_L$-containing fragments 2.6. Effector Genes for the Therapy of Cell-mediated Autoimmune Diseases, for Example for
IL-6
IL-9
IL-10
IL-13
TNFα or TNFβ
an immunosuppressive antibody or its $V_H$ and $V_L$-containing fragments 2.7. Effector Genes for Inhibitors of Cell Proliferation, Cytostatic or Cytotoxic Proteins and Enzymes for the Activation of Precursors of Cytostatic Agents Examples of genes which encode proteins of this nature have already been listed in the "effector genes for the therapy of tumors" section.

In the same form as already described in that passage, use can be made, within the meaning of the invention, of effector genes which encode fusion proteins formed from antibodies or Fab or rec. Fv fragments of these antibodies, or other ligands which are specific for the target cell, and the above-mentioned cytokines, growth factors, receptors, cytostatic or cytotoxic proteins and enzymes.

2.8. Effector Genes for the Therapy of Arthritis

Within the meaning of the invention, effector genes are selected whose expressed protein directly or indirectly inhibits the inflammation in, for example, the joint and/or promotes the reconstitution of extracellular matrix (cartilege, connective tissue) in the joint.

Examples are
IL-1 receptor antagonist (IL-1-RA); IL-1-RA inhibits the binding of IL-1α, and IL-1β
soluble IL-1 receptor; soluble IL-1 receptor binds and inactivates IL-1
IL-6 IL-6 increases the secretion of TIMP and superoxides and decreases the secretion of IL-1 and TNFα by synovial cells and chondrocytes
soluble TNF receptor soluble TNF receptor binds and inactivates TNF
IL-4
IL-4 inhibits the formation and secretion of IL-1, TNFα and MMP
IL-10 IL-10 inhibits the formation and secretion of IL-1, TNFα and MMP and increases the secretion of TIMP
insulin-like growth factor (IGF-1) IGF-1 stimulates the synthesis of extracellular matrix.
TGFβ, especially TGFβ1 and TGFβ2 TGFβ stimulates the synthesis of extracellular matrix.
superoxide dismutase
TIMP, especially TIMP-1, TIMP-2 or TIMP-3

8.4.3. Therapy of the Deficient Formation of Blood Cells 3.1. Target Cells:
proliferating, immature cells of the hematopoietic system, or
stromacells which are adjacent to the hematopoietic cells 3.2. Promoters:
specific for hematopoietic cells and/or cell cycle-specific
cell-nonspecific and cell cycle-specific 3.3. Effector Genes for the Therapy of Anemia, for Example for
  erythropoietin
3.4. Effector Genes for the Therapy of Leucopenia, for Example for
  G-CSF
  GM-CSF
  M-CSF
3.5. Effector Genes for the Therapy of Thrombocytopenia, for Example for
  IL-3
  leukemia inhibitory factor (LIF)
  IL-11
  thrombopoietin
8.4.4. Therapy of Damage to the Nervous System
4.1. Target Cells:
  glia cells or
  proliferating endothelial cells 4.2. Promoters:
  glia cell-specific and cell cycle-specific or
  endothelial cell-specific and cell cycle-specific or
  non-specific and cell cycle-specific
4.3. Effector Genes for Neuronal Growth Factors, for Example
  FGF
  nerve growth factor (NGF) brain-derived neurotrophic factor (BDNF)
  neurotrophin-3 (NT-3)
  neurotrophin-4 (NT-4)
  ciliary neurotrophic factor (CNTF)
4.4. Effector Genes for Enzymes, for Example for
  tyrosine hydroxylase
  dopadecarboxylase
4.5. Effector Genes for Cytokines and Their Inhibitors Which Inhibit or Neutralize the Neurotoxic Effect of TNFα, for Example for
  TGF
  soluble TNF receptors
  TNF receptors neutralize TNFα
  IL-10 IL-10 inhibits the formation of IFNγ, TNFα, IL-2 and IL-4
  soluble IL-1 receptors
  IL-1 receptor I
  IL-1 receptor II
  soluble IL-1 receptors neutralize the activity of IL-1
  IL-1 receptor antagonist
  soluble IL-6 receptors
8.4.5. Therapy of Disturbances of the Blood Coagulation System and the Blood Circulation System
5.1. Target Cells:
  endothelial cells or
  proliferating endothelial cells or
  somatic cells in the vicinity of endothelial cells and smooth muscle cells, or
  macrophages
5.2. Promoters:
  cell non-specific and cell cycle-specific or
  specific for endothelial cells, smooth muscle cells or macrophages and cell cycle-specific
5.3. Structural Genes for Inhibiting Coagulation or for Promoting Fibrinolysis, for Example for
  tissue plasminogen activator (tPA)
  urokinase-type plasminogen activator (uPA)
  hybrids of tPA and uPA
  protein C
  hirudin
  serine proteinase inhibitors (serpines), such as C-AS inhibitor, α1-antitrypsin or antithrombin III
  tissue factor pathway inhibitor (TFPI)
5.4. Effector Genes for Promoting Coagulation, for Example for
  F VIII
  F IX
  von Willebrand factor
  F XIII
  PAI-1
  PAI-2
  tissue factor and fragments thereof
5.5. Effector Genes for Angiogenesis Factors, for Example for
  VEGF
  FGF
5.6. Effector Genes for Lowering Blood Pressure, for Example for
  kallikrein
  endothelial cell nitric oxide synthase
5.7. Effector Genes for Inhibiting the Proliferation of Smooth Muscle Cells Following Injury to the Endothelial Layer, for Example for
  an antiproliferative, cytostatic or cytotoxic protein or
  an enzyme for cleaving precursors of cytostatic agents into cytostatic agents, as already listed above (under tumor) or
  a fusion protein composed of one of these active compounds and a ligand, for example an antibody or antibody fragments which are specific for muscle cells
5.8. Effector Genes for Other Blood Plasma Proteins, for Example for
  albumin
  C1 inactivator
  serum cholinesterase
  transferrin
  1-antritrypsin
8.4.6. Vaccinations
6.1. Target Cells:
  muscle cells or
  macrophages and/or lymphocytes
  endothelial cells
6.2. Promoters:
  non-specific and cell cycle-specific or
  target cell-specific and cell cycle-specific
6.3. Effector Genes for the Prophylaxis of Infectious Diseases The possibilities of producing effective vaccines conventionally are limited. The technology of DNA vaccines was developed as a consequence. However, these DNA vaccines raise questions with regard to their effectiveness (Fynan et al., Int. J. Immunopharm. 17, 79 (1995); Donnelly et al., Immunol. 2, 20 (1994)).

The efficacy of the DNA vaccines can be expected to be greater in accordance with this invention.

The active substance to be selected is the DNA for a protein which is formed by the infectious pathogen, which protein leads, by means of triggering an immune reaction, i.e. by means of antibody binding and/or by means of cytotoxic T lymphocytes, to the neutralization and/or destruction of the pathogen. So-called neutralization antigens of this nature are already being applied as vaccination antigens (see review in Ellis, Adv. Exp. Med. Biol. 327, 263 (1992)).

Within the meaning of the invention, preference is given to the DNA which encodes neutralization antigens from the following pathogens:
influenza A virus
HIV
rabies virus
HSV (herpes simplex virus)
RSV (respiratory syncytial virus)
parainfluenza virus
rotavirus
VZV (varicella zoster virus)
CMV (cytomegalovirus)
measles virus
HPV (human papillomavirus)
HBV (hepatitis B virus)
HCV (hepatitis C virus)
HDV (hepatitis D virus)
HEV (hepatitis E virus)
HAV (hepatitis A virus)
Vibrio cholerae antigen
Borrelia burgdorferi
Helicobacter pylori
malaria antigen However, within the meaning of the invention, active substances of this nature also include the DNA for an antiidiotype antibody or its antigen-binding fragments whose antigen-binding structures (the complementarity determining regions) constitute copies of the protein structure or carbohydrate structure of the neutralization antigen of the infectious pathogen.

Antiidiotype antibodies of this nature can, in particular, replace carbohydrate antigens in the case of bacterial infectious pathogens.

Antiidiotypic antibodies of this nature, and their cleavage products, have been reviewed by Hawkins et al. (J. Immunother. 14, 273 (1993)) and Westerink and Apicella (Springer Seminars in Immunopathol. 15, 227 (1993)).

6.4. Effector Genes for "Tumor Vaccines"

These include antigens on tumor cells. Antigens of this nature have been reviewed, for example, by Sedlacek et al., Contrib. to Oncol. 32, Karger Verlag, Munich (1988) and Contrib. to Oncol 43, Karger Verlag, Munich (1992).

Other examples are constituted by the genes for the following protein antigens or for the variable region ($V_L$, $V_H$) of antiidiotype antibodies corresponding to the following non-protein antigens:
gangliosides
sialyl Lewis
peptides on tumors which are recognized by T-cells
oncogene-expressed proteins
blood group antigens and their precursors
antigens on tumor-associated mucin
antigens on heat shock proteins 8.4.7. The Therapy of Chronic Infectious Diseases 7.1. Target cell:
liver cell
lymphocyte and/or macrophage
epithelial cell
endothelial cell
7.2. Promoters:
virus-specific or cell-specific and cell cycle-specific
7.3. Effector Genes, for Example for
a protein which exhibits cytostatic, apoptotic or cytotoxic effects.
an enzyme which cleaves a precursor of an antiviral or cytotoxic substance into the active substance.
7.4. Effector Genes for Antiviral Proteins
cytokines and growth factors which have an antiviral effect. These include, for example, IFNα, IFNβ, IFNγ, TNFβ, TNFα, IL-1 or TGFα
antibodies of a specificity which inactivates the respective virus, or their $V_H$ and $V_L$-containing fragments, or their $V_H$ and $V_L$ fragments which are bonded by way of a linker, and which are prepared as already described. Examples of antibodies against virus antigens are:
anti-HBV
anti-HCV
anti-HSV
anti-HPV
anti-HIV
anti-EBV
anti-HTLV
anti-Coxsackie virus
anti-Hantaan virus
a Rev-binding protein. These proteins bind to the Rev RNA and inhibit Rev-dependent post-transcriptional steps in retrovirus gene expression.
Examples of Rev-binding proteins are:
RBP9-27
RBP1-8U
RBP1-8D
pseudogenes of RBP1-8
ribozymes which digest the mRNA of genes for cell cycle control proteins or the mRNA of viruses. Ribozymes which are catalytic for HIV have, for example, been reviewed by Christoffersen et al., J. Med. Chem. 38, 2033 (1995).
7.5. Effector Genes for Antibacterial Proteins
The antibacterial proteins include, for example, antibodies which neutralize bacterial toxins or opsonize bacteria. These antibodies include, for example, antibodies against
Meningococci C or B
*E. coli*
Borrelia
Pseudomonas
*Helicobacter pylori*
*Staphylococcus aureus*
8.5. Combination of Identical or Different Effector Genes The invention furthermore relates to a self-enhancing and, where appropriate, pharmacologically controllable, expression system which comprises a combination of the DNA sequences of two identical or two different effector genes [components d) and d')]. In order to ensure expression of the two DNA sequences, a further promoter sequence or, preferably, the cDNA for an internal ribosome entry site (IRES) is intercallated, as a regulatory element, between the two effector genes.

An IRES makes it possible to express two DNA sequences which are linked to each other by way of an IRES.

IRESs of this nature have been described, for example, by Montford and Smith (TIG 11, 179 (1995); Kaufman et al., Nucl. Acids Res. 19, 4485 (1991); Morgan et al., Nucl. Acids Res. 20, 1293 (1992); Dirks et al., Gene 128, 247 (1993); Pelletier and Sonenberg, Nature 334, 320 (1988) and Sugitomo et al., BioTechn. 12, 694 (1994)).

For example, use can be made of the cDNA for the IRES sequence of poliovirus (position≦140 to ≧630 of the 5' UTR).

Preference is given, within the meaning of the invention, to linking effector genes, which exhibit an additive effect, by way of further promoter sequences or an IRES sequence.

The following combinations of effector genes are, for example, preferred, within the meaning of the invention, for
8.5.1. The Therapy of Tumors
   identical or different, cytostatic, apoptotic, cytotoxic or inflammatory proteins or
   identical or different enzymes for cleaving the precursor of a cytostatic agent
8.5.2. The Therapy of Autoimmune Diseases
   different cytokines or receptors possessing a synergistic effect for inhibiting the cellular and/or humoral immune reaction or
   different or identical TIMPs
8.5.3. The Therapy of the Deficient Formation of Blood Cells
   different, hierarchically sequential cytokines, such as IL-1, IL-3, IL-6 or GM-CSF and erythropoietin, G-CSF or thrombopoietin
8.5.4. The Therapy of Nerve Cell Damage
   a neuronal growth factor and a cytokine or the inhibitor of a cytokine
8.5.5. The Therapy of Disturbances of the Blood Coagulation System and the Blood Circulatory System
   an antithrombotic agent and a fibrinolytic agent (e.g. tPA or uPA) or
   a cytostatic, apoptotic or cytotoxic protein and an antithrombotic or a fibrinolytic agent
   several different, synergistically acting blood coagulation factors, for example F VIII and vWF or F VIII and F IX
8.5.6. Vaccinations
   an antigen and an immunostimulatory cytokine, such as IL-1α, IL-1β, IL-2, GM-CSF, IL-3 or IL-4 receptor
   different antigens of one infectious pathogen or of different infectious pathogens, or
   different antigens of one tumor type or of different tumor types
8.5.7. Therapy of Viral Infectious Diseases
   an antiviral protein and a cytostatic, apoptotic or cytotoxic protein
   antibodies against different surface antigens of a virus or several viruses
8.5.8. Therapy of Bacterial Infectious Diseases
   antibodies against different surface antigens and/or toxins of an organism
8.6. Insertion of Signal Sequences and Transmembrane Domains
8.6.1. Enhancement of the Translation In order to enhance the translation, the nucleotide sequence GCCACC or GCCGCC can be inserted at the 3' end of the promoter sequence and directly at the 5' end of the start signal (ATG) of the signal or transmembrane sequence (Kozak, J. Cell Biol. 108, 299 (1989)).

8.6.2. Facilitation of Secretion

In order to facilitate secretion of the expression product of the effector gene, the homologous signal sequence which may be contained in the DNA sequence of the effector gene can be replaced with a heterologous signal sequence which improves extracellular secretion.

Thus, the signal sequence for immunoglobulin (DNA position≦63 to ≧107; Riechmann et al., Nature 332, 323 (1988)) or the signal sequence for CEA (DNA position≦33 to ≧134; Schrewe et al., Mol. Cell Biol. 10, 2738 (1990); Berling et al., Cancer Res. 50, 6534 (1990)) or the signal sequence of the human respiratory syncytial virus glycoprotein (cDNA for amino acids≦38 to ≧50 or 48 to 65; Lichtenstein et al., J. Gen. Virol. 77, 109 (1996)) can, for example, be inserted.

8.6.3. Anchoring the Active Compound 3.1) A sequence for a transmembrane domain can be inserted, as an alternative, or in addition, to the signal sequence, for the purpose of anchoring the active compound in the cell membrane of the transduced cell which forms the active compound.

Thus, the transmembrane sequence of human macrophage colony-stimulating factor (DNA position≦1485 to ≧1554; Cosman et al., Behring Inst. Mitt. 83, 15 (1988)) or the DNA sequence for the signal and transmembrane region of human respiratory syncytial virus (RSV) glycoprotein G (amino acids 1 to 63 or their constituent sequences, amino acids 38 to 63; Vijaya et al., Mol. Cell Biol. 8, 1709 (1988); Lichtenstein et al., J. Gen. Virol. 77, 109 (1996)) or the DNA sequence for the signal and transmembrane region of influenza virus neuraminidase (amino acids 7 to 35 or the constituent sequence amino acids 7 to 27; Brown et al., J Virol. 62, 3824 (1988)) can, for example, be inserted between the promoter sequence and the sequence of the effector gene.

3.2) However, the nucleotide sequence for a glycophospholipid anchor can also be inserted for the purpose of anchoring the active compound in the cell membrane of the transduced cells which form the active compound.

The insertion of a glycophospholipid anchor is effected at the 3' end of the nucleotide sequence of the effector gene and can be effected in addition to the insertion of a signal sequence.

Glycophospholipid anchors have been described, for example, for CEA, for N-CAM and for other membrane proteins, such as Thy-1 (see review, Ferguson et al., Ann. Rev. Biochem. 57, 285 (1988)).

3.3) A further possibility for anchoring active compounds to the cell membrane in accordance with the present invention is that of using a DNA sequence for a ligand-active compound fusion protein. The specificity of the ligand of this fusion protein is directed against a membrane structure on the cell membrane of the selected target cell.

The ligands which bind to the surface of cells include, for example, antibodies or antibody fragments which are directed against structures on the surface of, for example,
   endothelial cells. These include, in particular, antibodies against the VEGF receptors and against kinin receptors or of muscle cells, such as antibodies against actin or antibodies against angiotensin II receptors or antibodies against receptors for growth factors, such as against EGF receptors or against PDGF receptors or against FGF receptors or antibodies against endothelin A receptors
   the ligands also include antibodies or their fragments which are directed against tumor-specific or tumor-associated antigens on the tumor cell membrane. Antibodies of this nature have already been described.

The murine monoclonal antibodies are preferably to be employed in humanized form. Fab and rec. Fv fragments, and their fusion products, are prepared using the technology known to the skilled person, as already described.

The ligands furthermore include all active compounds, such as cytokines or adhesion molecules, growth factors or their fragments or constituent sequences thereof, or mediators or peptide hormones which bind to membrane structures or membrane receptors on the respective cell selected. Examples are ligands for endothelial cells, such as IL-1, PDGF, bFGF, VEGF, TGGβ or kinin and derivatives or analogs of kinin they furthermore include adhesion molecules. Adhesion molecules of this nature, such as SLex, LFA-1, MAC-1, LeCAM-1, VLA-4 or vitronectin, or derivatives or analogs of vitronectin, have already been described for endothelial cells (reviews in Augustin-Voss et al., J. Cell Biol. 119, 483 (1992); Pauli et al., Cancer Metast. Rev. 9, 175 (1990); Honn et al., Cancer Metast. Rev. 11, 353 (1992); Varner et al., Cell Adh. Commun. 3, 367 (1995)).

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications and patent applications cited herein, including Federal Republic of Germany Application No. 19756975.7, are expressly incorporated herein by reference in their entireties to the same extend as if they were incorporated by reference individually.

We claim:

1. A nucleic acid construct comprising:
(a) a first activation sequence;
(b) a chimeric transcription factor gene, the transcription of which is induced by activation of the first activation sequence, comprising:
  (1) a nucleic acid sequence which encodes an activation domain,
  (2) a nucleic acid sequence which encodes an amino acid sequence for binding an inhibitor, wherein the amino acid sequence is murine p163 or a fragment thereof, and
  (3) a nucleic acid sequence which encodes a DNA-binding domain,
wherein the nucleic acid sequences of steps b(1), b(2) and b(3) are operatively linked to produce a chimeric transcription factor;
(c) a second activation sequence that is activated by binding of the chimeric transcription factor gene; and
(d) an effector gene, the transcription of which is induced by the activation of the second activation sequence.

2. A nucleic acid construct according to claim 1, wherein the first activation sequence and the second activation sequence are the same.

3. A nucleic acid construct according to claim 1, wherein the first activation sequence is activated non-specifically, cell-specifically, metabolically specifically, virus-specifically and/or cell cycle-specifically.

4. A nucleic acid construct according to claim 3, wherein the first activation sequence is selected from the group consisting of promoters which are activated in endothelial cells, peritoneal cells, pleural cells, epithelial cells of the skin, epithelial cells of the lung, epithelial cells of the gastrointestinal tract, epithelial cells of the kidney, epithelial cells of the urinary tracts, muscle cells, connective tissue cells, hematopoietic cells, macrophages, lymphocytes, leukemia cells, tumor cells or glia cells; promoter sequences of viruses; promoter or enhancer sequences which are activated by hypoxia or cell cycle-specific activation sequences of the genes for cdc25C, cyclin A, cdc2, E2F-1, B-myb, or DHFR; and sequences for binding transcription factors which appear or are activated in a cell proliferation-dependent manner.

5. A nucleic acid construct according to claim 4, wherein the promoter sequences of viruses are selected from the group of viruses consisting of HBV, HCV, HSV, HPV, EBV, HTLV, CMV and HIV.

6. A nucleic acid construct according to claim 4, wherein the sequences for binding transcription factors which appear or are activated in a cell proliferation-dependent manner are monomers or multimers of the Myc E box.

7. A nucleic acid construct according to claim 1, wherein the activation domain of the transcriptional factor gene is selected from the group consisting of the activation domains of Oct-2, Sp1, NFY, ITF-2, VP-16, c-Myc and CTF.

8. A nucleic acid construct according to claim 1, wherein the nucleic acid sequence for binding an inhibitor encodes the amino acid sequence of p163 depicted in FIG. 6 (SEQ ID NO: 24) or fragment thereof.

9. A nucleic acid construct according to claim 8, wherein the sequence for binding encodes a peptide, the amino acid sequence of which is selected from the group consisting of position 1 to 24, position 137 to 196, position 215 to 265, position 239 to 272, position 399 to 438, and position 307 to 469, wherein the position numbering corresponds to the numbering in FIG. 6 (SEQ ID NO: 24).

10. A nucleic acid construct according to claim 8, wherein the nucleic acid sequence which encodes an amino acid sequence for the binding an inhibitor comprises a deletion or mutation in the p27-binding domain.

11. A nucleic acid construct according to claim 10, wherein the nucleic acid sequence encodes the amino acid sequence of FIG. 8 (SEQ ID NO: 26).

12. A nucleic acid construct according to claim 8, wherein the nucleic acid sequence which encodes an amino acid sequence for the binding an inhibitor comprises a deletion of mutation in the Ran-binding domain.

13. A nucleic acid construct according to claim 12, wherein the nucleic acid sequence for binding of an inhibitor encodes the amino acid sequence of p163 depicted in FIG. 9 (SEQ ID NO: 27).

14. A nucleic acid construct according to claim 1, wherein the nucleic acid sequence for binding an inhibitor encodes the p27-binding domain of p163.

15. A nucleic acid construct according to claim 14, wherein the nucleic acid sequence for binding an inhibitor encodes the amino acid sequence depicted in FIG. 10 (SEQ ID NO 28).

16. A nucleic acid construct according to claim 1, wherein the nucleic acid sequence for binding an inhibitor is the nucleic acid sequence depicted in FIG. 3 (SEQ ID NO: 9).

17. A nucleic acid construct according to claim 1, wherein the second activation sequence comprises at least one DNA sequence for binding the transcription factor.

18. A nucleic acid construct according to claim 17, wherein the second activation sequence is selected from the group consisting of

- (5'-CGGACAACTGTTGACCG-3', SEQ ID NO.: 1) for binding the Ga14 protein;
- (5'-TACTGTATGTACATACAGTA-3', SEQ ID NO.: 2) for binding the LexA protein; the sequence (5'-GAATTGTGAGCGCTCACAATTC-3, SEQ ID NO.: 3) for binding the Lac I repressor protein;
- (5'-TCGAGTTTACCACTCCCTATCAGTGATAGAGA AAAGTGAAAG-3', SEQ ID NO.: 4) for binding the tetracycline repressor protein; and
- (5'-TAATGATGGGCG-3', SEQ ID NO.: 5) for binding the ZFHD-1 protein.

19. A nucleic acid construct according to claim 1, wherein the effector gene encodes an active compound selected from the group consisting of cytokines, chemokines, growth factors, receptors for cytokines, chemokines or growth factors, proteins having an antiproliferative or cytostatic or apoptotic effect, antibodies, antibody fragments, angiogenesis inhibitors, peptide hormones, coagulation factors, coagulation inhibitors, fibrinolytic proteins, peptides or proteins having an effect on the blood circulation, blood plasma proteins and antigens of infectious pathogens and, of cells or of tumors, with the selected antigen bringing about an immune reaction.

20. A nucleic acid construct according to claim 1, wherein the effector gene encodes an enzyme which converts a precursor of a drug into a drug.

21. A nucleic acid construct according to claim 1, wherein the effector gene encodes a ligand-active compound fusion protein or a ligand-enzyme fusion protein, wherein the ligand is selected from the group consisting of cytokines, growth factors, antibodies, antibody fragments, peptide hormones, mediators, and cell adhesion molecules.

22. The nucleic acid construct according to claim 1, wherein the nucleic acid is DNA.

23. A vector comprising the nucleic acid construct of claim 1.

24. A vector according to claim 23, wherein the vector is a plasmid vector.

25. A vector according to claim 23, wherein the vector is a viral vector.

26. An isolated cell comprising the nucleic acid construct of claim 1.

27. A method for producing an effector protein comprising culturing the isolated cell of claim 26 under conditions suitable for expression of said nucleic acid construct.

28. A method of making a nucleic acid construct according to claim 1 comprising ligating in stepwise order;

(a) a first activation sequence;

(b) a chimeric transcription factor gene, the transcription of which is induced by activation of the first activation sequence, comprising:

(1) a nucleic acid sequence which encodes an activation domain, (2) a nucleic acid sequence which encodes an amino acid sequence for binding an inhibitor, wherein the amino acid sequence is murine p163 or a fragment thereof, and (3) a nucleic acid sequence which encodes a DNA-binding domain, wherein the nucleic acid sequences of steps b(1), b(2) and b(3) are operatively linked to produce a chimeric transcription factor;

(c) a second activation sequence that is activated by binding of the chimeric transcription factor gene; and (d) an effector gene, the transcription of which is induced by the activation of the second activation sequence.

* * * * *

SEQUENCE LISTING

<160> NUMBER OF SEQ ID NOS: 57

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
cggacaactg ttgaccg                                                      17

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
tactgtatgt acatacagta                                                   20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
gaattgtgag cgctcacaat tc                                                22

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
tcgagtttac cactccctat cagtgataga gaaaagtgaa ag                          42

-continued

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
taatgatggg cg                                                     12

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ggaagcagac cacgtggtct gcttcc                                      26

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
agcaggtgtt gggaggc                                                17

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
ggccgatggg cagatagagg gggccgatgg gcagatagag g                     41

<210> SEQ ID NO 9
<211> LENGTH: 1958
<212> TYPE: DNA
<213> ORGANISM: Murine sp.

<400> SEQUENCE: 9
tcgaattggg taccgggccc ccctcgagg tcgacggtat cgataagctt gatatcgaat    60
tcgcggccgc tcgagttaca agatggcggc cccgggcgct ctcttcaccg ttctgtagca   120
gcttcgggct gagcggatgt ctcttcttgt cctcagtgtc ggactcagag acacacggct   180
cccgagttct gctgatcacg aagttcccgg aggcgctcga cgcaccggaa tctcccagcg   240
gccgcgaccg ccgcctcggc cctgctcgcc gggcgccgg gactccagcg tgatcggcgg    300
cggcagtcaa ggttcacaaa aatggcgaag agagttgcgg agaaggagtt gactgacagg   360
aactgggatg aggaagacga agttgaagag atgggaacat tctcagtggc cagtgaggaa   420
gtcatgaaga acagagccgt aaagaaggca aagcgcagaa acgttggatt tgaatctgat   480
agcggaggag cctttaaagg tttcaaaggt ttggttgtgc cttctggagg aggagggttt   540
tctggatttg gtggctctgg aggaaaagcct ctggaaggac tgacaaatgg aaacagcaca   600

-continued

```
gacaatgcca cgcccttctc caatgtaaag acagcagcag agcccaaggc agcctttggt      660
tcttttgctg tgaatggccc tactaccttg gtggataaag tttcaaatcc aaaaactaat      720
ggggacagca atcagccgcc ctcctccggc cctgcttcca gtaccgcctg ccctgggaat      780
gcctatcaca agcagctggc tggcttgaac tgctccgtcc gcgattggat agtgaagcac      840
gtgaacacaa acccgctttg tgacctgact cccatttttta aagactatga gagatacttg     900
gcgacgatcg agaagcagct tgagaatgga ggcggcagca gttctgagag ccagacagac      960
agggcgacgc tggaatgga gcctccttcc cttttttggtt caacaaaact acagcaagag     1020
tcaccatttt catttcatgg caacaaagcg gaggacacat ctgaaaaggt ggagtttaca     1080
gcagaaaaga aatcggacgc agcacaagga gcaacaagtg cctcgtttag tttcggcaag    1140
aaaattgaga gctcggcttt gggctcgtta agctctggct ccctaactgg gttttcattc    1200
tctgctggaa gctccagctt gtttggtaaa gatgctgccc agagtaaagc agcctcttcg    1260
ctgttctctg ctaaagcatc cgagagtccg gcaggaggcg gcagcagcga gtgcagagat    1320
ggtgaagaag aggagaatga cgagccaccc aaggtagtgg tgaccgaagt aaaggaagag    1380
gatgctttct actccaaaaa atgtaaacta ttttacaaga aagacaacga atttaaagag    1440
aagggtgtgg ggaccctgca tttaaaaccc acagcaactc agaagaccca gctcttggtg    1500
cgggcagaca ccaacctagg caacatactg ctgaatgttc tgatcgcccc caacatgccg    1560
tgcacccgga caggaaagaa caacgtcctt atcgtctgtg tccccaaccc cccactcgat    1620
gagaagcagc ccactctccc ggccaccatg ctgatccggg tgaagacgag cgaggatgcc    1680
gatgaattgc acaagatttt actggagaaa aaggatgcct gagcactgag gctgaccaag    1740
gcatgttgcc acgttgctgc ttcccctccg tccctaactt agtcacattc tttcctcttc    1800
tactgtgaca ttctgagaac ttctaggtaa cttgaacttt tgtgaggaag attaaggcca    1860
ataaatcctt tcagtggcgg ccgcgaattc ctgcagcccg ggggatccac tagttctaga    1920
gcggccgcca ccgcggtgga gctccagctt ttgggaga                            1958
```

```
<210> SEQ ID NO 10
<211> LENGTH: 24
<212> TYPE: PRT
<213> ORGANISM: Murine sp.

<400> SEQUENCE: 10

Met Ala Lys Arg Val Ala Glu Lys Glu Leu Thr Asp Arg Asn Trp Asp
  1               5                  10                  15

Glu Glu Asp Glu Val Glu Glu Met
            20

<210> SEQ ID NO 11
<211> LENGTH: 24
<212> TYPE: PRT
<213> ORGANISM: Saccharomyces cerevisiae

<400> SEQUENCE: 11

Met Ala Lys Arg Val Ala Asp Ala Gln Ile Gln Arg Glu Thr Tyr Asp
  1               5                  10                  15

Ser Asn Glu Ser Asp Asp Val
            20

<210> SEQ ID NO 12
<211> LENGTH: 60
<212> TYPE: PRT
<213> ORGANISM: Murine sp.
```

-continued

```
<400> SEQUENCE: 12

Asn Gln Pro Pro Ser Ser Gly Pro Ala Ser Ser Thr Ala Cys Pro Gly
  1               5                  10                  15

Asn Ala Tyr His Lys Gln Leu Ala Gly Leu Asn Cys Ser Val Arg Asp
             20                  25                  30

Trp Ile Val Lys His Val Asn Thr Asn Pro Leu Cys Asp Leu Thr Pro
         35                  40                  45

Ile Phe Lys Asp Tyr Glu Arg Tyr Leu Ala Thr Ile
     50                  55                  60

<210> SEQ ID NO 13
<211> LENGTH: 60
<212> TYPE: PRT
<213> ORGANISM: Saccharomyces cerevisiae

<400> SEQUENCE: 13

Asn Arg Ala Asp Gly Thr Gly Glu Ala Gln Val Asp Asn Ser Pro Thr
  1               5                  10                  15

Thr Glu Ser Asn Ser Arg Leu Lys Ala Leu Asn Leu Gln Phe Lys Ala
             20                  25                  30

Lys Val Asp Asp Leu Val Leu Gly Lys Pro Leu Ala Asp Leu Arg Pro
         35                  40                  45

Leu Phe Thr Arg Tyr Glu Leu Tyr Ile Lys Asn Ile
     50                  55                  60

<210> SEQ ID NO 14
<211> LENGTH: 51
<212> TYPE: PRT
<213> ORGANISM: Murine sp.

<400> SEQUENCE: 14

Ala Thr Ala Gly Met Glu Pro Pro Ser Leu Phe Gly Ser Thr Lys Leu
  1               5                  10                  15

Gln Gln Glu Ser Pro Phe Ser Phe His Gly Asn Lys Ala Glu Asp Thr
             20                  25                  30

Ser Glu Lys Val Glu Phe Thr Ala Glu Lys Lys Ser Asp Ala Ala Gln
         35                  40                  45

Gly Ala Thr
     50

<210> SEQ ID NO 15
<211> LENGTH: 51
<212> TYPE: PRT
<213> ORGANISM: Saccharomyces cerevisiae

<400> SEQUENCE: 15

Ala Asn Ser Ser Thr Ser Pro Ala Pro Ser Ile Pro Ser Thr Gly Phe
  1               5                  10                  15

Lys Phe Ser Leu Pro Phe Glu Gln Lys Gly Ser Gln Thr Thr Thr Asn
             20                  25                  30

Asp Ser Lys Glu Glu Ser Thr Thr Glu Ala Thr Gly Asn Glu Ser Gln
         35                  40                  45

Asp Ala Thr
     50

<210> SEQ ID NO 16
<211> LENGTH: 34
<212> TYPE: PRT
```

```
<213> ORGANISM: Murine sp.

<400> SEQUENCE: 16

His Gly Asn Lys Ala Glu Asp Thr Ser Glu Lys Val Glu Phe Thr Ala
 1               5                  10                  15

Glu Lys Lys Ser Asp Ala Ala Gln Gly Ala Thr Ser Ala Ser Phe Ser
                20                  25                  30

Phe Gly

<210> SEQ ID NO 17
<211> LENGTH: 34
<212> TYPE: PRT
<213> ORGANISM: Saccharomyces cerevisiae

<400> SEQUENCE: 17

Asn Gly Ser Glu Ser Lys Asp Ser Asp Lys Pro Ser Leu Pro Ser Ala
 1               5                  10                  15

Val Asp Gly Glu Asn Asp Lys Lys Glu Ala Thr Lys Pro Ala Phe Ser
                20                  25                  30

Phe Gly

<210> SEQ ID NO 18
<211> LENGTH: 40
<212> TYPE: PRT
<213> ORGANISM: Murine sp.

<400> SEQUENCE: 18

Leu Gly Asn Ile Leu Leu Asn Val Leu Ile Ala Pro Asn Met Pro Cys
 1               5                  10                  15

Thr Arg Thr Gly Lys Asn Asn Val Leu Ile Val Cys Val Pro Asn Pro
                20                  25                  30

Pro Leu Asp Glu Lys Gln Pro Thr
            35                  40

<210> SEQ ID NO 19
<211> LENGTH: 40
<212> TYPE: PRT
<213> ORGANISM: Saccharomyces cerevisiae

<400> SEQUENCE: 19

Met Gly Asn Val Leu Leu Asn Ala Thr Val Val Asp Ser Phe Lys Tyr
 1               5                  10                  15

Glu Pro Leu Ala Pro Gly Asn Asp Asn Leu Ile Lys Ala Pro Thr Val
                20                  25                  30

Ala Ala Asp Gly Lys Leu Val Thr
            35                  40

<210> SEQ ID NO 20
<211> LENGTH: 157
<212> TYPE: PRT
<213> ORGANISM: Murine sp.

<400> SEQUENCE: 20

Asp Ser His Ala Asp His Asp Thr Ser Thr Glu Asn Ala Asp Glu Ser
 1               5                  10                  15

Thr Thr His Pro Gln Phe Glu Pro Ile Val Ser Val Pro Glu Gln Glu
                20                  25                  30

Ile Lys Thr Leu Glu Glu Asp Glu Glu Leu Phe Lys Met Arg Ala
            35                  40                  45
```

```
Lys Leu Phe Arg Phe Ala Ser Glu Asn Asp Leu Pro Glu Trp Lys Glu
 50                  55                  60

Pro Arg His Gly Asp Val Lys Leu Leu Lys His Lys Glu Lys Gly Thr
 65                  70                  75                  80

Ile Arg Leu Leu Met Arg Arg Asp Lys Thr Leu Lys Ile Cys Ala Asn
                 85                  90                  95

His Tyr Ile Thr Pro Met Met Glu Leu Lys Pro Asn Ala Gly Ser Asp
                100                 105                 110

Arg Ala Trp Val Trp Asn Thr His Thr Asp Phe Ala Asp Glu Cys Pro
                115                 120                 125

Lys Pro Glu Leu Leu Ala Ile Arg Phe Leu Asn Ala Glu Asn Ala Gln
130                 135                 140

Lys Phe Lys Thr Lys Phe Glu Glu Cys Arg Lys Glu Ile
145                 150                 155

<210> SEQ ID NO 21
<211> LENGTH: 157
<212> TYPE: PRT
<213> ORGANISM: Homo sapiens

<400> SEQUENCE: 21

Asp Ser His Ala Asp His Asp Thr Ser Thr Glu Asn Ala Asp Glu Ser
  1                   5                  10                  15

Asn His Asp Pro Gln Phe Glu Pro Ile Val Ser Val Pro Glu Gln Glu
                 20                  25                  30

Ile Lys Thr Leu Glu Glu Asp Glu Glu Leu Phe Lys Met Arg Ala
                 35                  40                  45

Lys Leu Phe Arg Phe Ala Ser Glu Asn Asp Leu Pro Glu Trp Lys Glu
 50                  55                  60

Arg Gly Thr Gly Asp Val Lys Leu Leu Lys His Lys Glu Lys Gly Thr
 65                  70                  75                  80

Ile Arg Leu Leu Met Arg Arg Asp Lys Thr Leu Lys Ile Cys Ala Asn
                 85                  90                  95

His Tyr Ile Thr Pro Met Met Glu Leu Lys Pro Asn Ala Gly Ser Asp
                100                 105                 110

Arg Ala Trp Val Trp Asn Thr His Thr Asp Phe Ala Asp Glu Cys Pro
                115                 120                 125

Lys Pro Glu Leu Leu Ala Ile Arg Phe Leu Asn Ala Glu Asn Ala Gln
130                 135                 140

Lys Phe Lys Thr Lys Phe Glu Glu Cys Arg Lys Glu Ile
145                 150                 155

<210> SEQ ID NO 22
<211> LENGTH: 158
<212> TYPE: PRT
<213> ORGANISM: Saccharomyces cerevisiae

<400> SEQUENCE: 22

Ser Gln Thr Thr Thr Asn Asp Ser Lys Glu Glu Ser Thr Thr Glu Ala
  1                   5                  10                  15

Thr Gly Asn Glu Ser Gln Asp Ala Thr Lys Val Asp Ala Thr Pro Glu
                 20                  25                  30

Glu Ser Lys Pro Ile Asn Leu Gln Asn Gly Glu Glu Asp Glu Val Ala
                 35                  40                  45

Leu Phe Ser Gln Lys Ala Lys Leu Met Thr Phe Asn Ala Glu Thr Lys
 50                  55                  60
```

```
Ser Tyr Asp Ser Arg Gly Val Gly Glu Met Lys Leu Lys Lys Lys
 65                  70                  75                  80

Asp Asp Ser Pro Lys Val Arg Leu Leu Cys Arg Ser Asp Gly Met Gly
                 85                  90                  95

Asn Val Leu Leu Asn Ala Thr Val Val Asp Ser Phe Lys Tyr Glu Pro
                100                 105                 110

Leu Ala Pro Gly Asn Asp Asn Leu Ile Lys Ala Pro Thr Val Ala Ala
            115                 120                 125

Asp Gly Lys Leu Val Thr Tyr Ile Val Phe Lys Gln Lys Leu Glu Gly
        130                 135                 140

Arg Ser Phe Thr Lys Ala Ile Glu Asp Ala Lys Lys Glu Met
145                 150                 155
```

<210> SEQ ID NO 23
<211> LENGTH: 160
<212> TYPE: PRT
<213> ORGANISM: Murine sp.

<400> SEQUENCE: 23

```
Gln Ser Lys Ala Ala Ser Ser Leu Phe Ser Ala Lys Ala Ser Glu Ser
  1               5                  10                  15

Pro Ala Gly Gly Gly Ser Ser Glu Cys Arg Asp Gly Glu Glu Glu Glu
                 20                  25                  30

Asn Asp Glu Pro Pro Lys Val Val Thr Glu Val Lys Glu Glu Asp
                 35                  40                  45

Ala Phe Tyr Ser Lys Lys Cys Lys Leu Phe Tyr Lys Lys Asp Asn Glu
             50                  55                  60

Phe Lys Glu Lys Gly Val Gly Thr Leu His Leu Lys Pro Thr Ala Thr
 65                  70                  75                  80

Gln Lys Thr Gln Leu Leu Val Arg Ala Asp Thr Asn Leu Gly Asn Ile
                 85                  90                  95

Leu Leu Asn Val Leu Ile Ala Pro Asn Met Pro Cys Thr Arg Thr Gly
                100                 105                 110

Lys Asn Asn Val Leu Ile Val Cys Val Pro Asn Pro Leu Asp Glu Lys
            115                 120                 125

Gln Pro Thr Leu Pro Ala Thr Met Leu Ile Arg Val Lys Thr Ser Glu
        130                 135                 140

Asp Ala Asp Glu Leu His Lys Ile Leu Leu Glu Lys Lys Asp Ala Ala
145                 150                 155                 160
```

<210> SEQ ID NO 24
<211> LENGTH: 466
<212> TYPE: PRT
<213> ORGANISM: Murine sp.

<400> SEQUENCE: 24

```
Met Ala Lys Arg Val Ala Glu Lys Glu Leu Thr Asp Arg Asn Trp Asp
  1               5                  10                  15

Glu Glu Asp Glu Val Glu Met Gly Thr Phe Ser Val Ala Ser Glu
                 20                  25                  30

Glu Val Met Lys Asn Arg Ala Val Lys Ala Lys Arg Arg Asn Val
             35                  40                  45

Gly Phe Glu Ser Asp Ser Gly Ala Phe Lys Gly Phe Lys Gly Leu
         50                  55                  60

Val Val Pro Ser Gly Gly Gly Phe Ser Gly Phe Gly Gly Ser Gly
 65                  70                  75                  80
```

-continued

Gly Lys Pro Leu Glu Gly Leu Thr Asn Gly Asn Ser Thr Asp Asn Ala
            85                  90                  95

Thr Pro Phe Ser Asn Val Lys Thr Ala Ala Glu Pro Lys Ala Ala Phe
            100                 105                 110

Gly Ser Phe Ala Val Asn Gly Pro Thr Thr Leu Val Asp Lys Val Ser
            115                 120                 125

Asn Pro Lys Thr Asn Gly Asp Ser Asn Gln Pro Pro Ser Ser Gly Pro
            130                 135                 140

Ala Ser Ser Thr Ala Cys Pro Gly Asn Ala Tyr His Lys Gln Leu Ala
145                 150                 155                 160

Gly Leu Asn Cys Ser Val Arg Asp Trp Ile Val Lys His Val Asn Thr
            165                 170                 175

Asn Pro Leu Cys Asp Leu Thr Pro Ile Phe Lys Asp Tyr Glu Arg Tyr
            180                 185                 190

Leu Ala Thr Ile Glu Lys Gln Leu Glu Asn Gly Gly Ser Ser Ser
            195                 200                 205

Glu Ser Gln Thr Asp Arg Ala Thr Ala Gly Met Glu Pro Pro Ser Leu
            210                 215                 220

Phe Gly Ser Thr Lys Leu Gln Gln Glu Ser Pro Phe Ser Phe His Gly
225                 230                 235                 240

Asn Lys Ala Glu Asp Thr Ser Glu Lys Val Glu Phe Thr Ala Glu Lys
            245                 250                 255

Lys Ser Asp Ala Ala Gln Gly Ala Thr Ser Ala Ser Phe Ser Phe Gly
            260                 265                 270

Lys Lys Ile Glu Ser Ser Ala Leu Gly Ser Leu Ser Ser Gly Ser Leu
            275                 280                 285

Thr Gly Phe Ser Phe Ser Ala Gly Ser Ser Ser Leu Phe Gly Lys Asp
            290                 295                 300

Ala Ala Gln Ser Lys Ala Ala Ser Ser Leu Phe Ser Ala Lys Ala Ser
305                 310                 315                 320

Glu Ser Pro Ala Gly Gly Gly Ser Ser Glu Cys Arg Asp Gly Glu Glu
            325                 330                 335

Glu Glu Asn Asp Glu Pro Pro Lys Val Val Thr Glu Val Lys Glu
            340                 345                 350

Glu Asp Ala Phe Tyr Ser Lys Lys Cys Lys Leu Phe Tyr Lys Lys Asp
            355                 360                 365

Asn Glu Phe Lys Glu Lys Gly Val Gly Thr Leu His Leu Lys Pro Thr
            370                 375                 380

Ala Thr Gln Lys Thr Gln Leu Leu Val Arg Ala Asp Thr Asn Leu Gly
385                 390                 395                 400

Asn Ile Leu Leu Asn Val Leu Ile Ala Pro Asn Met Pro Cys Thr Arg
            405                 410                 415

Thr Gly Lys Asn Asn Val Leu Ile Val Cys Val Pro Asn Pro Pro Leu
            420                 425                 430

Asp Glu Lys Gln Pro Thr Leu Pro Ala Thr Met Leu Ile Arg Val Lys
            435                 440                 445

Thr Ser Glu Asp Ala Asp Glu Leu His Lys Ile Leu Leu Glu Lys Lys
    450                 455                 460

Asp Ala
465

<210> SEQ ID NO 25
<211> LENGTH: 715
<212> TYPE: PRT

<213> ORGANISM: Saccharomyces cerevisiae

<400> SEQUENCE: 25

```
Met Ala Lys Arg Val Ala Asp Ala Gln Ile Gln Arg Glu Thr Tyr Asp
  1               5                  10                  15
Ser Asn Glu Ser Asp Asp Val Thr Pro Ser Thr Lys Val Ala Ser
             20                  25                  30
Ser Ala Val Met Asn Arg Arg Lys Ile Ala Met Pro Lys Arg Arg Met
         35                  40                  45
Ala Phe Lys Pro Phe Gly Ser Ala Lys Ser Asp Glu Thr Lys Gln Ala
     50                  55                  60
Ser Ser Phe Ser Phe Leu Asn Arg Ala Asp Gly Thr Gly Glu Ala Gln
 65                 70                  75                  80
Val Asp Asn Ser Pro Thr Thr Glu Ser Asn Ser Arg Leu Lys Ala Leu
                 85                  90                  95
Asn Leu Gln Phe Lys Ala Lys Val Asp Asp Leu Val Leu Gly Lys Pro
            100                 105                 110
Leu Ala Asp Leu Arg Pro Leu Phe Thr Arg Tyr Glu Leu Tyr Ile Lys
        115                 120                 125
Asn Ile Leu Glu Ala Pro Val Lys Phe Ile Glu Asn Pro Thr Gln Thr
130                 135                 140
Lys Gly Asn Asp Ala Lys Pro Ala Lys Val Glu Asp Val Gln Lys Ser
145                 150                 155                 160
Ser Asp Ser Ser Glu Asp Glu Val Lys Val Glu Gly Pro Lys Phe
                165                 170                 175
Thr Ile Asp Ala Lys Pro Pro Ile Ser Asp Ser Val Phe Ser Phe Gly
            180                 185                 190
Pro Lys Lys Glu Asn Arg Lys Lys Asp Glu Ser Asp Ser Glu Asn Asp
        195                 200                 205
Ile Glu Ile Lys Gly Pro Glu Phe Lys Phe Ser Gly Thr Val Ser Ser
    210                 215                 220
Asp Val Phe Lys Leu Asn Pro Ser Thr Asp Lys Asn Glu Lys Lys Thr
225                 230                 235                 240
Glu Thr Asn Ala Lys Pro Phe Ser Phe Ser Ser Ala Thr Ser Thr Thr
                245                 250                 255
Glu Gln Thr Lys Ser Lys Asn Pro Leu Ser Leu Thr Glu Ala Thr Lys
            260                 265                 270
Thr Asn Val Asp Asn Ser Lys Ala Glu Ala Ser Phe Thr Phe Gly
        275                 280                 285
Thr Lys His Ala Ala Asp Ser Gln Asn Asn Lys Pro Ser Phe Val Phe
    290                 295                 300
Gly Gln Ala Ala Ala Lys Pro Ser Leu Glu Lys Ser Ser Phe Thr Phe
305                 310                 315                 320
Gly Ser Thr Thr Ile Glu Lys Lys Asn Asp Glu Asn Ser Thr Ser Asn
                325                 330                 335
Ser Lys Pro Glu Lys Ser Ser Asp Ser Asn Asp Ser Asn Pro Ser Phe
            340                 345                 350
Ser Phe Ser Ile Pro Ser Lys Asn Thr Pro Asp Ala Ser Lys Pro Ser
        355                 360                 365
Phe Asn Phe Gly Val Pro Asn Ser Ser Lys Asn Glu Thr Ser Lys Pro
    370                 375                 380
Val Phe Ser Phe Gly Ala Ala Thr Pro Ser Ala Lys Glu Ala Ser Gln
385                 390                 395                 400
```

```
Glu Asp Asp Asn Asn Val Glu Lys Pro Ser Ser Lys Pro Ala Phe
                405                 410                 415

Asn Phe Ile Ser Asn Ala Gly Thr Glu Lys Glu Lys Glu Ser Lys Lys
            420                 425                 430

Asp Ser Lys Pro Ala Phe Ser Phe Gly Ile Ser Asn Gly Ser Glu Ser
        435                 440                 445

Lys Asp Ser Asp Lys Pro Ser Leu Pro Ser Ala Val Asp Gly Glu Asn
    450                 455                 460

Asp Lys Lys Glu Ala Thr Lys Pro Ala Phe Phe Gly Ile Asn Thr Asn
465                 470                 475                 480

Thr Thr Lys Thr Ala Asp Thr Lys Ala Pro Thr Phe Thr Phe Gly Ser
                485                 490                 495

Ser Ala Leu Ala Asp Asn Lys Glu Asp Val Lys Lys Pro Phe Ser Phe
            500                 505                 510

Gly Thr Ser Gln Pro Asn Asn Thr Pro Ser Phe Ser Phe Gly Lys Thr
        515                 520                 525

Thr Ala Asn Leu Pro Ala Asn Ser Ser Thr Ser Pro Ala Pro Ser Ile
    530                 535                 540

Pro Ser Thr Gly Phe Lys Phe Ser Leu Pro Phe Glu Gln Lys Gly Ser
545                 550                 555                 560

Gln Thr Thr Thr Asn Asp Ser Lys Glu Glu Ser Thr Thr Glu Ala Thr
                565                 570                 575

Gly Asn Glu Ser Gln Asp Ala Thr Lys Val Asp Ala Thr Pro Glu Glu
            580                 585                 590

Ser Lys Pro Ile Asn Leu Gln Asn Gly Glu Glu Asp Glu Val Ala Leu
        595                 600                 605

Phe Ser Lys Ala Lys Leu Met Thr Phe Asn Ala Glu Thr Lys Ser Tyr
    610                 615                 620

Asp Ser Arg Gly Val Gly Glu Met Lys Leu Leu Lys Lys Lys Asp Asp
625                 630                 635                 640

Pro Ser Lys Val Arg Leu Leu Cys Arg Ser Asp Gly Met Gly Asn Val
                645                 650                 655

Leu Leu Asn Ala Thr Val Val Asp Ser Phe Lys Tyr Glu Pro Leu Ala
            660                 665                 670

Pro Gly Asn Asp Asn Leu Ile Lys Ala Pro Thr Val Ala Ala Asp Gly
        675                 680                 685

Lys Thr Tyr Ile Val Lys Phe Lys Gln Lys Glu Glu Gly Arg Ser Phe
    690                 695                 700

Thr Lys Ala Ile Glu Asp Ala Lys Lys Glu Lys
705                 710                 715

<210> SEQ ID NO 26
<211> LENGTH: 335
<212> TYPE: PRT
<213> ORGANISM: Murine sp.
<220> FEATURE:
<223> OTHER INFORMATION: Mutant p163

<400> SEQUENCE: 26

Met Ala Lys Arg Val Ala Glu Lys Glu Leu Thr Asp Arg Asn Trp Asp
1               5                   10                  15

Glu Glu Asp Glu Val Glu Glu Met Gly Thr Phe Ser Val Ala Ser Glu
                20                  25                  30

Glu Val Met Lys Asn Arg Ala Val Lys Lys Ala Lys Arg Arg Asn Val
            35                  40                  45
```

-continued

```
Gly Phe Glu Ser Asp Ser Gly Ala Phe Lys Gly Phe Lys Gly Leu
         50                  55                  60

Val Val Pro Ser Gly Gly Gly Phe Ser Gly Phe Gly Gly Ser Gly
 65                  70                  75                  80

Gly Lys Pro Leu Glu Gly Leu Thr Asn Gly Asn Ser Thr Asp Asn Ala
                     85                  90                  95

Thr Pro Phe Ser Asn Val Lys Thr Ala Ala Glu Pro Lys Ala Ala Phe
                100                 105                 110

Gly Ser Phe Ala Val Asn Gly Pro Phe Thr Ala Glu Lys Lys Ser Asp
                115                 120                 125

Ala Ala Gln Gly Ala Thr Ser Ala Ser Phe Ser Phe Gly Lys Lys Ile
                130                 135                 140

Glu Ser Ser Ala Leu Gly Ser Leu Ser Ser Gly Ser Leu Thr Gly Phe
145                 150                 155                 160

Ser Phe Ser Ala Gly Ser Ser Ser Leu Phe Gly Lys Asp Ala Ala Gln
                165                 170                 175

Ser Lys Ala Ala Ser Ser Leu Phe Ser Ala Lys Ala Ser Glu Ser Pro
                180                 185                 190

Ala Gly Gly Gly Ser Ser Glu Cys Arg Asp Gly Glu Glu Glu Asn
                195                 200                 205

Asp Glu Pro Pro Lys Val Val Thr Glu Val Lys Glu Glu Asp Ala
210                 215                 220

Phe Tyr Ser Lys Lys Cys Lys Leu Phe Tyr Lys Lys Asp Asn Glu Phe
225                 230                 235                 240

Lys Glu Lys Gly Val Gly Thr Leu His Leu Lys Pro Thr Ala Thr Gln
                245                 250                 255

Lys Thr Gln Leu Leu Val Arg Ala Asp Thr Asn Leu Gly Asn Ile Leu
                260                 265                 270

Leu Asn Val Leu Ile Ala Pro Asn Met Pro Cys Thr Arg Thr Gly Lys
                275                 280                 285

Asn Asn Val Leu Ile Val Cys Val Pro Asn Pro Pro Leu Asp Glu Lys
                290                 295                 300

Gln Pro Thr Leu Pro Ala Thr Met Leu Ile Arg Val Lys Thr Ser Glu
305                 310                 315                 320

Asp Ala Asp Glu Leu His Lys Ile Leu Leu Glu Lys Lys Asp Ala
                325                 330                 335

<210> SEQ ID NO 27
<211> LENGTH: 310
<212> TYPE: PRT
<213> ORGANISM: Murine sp.
<220> FEATURE:
<223> OTHER INFORMATION: Mutant p163

<400> SEQUENCE: 27

Met Ala Lys Arg Val Ala Glu Lys Glu Leu Thr Asp Arg Asn Trp Asp
 1                   5                  10                  15

Glu Glu Asp Glu Val Glu Glu Met Gly Thr Phe Ser Val Ala Ser Glu
                 20                  25                  30

Glu Val Met Lys Asn Arg Ala Val Lys Lys Ala Lys Arg Arg Asn Val
             35                  40                  45

Gly Phe Glu Ser Asp Ser Gly Ala Phe Lys Gly Phe Lys Gly Leu
         50                  55                  60

Val Val Pro Ser Gly Gly Gly Phe Ser Gly Phe Gly Gly Ser Gly
 65                  70                  75                  80
```

```
Gly Lys Pro Leu Glu Gly Leu Thr Asn Gly Asn Ser Thr Asp Asn Ala
                85                  90                  95

Thr Pro Phe Ser Asn Val Lys Thr Ala Ala Glu Pro Lys Ala Ala Phe
            100                 105                 110

Gly Ser Phe Ala Val Asn Gly Pro Thr Thr Leu Val Asp Lys Val Ser
            115                 120                 125

Asn Pro Lys Thr Asn Gly Asp Ser Asn Gln Pro Pro Ser Ser Gly Pro
130                 135                 140

Ala Ser Thr Ala Cys Pro Gly Asn Ala Tyr His Lys Gln Leu Ala
145                 150                 155                 160

Gly Leu Asn Cys Ser Val Arg Asp Trp Ile Val Lys His Val Asn Ile
                165                 170                 175

Asn Pro Leu Cys Asp Leu Thr Pro Ile Phe Lys Asp Tyr Glu Arg Tyr
            180                 185                 190

Leu Ala Thr Ile Glu Lys Gln Leu Glu Asn Gly Gly Gly Ser Ser Ser
            195                 200                 205

Glu Ser Gln Thr Asp Arg Ala Thr Ala Gly Met Glu Pro Pro Ser Leu
210                 215                 220

Phe Gly Ser Thr Lys Leu Gln Gln Glu Ser Pro Phe Ser Phe His Gly
225                 230                 235                 240

Asn Lys Ala Glu Asp Thr Ser Glu Lys Val Glu Phe Thr Ala Glu Lys
                245                 250                 255

Lys Ser Asp Ala Ala Gln Gly Ala Thr Ser Ala Ser Phe Ser Phe Gly
            260                 265                 270

Lys Lys Ile Glu Ser Ser Ala Leu Gly Ser Leu Ser Ser Gly Ser Leu
            275                 280                 285

Thr Gly Phe Ser Phe Ser Ala Gly Ser Ser Ser Leu Phe Gly Lys Asp
            290                 295                 300

Ala Ala Glu Lys Glu Leu
305                 310

<210> SEQ ID NO 28
<211> LENGTH: 132
<212> TYPE: PRT
<213> ORGANISM: Murine sp.

<400> SEQUENCE: 28

Thr Thr Leu Val Asp Lys Val Ser Asn Pro Lys Thr Asn Gly Asp Ser
 1               5                  10                  15

Asn Gln Pro Pro Ser Ser Gly Pro Ala Ser Ser Thr Ala Cys Pro Gly
                20                  25                  30

Asn Ala Tyr His Lys Gln Leu Ala Gly Leu Asn Cys Ser Val Arg Asp
            35                  40                  45

Trp Ile Val Lys His Val Asn Thr Asn Pro Leu Cys Asp Leu Thr Pro
50                  55                  60

Ile Phe Lys Asp Tyr Glu Arg Tyr Leu Ala Thr Ile Glu Lys Gln Leu
65                  70                  75                  80

Glu Asn Gly Gly Gly Ser Ser Ser Glu Ser Gln Thr Asp Arg Ala Thr
                85                  90                  95

Ala Gly Met Glu Pro Pro Ser Leu Phe Gly Ser Thr Lys Leu Gln Gln
            100                 105                 110

Glu Ser Pro Phe Ser Phe His Gly Asn Lys Ala Glu Asp Thr Ser Glu
            115                 120                 125

Lys Val Glu Phe
130
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 29
agaaagcaaa gcgcagaaat gt                                             22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
caaatccaga aaagcgtcct c                                              21

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 31
tgaagaatag agccataaag aaag                                           24

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 32
agaaaagcgt cctcctccag a                                              21

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 33
tgaagaatag agccataaag aaag                                           24

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 34
agcgccacta accaaatcca ga                                             22

<210> SEQ ID NO 35
<211> LENGTH: 22
<212> TYPE: DNA
<213> ORGANISM: Artificial Sequence
<220> FEATURE:

```
<223> OTHER INFORMATION: Description of Artificial Sequence: Primer

<400> SEQUENCE: 35
agaaagcaaa gcgcagaaat gt                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 36
gaaaagcgtc ctcctccaga ag                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 37
gaaagcaaag cgcagaaatg tt                                              22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 38
ctccagcgcc actaccaaat c                                               21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 39
cccgcacgga gcagttcaag                                                 20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 40
gcagcggcag atcccaaggt ag                                              22

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 41
ggcatccttt ttctcca                                                    17
```

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 42
cgttcttatc gtctctgtgt tc                                    22

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 43
gcatcctttt tctccagta                                        19

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 44
tgttccaaat ccaccaat                                         18

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 45
gtctgcatcc tcgctggtt                                        19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 46
cgttcttatc gtctgtgttc c                                     21

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 47
ttttacccga atcaacat                                         18

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Primer -continued

```
<400> SEQUENCE: 48
gtacgcgaac agggaagaat a                                              21

<210> SEQ ID NO 49
<211> LENGTH: 212
<212> TYPE: PRT
<213> ORGANISM: Artificial Sequence
<220> FEATURE:
<223> OTHER INFORMATION: Description of Artificial Sequence: Consensus

<400> SEQUENCE: 49
```

Arg Val Ser Asn Gly Ser Pro Ser Leu Glu Arg Met Asp Ala Arg Gln
 1               5                  10                  15

Ala Asp His Pro Lys Pro Ser Ala Cys Arg Asn Leu Phe Gly Pro Val
             20                  25                  30

Asn His Gly Glu Leu Thr Arg Asp Leu Glu Lys His Cys Arg Asp Met
         35                  40                  45

Glu Glu Ala Ser Gln Arg Lys Trp Asn Phe Asp Phe Gln Asn His Lys
     50                  55                  60

Pro Leu Glu Gly Arg Tyr Glu Trp Gln Glu Val Glu Arg Gly Ser Leu
 65                  70                  75                  80

Pro Glu Phe Tyr Tyr Arg Pro Arg Pro Lys Ser Ala Cys Lys
                 85                  90                  95

Val Leu Ala Gln Glu Ser Gln Asp Val Ser Gly Ser Arg Gln Ala Val
            100                 105                 110

Pro Leu Ile Gly Ser Gln Ala Asn Ser Glu Asp Arg His Leu Val Asp
        115                 120                 125

Gln Met Pro Asp Ser Ser Asp Asn Gln Ala Gly Leu Ala Glu Gln Cys
    130                 135                 140

Pro Gly Met Arg Lys Arg Pro Ala Ala Glu Asp Ser Ser Ser Gln Ile
145                 150                 155                 160

Lys Arg Ala Asn Arg Thr Glu Glu Asn Val Ser Asp Gly Ser Pro Asn
                165                 170                 175

Ala Gly Thr Val Glu Gln Thr Pro Lys Lys Pro Gly Leu Arg Arg Gln
            180                 185                 190

Thr Arg Val Asp Leu Gln Pro Ser Phe Arg Ala Asn Phe Leu Phe Met
        195                 200                 205

Ile Phe Ile Lys
    210

```
<210> SEQ ID NO 50
<211> LENGTH: 180
<212> TYPE: PRT
<213> ORGANISM: Murine sp.
<220> FEATURE:
<223> OTHER INFORMATION: mutated p27

<400> SEQUENCE: 50
```

Met Asp Ala Arg Gln Ala Asp His Pro Lys Pro Ser Ala Cys Arg Asn
 1               5                  10                  15

Leu Phe Gly Pro Val Asn His Gly Glu Leu Thr Arg Asp Leu Glu Lys
             20                  25                  30

His Cys Arg Asp Met Glu Glu Ala Ser Gln Arg Lys Trp Asn Phe Asp
         35                  40                  45

Phe Gln Asn His Lys Pro Leu Glu Gly Arg Tyr Glu Trp Gln Glu Val
     50                  55                  60

Glu Arg Gly Ser Leu Pro Glu Phe Tyr Tyr Arg Pro Pro Cys Pro Pro

```
                65                  70                  75                  80
Lys Ser Ala Cys Lys Val Leu Ala Gln Glu Ser Gln Asp Val Ser Gly
                    85                  90                  95

Ser Arg Gln Ala Val Pro Leu Ile Gly Ser Gln Ala Asn Ser Glu Asp
                100                 105                 110

Arg His Leu Val Asp Gln Met Pro Asp Ser Ser Asp Asn Gln Ala Gly
            115                 120                 125

Leu Ala Glu Gln Cys Pro Gly Met Arg Lys Arg Pro Ala Ala Glu Asp
        130                 135                 140

Ser Ser Ser Gln Ile Lys Arg Ala Asn Arg Thr Glu Glu Asn Val Ser
145                 150                 155                 160

Asp Gly Ser Pro Asn Ala Gly Thr Val Glu Gln Thr Pro Lys Lys Pro
                165                 170                 175

Gly Leu Arg Arg
            180

<210> SEQ ID NO 51
<211> LENGTH: 194
<212> TYPE: PRT
<213> ORGANISM: Murine sp.
<220> FEATURE:
<223> OTHER INFORMATION: mutated p27

<400> SEQUENCE: 51

Arg Val Ser Asn Gly Ser Pro Ser Pro Glu Arg Met Asp Ala Arg Gln
1               5                   10                  15

Ala Asp His Pro Lys Pro Ser Ala Cys Arg Asn Leu Phe Gly Pro Val
                20                  25                  30

Asn His Gly Glu Leu Thr Arg Asp Leu Glu Lys His Cys Arg Asp Met
            35                  40                  45

Glu Glu Ala Ser Gln His Lys Trp Asn Phe Asp Phe Gln Asn His Arg
        50                  55                  60

Pro Leu Glu Gly Arg Tyr Glu Trp Gln Glu Val Glu Arg Gly Ser Leu
65                  70                  75                  80

Pro Glu Phe Tyr Tyr Arg Pro Pro Arg Pro Pro Lys Ser Ala Cys Lys
                85                  90                  95

Val Leu Ala Gln Glu Ser Gln Asp Val Ser Gly Ser Arg Gln Ala Val
                100                 105                 110

Pro Leu Ile Gly Ser Gln Ala Asn Ser Glu Asp Arg His Leu Val Asp
            115                 120                 125

Gln Met Pro Asp Ser Ser Asp Asn Gln Ala Gly Leu Ala Glu Gln Cys
        130                 135                 140

Pro Gly Met Arg Lys Arg Pro Ala Ala Glu Asp Ser Ser Ser Gln Ile
145                 150                 155                 160

Lys Arg Ala Asn Arg Thr Glu Glu Asn Val Ser Asp Gly Ser Pro Asn
                165                 170                 175

Ala Gly Thr Val Glu Gln Thr Pro Lys Lys Pro Gly Pro Arg Arg Gln
                180                 185                 190

Thr Arg

<210> SEQ ID NO 52
<211> LENGTH: 194
<212> TYPE: PRT
<213> ORGANISM: Murine sp.
<220> FEATURE:
<223> OTHER INFORMATION: mutated p27
```

```
<400> SEQUENCE: 52

Arg Val Ser Asn Gly Ser Pro Ser Leu Glu Arg Met Asp Ala Arg Gln
  1               5                  10                  15

Ala Asp His Pro Lys Pro Ser Ala Cys Arg Asn Leu Phe Gly Pro Val
             20                  25                  30

Asn His Gly Glu Leu Thr Arg Asp Leu Glu Lys His Cys Arg Asp Met
             35                  40                  45

Glu Glu Ala Ser Gln Arg Lys Trp Asn Phe Asp Phe Gln Asn His Lys
 50                  55                  60

Pro Leu Glu Gly Arg Tyr Glu Trp Gln Glu Val Glu Arg Gly Ser Leu
 65                  70                  75                  80

Pro Glu Phe Tyr Tyr Gly Pro Pro Arg Pro Lys Ser Ala Cys Lys
                 85                  90                  95

Val Leu Ala Gln Glu Ser Gln Asp Val Gly Ser Arg Gln Ala Val
             100                 105                 110

Pro Leu Ile Gly Ser Gln Ala Asn Ser Glu Asp Arg His Leu Val Asp
             115                 120                 125

Gln Met Pro Asp Ser Ser Asp Asn Gln Ala Gly Leu Ala Glu Gln Cys
130                 135                 140

Pro Gly Met Arg Lys Arg Pro Ala Ala Glu Asp Ser Ser Ser Gln Ile
145                 150                 155                 160

Lys Arg Ala Asn Arg Thr Glu Glu Asn Val Ser Asp Gly Ser Pro Asn
                 165                 170                 175

Ala Gly Thr Val Glu Gln Thr Pro Lys Lys Pro Gly Leu Arg Arg Gln
             180                 185                 190

Thr Arg

<210> SEQ ID NO 53
<211> LENGTH: 193
<212> TYPE: PRT
<213> ORGANISM: Murine sp.
<220> FEATURE:
<223> OTHER INFORMATION: mutated p27

<400> SEQUENCE: 53

Val Ser Asn Gly Ser Pro Ser Leu Glu Arg Met Asp Ala Arg Gln Ala
  1               5                  10                  15

Asp His Pro Lys Pro Ser Ala Cys Arg Asn Leu Phe Gly Pro Val Asn
             20                  25                  30

His Gly Glu Leu Thr Arg Asp Leu Glu Lys His Cys Arg Asp Met Glu
             35                  40                  45

Glu Ala Ser Gln Arg Lys Trp Asn Phe Asp Phe Gln Asn His Lys Pro
 50                  55                  60

Leu Glu Gly Arg Tyr Glu Trp Gln Glu Val Glu Arg Gly Ser Leu Pro
 65                  70                  75                  80

Glu Phe Tyr Tyr Gly Pro Pro Arg Pro Lys Ser Ala Cys Lys Val
                 85                  90                  95

Leu Ala Gln Glu Ser Gln Asp Val Ser Gly Ser Arg Gln Ala Val Pro
             100                 105                 110

Leu Ile Gly Ser Gln Ala Asn Ser Glu Asp Arg His Leu Val Asp Gln
             115                 120                 125

Met Pro Asp Ser Ser Asp Asn Gln Ala Gly Leu Ala Glu Gln Cys Pro
130                 135                 140

Gly Met Arg Lys Arg Pro Ala Ala Glu Asp Ser Ser Ser Gln Ile Lys
145                 150                 155                 160
```

-continued

```
Arg Ala Asn Arg Thr Glu Glu Asn Val Ser Asp Gly Ser Pro Asn Ala
                165                 170                 175

Gly Thr Val Glu Gln Thr Pro Lys Lys Pro Gly Leu Arg Arg Gln Thr
            180                 185                 190

Arg

<210> SEQ ID NO 54
<211> LENGTH: 195
<212> TYPE: PRT
<213> ORGANISM: Murine sp.
<220> FEATURE:
<223> OTHER INFORMATION: mutated p27

<400> SEQUENCE: 54

Asn Val Arg Val Ser Asn Gly Ser Pro Ser Leu Glu Arg Met Asp Ala
 1               5                  10                  15

Arg Gln Ala Asp His Pro Pro Ser Ala Cys Arg Asn Leu Phe Gly Pro
            20                  25                  30

Val Asn His Gly Glu Leu Thr Arg Asp Leu Glu Lys His Cys Arg Asp
        35                  40                  45

Met Glu Glu Ala Ser Gln Arg Lys Trp Asn Phe Asp Phe Gln Asn His
    50                  55                  60

Lys Pro Leu Glu Gly Arg Tyr Glu Trp Gln Glu Val Glu Arg Gly Ser
65                  70                  75                  80

Leu Pro Glu Phe Tyr Tyr Arg Pro Pro Arg Pro Pro Lys Ser Ala Cys
                85                  90                  95

Lys Val Pro Ala Gln Glu Ser Gln Asp Val Ser Gly Ser Arg Gln Ala
            100                 105                 110

Val Pro Leu Ile Gly Ser Gln Ala Asn Ser Glu Asp Arg His Leu Val
        115                 120                 125

Asp Gln Met Pro Asp Ser Ser Asp Asn Gln Ala Gly Leu Ala Glu Gln
    130                 135                 140

Cys Pro Gly Met Arg Lys Arg Pro Ala Ala Glu Asp Ser Ser Ser Gln
145                 150                 155                 160

Ile Lys Arg Ala Asn Arg Thr Glu Glu Asn Val Ser Asp Gly Ser Pro
                165                 170                 175

Asn Ala Gly Thr Val Glu Gln Thr Pro Lys Lys Pro Gly Leu Arg Arg
            180                 185                 190

Gln Thr Arg
        195

<210> SEQ ID NO 55
<211> LENGTH: 180
<212> TYPE: PRT
<213> ORGANISM: Murine sp.
<220> FEATURE:
<223> OTHER INFORMATION: mutated p27

<400> SEQUENCE: 55

Met Asp Ala Arg Gln Ala Asp His Pro Lys Pro Ser Ala Cys Arg Asn
 1               5                  10                  15

Leu Phe Gly Pro Val Asn His Gly Glu Leu Thr Arg Asp Leu Glu Lys
            20                  25                  30

His Cys Gln Asp Met Glu Glu Ala Ser Gln Arg Lys Trp Asn Phe Asp
        35                  40                  45

Phe Gln Asn His Lys Pro Leu Glu Gly Arg Tyr Glu Trp Gln Glu Val
    50                  55                  60
```

```
Glu Arg Gly Ser Leu Pro Glu Phe Tyr Tyr Arg Pro Pro Arg Pro Pro
 65                  70                  75                  80

Lys Ser Ala Cys Lys Val Leu Ala Gln Glu Ser Gln Asp Val Ser Gly
                 85                  90                  95

Ser Arg Gln Ala Val Pro Leu Ile Gly Ser Gln Ala Asn Ser Glu Asp
            100                 105                 110

Arg His Leu Val Asp Gln Met Pro Asp Ser Asp Asn Gln Ala Gly
        115                 120                 125

Leu Ala Glu Gln Cys Pro Gly Met Arg Lys Arg Pro Ala Ala Glu Asp
    130                 135                 140

Ser Ser Ser Gln Ile Lys Arg Ala Asn Arg Thr Glu Glu Asn Val Ser
145                 150                 155                 160

Asp Gly Ser Pro Asn Ala Gly Thr Val Glu Gln Thr Pro Lys Lys Pro
                165                 170                 175

Gly Leu Arg Arg
            180

<210> SEQ ID NO 56
<211> LENGTH: 135
<212> TYPE: PRT
<213> ORGANISM: Murine sp.
<220> FEATURE:
<223> OTHER INFORMATION: mutated p27

<400> SEQUENCE: 56

Met Asp Ala Arg Gln Ala Asp His Pro Lys Pro Ser Ala Cys Arg Asn
  1               5                  10                  15

Leu Phe Gly Pro Val Asn His Gly Glu Leu Thr Arg Asp Leu Glu Lys
                 20                  25                  30

His Cys Arg Asp Met Glu Glu Ala Ser Gln Arg Lys Trp Asn Phe Asp
            35                  40                  45

Phe Gln Asn His Lys Pro Leu Glu Gly Arg Tyr Glu Trp Gln Glu Val
    50                  55                  60

Glu Arg Gly Ser Leu Pro Glu Phe Tyr Tyr Gly Pro Pro Arg Pro Pro
 65                  70                  75                  80

Lys Ser Ala Cys Lys Val Leu Ala Gln Glu Ser Gln Asp Val Ser Gly
                 85                  90                  95

Ser Arg Gln Ala Val Pro Leu Ile Gly Ser Gln Ala Asn Ser Glu Asp
            100                 105                 110

Arg His Leu Val Asp Gln Met Pro Asp Ser Ser Asp Ser Gln Ala Gly
        115                 120                 125

Leu Ala Glu Gln Cys Pro Gly
    130                 135

<210> SEQ ID NO 57
<211> LENGTH: 197
<212> TYPE: PRT
<213> ORGANISM: Murine sp.

<400> SEQUENCE: 57

Met Ser Asn Val Arg Val Ser Asn Gly Ser Pro Ser Leu Glu Arg Met
  1               5                  10                  15

Asp Ala Arg Gln Ala Asp His Pro Lys Pro Ser Ala Cys Arg Asn Leu
                 20                  25                  30

Phe Gly Pro Val Asn His Glu Glu Leu Thr Arg Asp Leu Glu Lys His
            35                  40                  45
```

-continued

```
Cys Arg Asp Met Glu Glu Ala Ser Gln Arg Lys Trp Asn Phe Asp Phe
     50                  55                  60

Gln Asn His Lys Pro Leu Glu Gly Arg Tyr Glu Trp Gln Glu Val Glu
 65              70                  75                      80

Arg Gly Ser Leu Pro Glu Phe Tyr Tyr Arg Pro Pro Arg Pro Pro Lys
                 85                  90                  95

Ser Ala Cys Lys Val Leu Ala Gln Glu Ser Gln Asp Val Ser Gly Ser
            100                 105                 110

Arg Gln Ala Val Pro Leu Ile Gly Ser Gln Ala Asn Ser Glu Asp Arg
            115             120                 125

His Leu Val Asp Gln Met Pro Asp Ser Ser Asp Asn Gln Ala Gly Leu
        130             135                 140

Ala Glu Gln Cys Pro Gly Met Arg Lys Arg Pro Ala Ala Glu Asp Ser
145             150                 155                     160

Ser Ser Gln Asn Lys Arg Ala Asn Arg Thr Glu Glu Asn Val Ser Asp
                165                 170                 175

Gly Ser Pro Asn Ala Gly Thr Val Glu Gln Thr Pro Lys Lys Pro Gly
            180                 185                 190

Leu Arg Arg Gln Thr
            195
```